(12) United States Patent
Moley et al.

(10) Patent No.: US 9,381,193 B2
(45) Date of Patent: Jul. 5, 2016

(54) CONTRACEPTIVE METHODS AND COMPOSITIONS

(75) Inventors: Kelle H. Moley, St. Louis, MO (US); Antonina I. Frolova, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 22 days.

(21) Appl. No.: 13/436,469

(22) Filed: Mar. 30, 2012

(65) Prior Publication Data
US 2013/0065853 A1    Mar. 14, 2013

Related U.S. Application Data

(60) Provisional application No. 61/470,925, filed on Apr. 1, 2011.

(51) Int. Cl.
| | | |
|---|---|---|
| *A61K 31/5685* | (2006.01) | |
| *A61P 15/18* | (2006.01) | |
| *A61K 31/455* | (2006.01) | |
| *A61K 31/7008* | (2006.01) | |

(52) U.S. Cl.
CPC ........... *A61K 31/455* (2013.01); *A61K 31/5685* (2013.01); *A61K 31/7008* (2013.01)

(58) Field of Classification Search
CPC ... A61K 31/70; A61K 31/7008; A61K 31/45; A61K 31/566; A61K 31/08; A61K 31/655; A61K 31/166; A61K 31/70041; A61K 31/5685; A61K 31/455
USPC .............. 514/23, 62, 178, 221, 352, 707, 179
See application file for complete search history.

(56) References Cited

U.S. PATENT DOCUMENTS

| | | | | |
|---|---|---|---|---|
| 5,439,913 | A * | 8/1995 | Chwalisz ............... | A61K 31/00 514/277 |
| 5,854,229 | A * | 12/1998 | Labrie ........................ | 514/169 |
| 6,476,079 | B1 * | 11/2002 | Jukarainen .......... | A61K 9/0024 424/422 |
| 7,776,366 | B2 * | 8/2010 | Davenport et al. .......... | 424/725 |
| 2004/0192620 | A1 * | 9/2004 | Bunschoten et al. .......... | 514/26 |
| 2005/0037033 | A1 * | 2/2005 | Camus-Bablon et al. .... | 424/400 |
| 2006/0084604 | A1 | 4/2006 | Kitaura | |
| 2009/0258046 | A1 * | 10/2009 | Nyce .............................. | 424/422 |

OTHER PUBLICATIONS

Barad, D. et al., Human Reproduction, "Effect of dehydroepiandrosterone on oocyte and embryo yields, embryo grade and cell number in IVF", 2006, vol. 21, No. 11, pp. 2845-2849.*
Gleicher, N. et al., Reproductive Biology and Endocrinology, "Miscarriage rates after dehydroepiandrosterone (DHEA) supplementation in women with diminished ovarian reserve: a case control study", 2009, vol. 7.*
Wiser, A. et al., Human Reproduction, "Addition of dehydroepiandrosterone (DHEA) for poor-responder patients before and during IVF treatment improves the pregnancy rate: A randomized prospective study", 2010, vol. 25, No. 10, pp. 2496-2500.*
WordNet Search 3.0, "prevent", also available at http://wordnetweb.princeton.edu/perl/webwn?s=prevent&sub=Search+WordNet&o2=&o0=1&o8=1&o1=1&o7=&o5=&o9=&o6=&o3=&o4=&h=; last viewed Dec. 10, 2013.*
Sander, Valeria et al., Neuroimmunomodulation, "The Influence of Dehydroepiandrosterone on Early Pregnancy in Mice", 2005, vol. 12, pp. 285-292.*
Schelbach, Cheryl J. et al., Reproduction, Fertility and Development, "Mechanics contributing to the reduced developmental competence of glucosamine-exposed mouse oocytes", 2010, vol. 22, pp. 771-779.*
Sourla, Antigone et al., J. Steroid Biochem. Molec. Biol., "Effect of Dehydroepiandrosterone on Vaginal and Uterine Histomorphology in the Rat", 1998, vol. 66, No. 3, pp. 137-149.*
Suh-Burgmann, Elizabeth et al., Gynecol Obstet Invest, "Long-term Administration of Intravaginal Dehydroepiandrosterone on Regression of Low-Grade Cervical Dysplasia—A Pilot Study", 2003, vol. 55, pp. 25-31.*
Chamberlain, J. G. "Deleterious Effects of 6-Aminonicotinamide on Implantation and Early Embryonic Development in Long-Evans Rat." Anatomical Record, 1963, vol. 145. No. 2., abstract.*
Elia, Evelin et al., International Immunopharmacology, "Detrimental effects of hyperandrogenism on utrine functions", 2008, vol. 8, pp. 1827-1834.*
Frolova, Antonina et al., Endocrinology, "Facilitative Glucose Transporter Type 1 is Differentially Regulated by Progesterone and Estrogen in Murine and Human Endometrial Stromal Cells", 2009, vol. 150, No. 3, pp. 1512-1520.*
Hackl, Heinrich, Acta Obstet Gynec Scand, "Metabolism of Glucose in the Human Endometrium with Special Reference to Fertility and Contraception", 1973, vol. 52, pp. 135-140.*
Tuckerman, E. M. et al., Fertility and Sterility, "Do Androgens Have a Direct Effect on Endometrial Function? An In Vitro Study", 2000, vol. 74, No. 4, pp. 771-779.*
Ramathal, Cy, et al., "Endometrial Decidualization: Of Mice and Men", Semin Reprod Med., Jan. 2010, 28(1): 17-26, p. 2.
Frolova, Dehydroepiandrosterone Inhibits Glucose Flux Through the Pentose Phosphate Pathway in Human and Mouse Endometrial Stromal Cells, Preventing Decidualization and Implantation, Mol Endocrinol, Aug. 2011, 1444-1455, 25(8).
Kara, Does dehydroepiandrosterone supplementation really affect IVF-ICSI outcome in women with poor ovarian reserve?, European Journal of Obstetrics & Gynecology and Reproductive Biology, 2014, 63-65, 173.
Narkwichean, Efficacy of dehydroepiandrosterone to improve ovarian response in women with diminished ovarian reserve: a meta-analysis, Reproductive Biology and Endocrinology, 2013, 8 pgs, 11:44.
Tsi, Glucosamine inhibits decidualization of human endometrial stromal cells and decreases litter size in mice, Biology of Reproduction, 2013, 1-10, 89(1):16.
Data Standards Manual, Route of Administration, U.S. Food and Drug Administration, Protecting and Promoting Your Health, 7 pgs, printed on Sep. 7, 2015 from www.fda.gov/Drugs/DevelopmentApprovalProcess/FormsSubmissionRequirements/ElectronicSubmissions/DataStandardsManualmonographs/um017 . . .

(Continued)

*Primary Examiner* — Jonathan S Lau
*Assistant Examiner* — Bahar Craigo
(74) *Attorney, Agent, or Firm* — Polsinelli PC

(57) ABSTRACT

The invention encompasses compositions and methods for use in preventing pregnancy.

5 Claims, 44 Drawing Sheets
(18 of 44 Drawing Sheet(s) Filed in Color)

(56) References Cited

OTHER PUBLICATIONS

Chaouat, Immunology of Pregnancy, 1993, p. 174, CRC Press, Inc., Boca Raton, Florida.

Guay, Testosterone insufficiency in women: fact or fiction?, World J Urol, 2002, pp. 106-110, vol. 20.

Duncan, Striking differences in Aloe vera gel carbohydrate composition, molecular weight and particle size distributions following processing will not be addressed by dietary supplement GMPs, 5th Annual Natural Supplements Conference, Jan. 2008, 5 pgs.

* cited by examiner

Control

Decidualized

Decidualized
+100DHEA

Control 0.01% DHEA 0.1% DHEA 0.6% DHEA

SEQUENCE LISTING

```
<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
atcgaccact acctgggcaa                                              20

<210> SEQ ID NO 2
<211> LENGTH: 19
<212> TYPE: DNA
<213> ORGANISM: Homo sapiens

<400> SEQUENCE: 2
ttctgcatca cgtcccgga                                               19
```

CONTRACEPTIVE METHODS AND COMPOSITIONS

CROSS REFERENCE TO RELATED APPLICATIONS

This application claims the priority of U.S. provisional application No. 61/470,925 filed Apr. 1, 2011, which is hereby incorporated by reference in its entirety.

GOVERNMENTAL RIGHTS

This invention was made with government support under R01 HD065435 awarded by the National Institute of Child Health and Development and F30 DK083224 awarded by the National Institute of Diabetes and Digestive and Kidney Disease. The government has certain rights in the invention.

FIELD OF THE INVENTION

The invention encompasses compositions and methods for use in preventing pregnancy.

BACKGROUND OF THE INVENTION

Available hormone-based methods of contraception are not always effective and may present serious side effects. For example, all estrogen-based therapies are known to increase the risk of endometrial hyperplasia and cancer, as well as the risk of breast cancer, in treated individuals. Even estrogen/progestin combinations designed to relieve some of the side effects of unopposed estrogen therapies result in a number of side effects, including uterine bleeding and the continuation of menstrual periods. Accordingly, there remains a need in the art to provide safer and more effective methods of contraception.

SUMMARY OF THE INVENTION

One aspect of the present invention encompasses a method of preventing pregnancy. The method comprises blocking decidualization of the endometrial stromal cells in the uterus by locally administering an inhibitor of the pentose phosphate pathway.

Another aspect of the present invention encompasses a method of preventing pregnancy. The method comprises inhibiting the pentose phosphate pathway in the uterus, wherein the pentose phosphate pathway is inhibited by administering an inhibitor of the pentose phosphate pathway.

Other aspects and iterations of the invention are detailed below.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION OF THE INVENTION

Figure 1A:
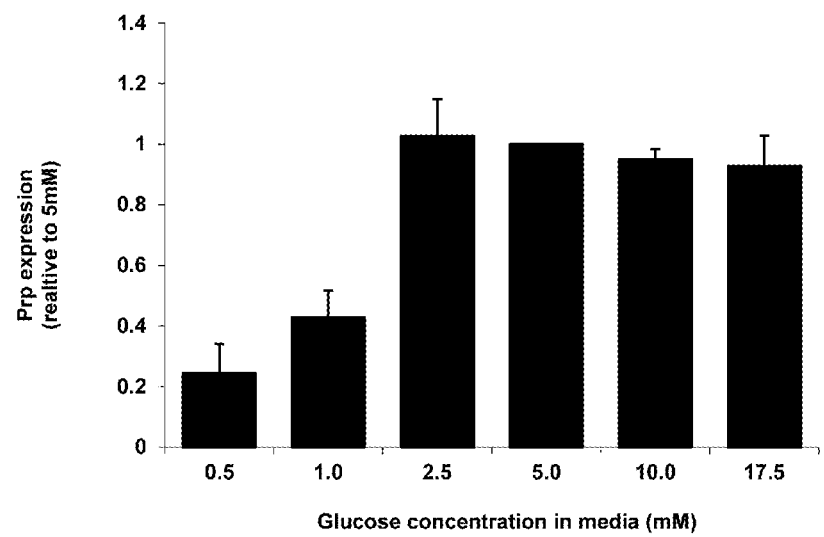
FIG. 1A-B depicts histograms of marker expression under various concentrations of glucose. (A) Expression of decidualization marker, Prp, in murine ESCs cultured at different concentrations of glucose. (B). Expression of decidualization markers Prl and Igfbp1 in human ESCs cultured in different concentrations of glucose.

The present invention discloses methods of preventing pregnancy. More specifically, the present disclosure provides methods of preventing pregnancy by inhibiting the pentose phosphate pathway (PPP). Inhibiting the PPP prevents the proliferative and secretory phases of the menstrual cycle. Advantageously, safe and effective PPP inhibitors that may be used to prevent pregnancy are known. In addition, PPP inhibitors may be administered locally to avoid any unintended results of systemic administration.

(a) The Pentose Phosphate Pathway and Pregnancy.

The present disclosure provides methods of preventing pregnancy by inhibiting the pentose phosphate pathway (PPP). As used herein, "preventing" encompasses reducing the likelihood of pregnancy as well as prohibiting pregnancy. The success of a pregnancy is determined by the completion of a number of sequential processes with proper implantation of the embryo being one of the initial key factors. During implantation, the embryo adheres to the wall of the uterus. The implantation window is started by preparations in the endometrium of the uterus, both structurally and in the composition of its secretions. Failure of the endometrium to properly differentiate towards a receptive state results in prevention of pregnancy. One of the key processes in uterine preparation for embryo receptivity is the differentiation of endometrial stromal cells (ESCs) into decidual cells (decidualization), which are crucial for the early stages of implantation. As described in the examples, it was discovered that improper flux of internalized glucose into the PPP may inhibit decidualization and may result in prevention of pregnancy. Improper flux of internalized glucose into the PPP may inhibit the proliferative and secretory phases of the menstrual cycle. Hence, the invention encompasses the inhibition of the PPP to inhibit the proliferative and secretory phases of the menstrual cycle.

The PPP produces NADPH for biosynthesis of cholesterol, fatty acids and reduced glutathione, and ribose 5-phosphate for biosynthesis of nucleotides using the glucose-6-phosphate dehydrogenase (G6PD), lactonase, 6-phosphogluconate dehydrogenase, phosphopentose isomerase, phosphopentose epimerase, transketolase, and transaldolase enzymes.

(b) Methods of Inhibiting the PPP.

Non-limiting examples of methods of inhibiting the PPP may include small molecule inhibitors that are specific to an enzyme in the PPP, hormones that inhibit the PPP or an RNA interference (RNAi) agent directed at enzymes of the PPP. In some embodiments, the PPP may be inhibited by hormones. Non-limiting examples of hormones that may inhibit the PPP include epiandrosterone, dehydroepiandrosterone (DHEA)-sulfate, halogenated DHEA, DHEA, and 16α-bromoepiandrosterone. In other embodiments, the PPP may be inhibited by small molecule inhibitors that are specific to an enzyme in the PPP. The PPP may be inhibited by inhibiting one, two, three, four, five, six, or seven enzymes in the PPP. Table 1 lists preferred combinations of inhibited PPP enzymes. For example, those rows having a single entry indicate a single enzyme of the PPP may be inhibited. Subsequent rows indicate multiple enzymes of the PPP may be inhibited. G6PD converts glucose-6-phosphate into 6-phosphoglucono-δ-lactone and is the rate-limiting enzyme of the pentose phosphate pathway. In an exemplary embodiment, the G6PD enzyme is inhibited.

TABLE 1

| PPP enzyme combinations |
|---|
| G6PD |
| lactonase |
| 6-phosphogluconate dehydrogenase |
| phosphopentose isomerase |
| phosphopentose epimerase |
| transketolase |
| transaldolase |
| G6PD, lactonase |
| G6PD, 6-phosphogluconate dehydrogenase |
| G6PD, phosphopentose isomerase |
| G6PD, phosphopentose epimerase |
| G6PD, transketolase |
| G6PD, transaldolase |
| lactonase, 6-phosphogluconate dehydrogenase |
| lactonase, phosphopentose isomerase |
| lactonase, phosphopentose epimerase |
| lactonase, transketolase |
| lactonase, transaldolase |
| 6-phosphogluconate dehydrogenase, phosphopentose isomerase |
| 6-phosphogluconate dehydrogenase, phosphopentose epimerase |
| 6-phosphogluconate dehydrogenase, transketolase |
| 6-phosphogluconate dehydrogenase, transaldolase |
| phosphopentose isomerase, phosphopentose epimerase |
| phosphopentose isomerase, transketolase |
| phosphopentose isomerase, transaldolase |
| phosphopentose epimerase, transketolase |
| phosphopentose epimerase, transaldolase |
| transketolase, transaldolase |
| G6PD, lactonase, 6-phosphogluconate dehydrogenase |
| G6PD, lactonase, phosphopentose isomerase |
| G6PD, lactonase, phosphopentose epimerase |
| G6PD, lactonase, transketolase |
| G6PD, lactonase, transaldolase |
| G6PD, 6-phosphogluconate dehydrogenase, phosphopentose isomerase |
| G6PD, 6-phosphogluconate dehydrogenase, phosphopentose epimerase |
| G6PD, 6-phosphogluconate dehydrogenase, transketolase |
| G6PD, 6-phosphogluconate dehydrogenase, transaldolase |
| G6PD, phosphopentose isomerase, phosphopentose epimerase |
| G6PD, phosphopentose isomerase, transketolase |
| G6PD, phosphopentose isomerase, transaldolase |
| G6PD, phosphopentose epimerase, transketolase |
| G6PD, phosphopentose epimerase, transaldolase |
| G6PD, transketolase, transaldolase |
| lactonase, 6-phosphogluconate dehydrogenase, phosphopentose isomerase |
| lactonase, 6-phosphogluconate dehydrogenase, phosphopentose epimerase |
| lactonase, 6-phosphogluconate dehydrogenase, transketolase |
| lactonase, 6-phosphogluconate dehydrogenase, transaldolase |
| lactonase, phosphopentose isomerase, phosphopentose epimerase |
| lactonase, phosphopentose isomerase, transketolase |
| lactonase, phosphopentose isomerase, transaldolase |
| lactonase, phosphopentose epimerase, transketolase |
| lactonase, phosphopentose epimerase, transaldolase |
| lactonase, transketolase, transaldolase |
| 6-phosphogluconate dehydrogenase, phosphopentose isomerase, phosphopentose epimerase |
| 6-phosphogluconate dehydrogenase, phosphopentose isomerase, transketolase |

TABLE 1-continued

PPP enzyme combinations 6-phosphogluconate dehydrogenase, phosphopentose isomerase, transaldolase
6-phosphogluconate dehydrogenase, phosphopentose epimerase, transketolase
6-phosphogluconate dehydrogenase, phosphopentose epimerase, transaldolase
6-phosphogluconate dehydrogenase, transketolase, transaldolase
phosphopentose isomerase, phosphopentose epimerase, transketolase
phosphopentose isomerase, phosphopentose epimerase, transaldolase
phosphopentose isomerase, transketolase, transaldolase
phosphopentose epimerase, transketolase, transaldolase
G6PD, lactonase, 6-phosphogluconate dehydrogenase, phosphopentose isomerase
G6PD, lactonase, 6-phosphogluconate dehydrogenase, phosphopentose epimerase
G6PD, lactonase, 6-phosphogluconate dehydrogenase, transketolase
G6PD, lactonase, 6-phosphogluconate dehydrogenase, transaldolase
G6PD, lactonase, phosphopentose isomerase, phosphopentose epimerase
G6PD, lactonase, phosphopentose isomerase, transketolase
G6PD, lactonase, phosphopentose isomerase, transaldolase
G6PD, lactonase, phosphopentose epimerase, transketolase
G6PD, lactonase, phosphopentose epimerase, transaldolase
G6PD, lactonase, transketolase, transaldolase
G6PD, 6-phosphogluconate dehydrogenase, phosphopentose isomerase, phosphopentose epimerase
G6PD, 6-phosphogluconate dehydrogenase, phosphopentose isomerase, transketolase
G6PD, 6-phosphogluconate dehydrogenase, phosphopentose isomerase, transaldolase
G6PD, 6-phosphogluconate dehydrogenase, phosphopentose epimerase, transketolase
G6PD, 6-phosphogluconate dehydrogenase, phosphopentose epimerase, transaldolase
G6PD, 6-phosphogluconate dehydrogenase, transketolase, transaldolase
G6PD, phosphopentose isomerase, phosphopentose epimerase, transketolase
G6PD, phosphopentose isomerase, phosphopentose epimerase, transaldolase
G6PD, phosphopentose isomerase, transketolase, transaldolase
G6PD, phosphopentose epimerase, transketolase, transaldolase
lactonase, 6-phosphogluconate dehydrogenase, phosphopentose isomerase, phosphopentose epimerase
lactonase, 6-phosphogluconate dehydrogenase, phosphopentose isomerase, transketolase
lactonase, 6-phosphogluconate dehydrogenase, phosphopentose isomerase, transaldolase
lactonase, 6-phosphogluconate dehydrogenase, phosphopentose epimerase, transketolase
lactonase, 6-phosphogluconate dehydrogenase, phosphopentose epimerase, transaldolase
lactonase, 6-phosphogluconate dehydrogenase, transketolase, transaldolase
lactonase, phosphopentose isomerase, phosphopentose epimerase, transketolase
lactonase, phosphopentose isomerase, phosphopentose epimerase, transaldolase
lactonase, phosphopentose isomerase, transketolase, transaldolase
lactonase, phosphopentose epimerase, transketolase, transaldolase
6-phosphogluconate dehydrogenase, phosphopentose isomerase, phosphopentose epimerase, transketolase
6-phosphogluconate dehydrogenase, phosphopentose isomerase, phosphopentose epimerase, transaldolase
6-phosphogluconate dehydrogenase, phosphopentose isomerase, transketolase, transaldolase
6-phosphogluconate dehydrogenase, phosphopentose epimerase, transketolase, transaldolase
phosphopentose isomerase, phosphopentose epimerase, transketolase, transaldolase
G6PD, lactonase, 6-phosphogluconate dehydrogenase, phosphopentose isomerase, phosphopentose epimerase
G6PD, lactonase, 6-phosphogluconate dehydrogenase, phosphopentose isomerase, transketolase
G6PD, lactonase, 6-phosphogluconate dehydrogenase, phosphopentose isomerase, transaldolase
G6PD, lactonase, 6-phosphogluconate dehydrogenase, phosphopentose epimerase,transaldolase
G6PD, lactonase, 6-phosphogluconate dehydrogenase, transketolase, transaldolase
G6PD, lactonase, phosphopentose isomerase, phosphopentose epimerase, transketolase
G6PD, lactonase, phosphopentose isomerase, phosphopentose epimerase, transaldolase
G6PD, lactonase, phosphopentose isomerase, transketolase, transaldolase
G6PD, lactonase, phosphopentose epimerase, transketolase, transaldolase
G6PD, 6-phosphogluconate dehydrogenase, phosphopentose isomerase, phosphopentose epimerase, transketolase
G6PD, 6-phosphogluconate dehydrogenase, phosphopentose isomerase, phosphopentose epimerase, transaldolase
G6PD, 6-phosphogluconate dehydrogenase, phosphopentose isomerase, transketolase, transaldolase
G6PD, 6-phosphogluconate dehydrogenase, phosphopentose epimerase, transketolase, transaldolase
G6PD, phosphopentose isomerase, phosphopentose epimerase, transketolase, transaldolase
lactonase, 6-phosphogluconate dehydrogenase, phosphopentose isomerase, phosphopentose epimerase, transketolase
lactonase, 6-phosphogluconate dehydrogenase, phosphopentose isomerase, phosphopentose epimerase, transaldolase
lactonase, 6-phosphogluconate dehydrogenase, phosphopentose isomerase, transketolase, transaldolase
lactonase, 6-phosphogluconate dehydrogenase, phosphopentose epimerase, transketolase, transaldolase
lactonase, phosphopentose isomerase, phosphopentose epimerase, transketolase, transaldolase
6-phosphogluconate dehydrogenase, phosphopentose isomerase, phosphopentose epimerase, transketolase, transaldolase
G6PD, lactonase, 6-phosphogluconate dehydrogenase, phosphopentose isomerase, phosphopentose epimerase, transketolase
G6PD, lactonase, 6-phosphogluconate dehydrogenase, phosphopentose isomerase, phosphopentose epimerase, transaldolase
G6PD, lactonase, 6-phosphogluconate dehydrogenase, phosphopentose isomerase, transketolase, transaldolase
G6PD, lactonase, 6-phosphogluconate dehydrogenase, phosphopentose epimerase, transketolase, transaldolase
G6PD, lactonase, phosphopentose isomerase, phosphopentose epimerase, transketolase, transaldolase
G6PD, 6-phosphogluconate dehydrogenase, phosphopentose isomerase, phosphopentose epimerase, transketolase, transaldolase
lactonase, 6-phosphogluconate dehydrogenase, phosphopentose isomerase, phosphopentose epimerase, transketolase, transaldolase
G6PD, lactonase, 6-phosphogluconate dehydrogenase, phosphopentose isomerase, phosphopentose epimerase, transketolase, transaldolase Non-limiting examples of small molecule inhibitors that are specific to an enzyme in the PPP include 6-aminonicotinamide (6-AN) which inhibits the G6PD enzyme of the PPP, halogenated (fluorinated) D-hexoses (e.g. 2-Amino-2-deoxy-D-glucose-6-phosphate (D-glucosamine-6-phosphate)), glucosamine, cystamine (2,2'-Ditio-bis[ethylamine]), isoflurane, sevoflurane, diazepam, and 2-deoxyglucose.

In yet other embodiments, the PPP may be inhibited by an RNA interference (RNAi) agent that inhibits expression of an enzyme of the PPP. Methods of designing, generating and using an RNAi agent are known in the art. In some embodiments, the RNAi agent may be a short interfering RNA (siRNA). In general, a siRNA comprises a double-stranded RNA molecule that ranges from about 15 to about 29 nucleotides in length. The siRNA may be about 16-18, 17-19, 21-23, 24-27, or 27-29 nucleotides in length. In a preferred embodiment, the siRNA may be about 21 nucleotides in length. The siRNA may optionally further comprise one or two single-stranded overhangs, e.g., a 3' overhang on one or both ends. The siRNA may be formed from two RNA molecules that hybridize together or, alternatively, may be generated from a short hairpin RNA (shRNA) (see below). In some embodiments, the two strands of the siRNA may be completely complementary, such that no mismatches or bulges exist in the duplex formed between the two sequences. In other embodiments, the two strands of the siRNA may be substantially complementary, such that one or more mismatches and/or bulges may exist in the duplex formed between the two sequences. In certain embodiments, one or both of the 5' ends of the siRNA may have a phosphate group, while in other embodiments one or both of the 5' ends lack a phosphate group. In other embodiments, one or both of the 3' ends of the siRNA may have a hydroxyl group, while in other embodiments one or both of the 5' ends lack a hydroxyl group.

One strand of the siRNA, which is referred to as the "antisense strand" or "guide strand," includes a portion that hybridizes with the target transcript. In preferred embodiments, the antisense strand of the siRNA may be completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand may be substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, Wash.) and MISSION® siRNA (Sigma-Aldrich, St. Louis, Mo.). The siRNA may be enzymatically synthesized in vitro using methods well known to those of skill in the art. Alternatively, the siRNA may be chemically synthesized using oligonucleotide synthesis techniques that are well known in the art.

In other embodiments, the RNAi agent may be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure may also be called a stem-loop structure, with the stem being the duplex portion. In some embodiments, the duplex portion of the structure may be completely complementary, such that no mismatches or bulges exist in the duplex region of the shRNA. In other embodiments, the duplex portion of the structure may be substantially complementary, such that one or more mismatches and/or bulges may exist in the duplex portion of the shRNA. The loop of the structure may be from about 1 to about 20 nucleotides in length, preferably from about 4 to about 10 about nucleotides in length, and more preferably from about 6 to about 9 nucleotides in length. The loop may be located at either the 5' or 3' end of the region that is complementary to the target transcript (i.e., the antisense portion of the shRNA).

The shRNA may further comprise an overhang on the 5' or 3' end. The optional overhang may be from about 1 to about 20 nucleotides in length, and more preferably from about 2 to about 15 nucleotides in length. In some embodiments, the overhang may comprise one or more U residues, e.g., between about 1 and about 5 U residues. In some embodiments, the 5' end of the shRNA may have a phosphate group, while in other embodiments it may not. In other embodiments, the 3' end of the shRNA may have a hydroxyl group, while in other embodiments it may not. In general, shRNAs are processed into siRNAs by the conserved cellular RNAi machinery. Thus, shRNAs are precursors of siRNAs and are similarly capable of inhibiting expression of a target transcript that is complementary to a portion of the shRNA (i.e., the antisense portion of the shRNA). Those of skill in the art are familiar with the available resources (as detailed above) for the design and synthesis of shRNAs. An exemplary example is MISSION® shRNAs (Sigma-Aldrich).

In still other embodiments, the RNAi agent may be an RNAi expression vector. Typically, an RNAi expression vector may be used for intracellular (in vivo) synthesis of RNAi agents, such as siRNAs or shRNAs. In one embodiment, two separate, complementary siRNA strands may be transcribed using a single vector containing two promoters, each of which directs transcription of a single siRNA strand (i.e., each promoter is operably linked to a template for the siRNA so that transcription may occur). The two promoters may be in the same orientation, in which case each is operably linked to a template for one of the complementary siRNA strands. Alternatively, the two promoters may be in opposite orientations, flanking a single template so that transcription for the promoters results in synthesis of two complementary siRNA strands. In another embodiment, the RNAi expression vector may contain a promoter that drives transcription of a single RNA molecule comprising two complementary regions, such that the transcript forms a shRNA.

Those of skill in the art will appreciate that it is preferable for siRNA and shRNA agents to be produced in vivo via the transcription of more than one transcription unit. Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II may be used to drive expression of the one or more siRNA or shRNA transcription units. In some embodiments, tissue-specific, cell-specific, or inducible Pol II promoters may be used.

A construct that provides a template for the synthesis of siRNA or shRNA may be produced using standard recombinant DNA methods and inserted into any of a wide variety of different vectors suitable for expression in eukaryotic cells. Guidance may be found in Current Protocols in Molecular Biology (Ausubel et al., John Wiley & Sons, New York, 2003) or Molecular Cloning: A Laboratory Manual (Sambrook & Russell, Cold Spring Harbor Press, Cold Spring Harbor, N.Y., 3rd edition, 2001). Those of skill in the art also appreciate that vectors may comprise additional regulatory sequences (e.g., termination sequence, translational control sequence, etc.), as well selectable marker sequences. DNA plasmids are known in the art, including those based on pBR322, PUC, and so forth. Since many expression vectors already contain a suitable promoter or promoters, it may be only necessary to insert the nucleic acid sequence that encodes the RNAi agent of interest at an appropriate location with respect to the promoter(s). Viral vectors may also be used to provide intracellular expression of RNAi agents. Suitable viral vectors include retroviral vectors, lentiviral vectors, adenoviral vectors, adeno-associated virus vectors, herpes virus vectors, and so forth. In preferred embodiment, the RNAi expression vector is a shRNA lentiviral-based vector or lentiviral particle, such as that provided in MISSION® TRC shRNA products (Sigma-Aldrich).

The RNAi agents or RNAi expression vectors may be administered using methods well known to those of skill in the art. Guidance may be found in Ausubel et al., supra or Sambrook & Russell, supra, for example.

(c) Administration.

The methods of the present disclosure comprise administering an inhibitor of the PPP. Methods of administering can and will vary depending on the inhibitor to be administered. The inhibitor of the PPP may be administered orally, by inhalation spray, pulmonary, intranasally, rectally, buccally, subcutaneously, intramuscularly, intrasternally intravenously, intravaginally, intrauterinely, rectally, intradermally, transdermally (for instance see US 2006/0084604), or topically in dosage unit formulations containing conventional nontoxic pharmaceutically acceptable carriers, adjuvants, and vehicles as desired. Topical administration may also involve the use of transdermal administration such as transdermal patches or iontophoresis devices. Preferably, a method of the invention utilizes local administration, e.g. intrauterine or intravaginal administration.

Solid dosage forms for oral administration may include capsules, tablets, pills, powders, and granules. In such solid dosage forms, the PPP inhibitor may be combined with one or more adjuvants appropriate to the indicated route of administration. If administered per oral solid, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings. Tablets or capsules may be coated or otherwise compounded to provide a dosage form affording the advantage of prolonged action. For example, the tablet or capsule may comprise an inner dosage and an outer dosage component, the latter being in the form of an envelope over the former. The two components may be separated by an enteric layer which serves to resist disintegration in the stomach and permit the inner component to pass intact into the duodenum or to be delayed in release. A variety of materials may be used for such enteric layers or coatings, such materials including a number of polymeric acids and mixtures of polymeric acids with such materials as shellac, cetyl alcohol, and cellulose acetate as are known in the art.

Liquid dosage forms for oral administration may include aqueous solutions, suitably flavored syrups, oil suspensions and flavored emulsions with edible oils such as cottonseed oil, sesame oil, coconut oil, or peanut oil as well as elixirs and similar pharmaceutical vehicles. Liquid dosage forms for oral administration may also include pharmaceutically acceptable emulsions, solutions, suspensions, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally or intrathecally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above may also useful.

In some embodiments, the inhibitor of PPP is administered locally into the reproductive cavity of a female (intracavitary). Non-limiting examples of administering a pharmaceutical preparation into the reproductive cavity of a female may include intrauterine administration and intravaginal administration. A preparation comprising a PPP inhibitor to be administered into the reproductive cavity of a female may be a vaginal pill, a vaginal suppository, ointments, creams, gels, sprays, liquid reservoir patches, vaginal rings, pastes, a liquid preparation and an intrauterine device.

Other methods of formulating a PPP inhibitor are discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

The inhibitor of the PPP may be administered in combination with other contraceptives. Non-limiting examples of contraceptive agents that may be used in combination with the PPP inhibitor include agents of contragestion, spermicidal compounds, a diaphragm, a vaginal ring, androgenic agents, estrogens, progestins and combinations thereof.

Suitable androgenic agents that may be administered in combination with a PPP inhibitor include, but are not limited to: the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone.

Suitable estrogens that may be administered in combination with a PPP inhibitor include, but are not limited to: synthetic and natural estrogens such as: estradiol (i.e., 1,3,5-estratriene-3,17β-diol, or "β-estradiol") and its esters, including estradiol benzoate, valerate, cypionate, heptanoate, decanoate, acetate and diacetate; 17α-estradiol; ethynylestradiol (i.e., 17α-ethynylestradiol) and esters and ethers thereof, including ethynylestradiol 3-acetate and ethynylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens.

Suitable progestins that may be administered in combination with a PPP inhibitor include, but are not limited to: acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone.

The amount of PPP inhibitor to be administered will vary depending upon the subject, the compound, and the particular mode of administration. In some embodiments when the PPP inhibitor is DHEA, the PPP inhibitor may be administered intracavitary or orally at about 10, 20, 30, 40, 50, 60, 70, 80, 90, 100, 110, 120, 130, 140, 150, 160, 170, 180, 190, 200, 210, 220, 230, 240, or about 250 mg/day. In other embodiments when the PPP inhibitor is DHEA, the PPP inhibitor may be administered intracavitary or orally at about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or about 250 mg/day. In yet other embodiments when the PPP inhibitor is DHEA, the PPP inhibitor may be administered intracavitary or orally at about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80 mg/day. In other embodiments when the PPP inhibitor is DHEA, the PPP inhibitor may be administered intracavitary or orally at about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or about 110 mg/day. In additional embodiments when the PPP inhibitor is DHEA, the PPP inhibitor may be administered intracavitary or orally at about 110, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or about 140 mg/day. In still other embodiments when the PPP inhibitor is DHEA, the PPP inhibitor may be administered intracavitary or orally at about 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, or about 170 mg/day. In other embodiments when the PPP inhibitor is DHEA, the PPP inhibitor may be administered intracavitary or orally at about 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or about 200 mg/day. In yet other embodiments when the PPP inhibitor is DHEA, the PPP inhibitor may be administered intracavitary or orally at about 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 239, or about 240 mg/day.

In some embodiments when the PPP inhibitor is glucosamine, the PPP inhibitor may be administered intracavitary or orally at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or about 6 mg/day. In other embodiments when the PPP inhibitor is glucosamine, the PPP inhibitor may be administered intracavitary or orally at about 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.9, or about 1 mg/day. In yet other embodiments when the PPP inhibitor is glucosamine, the PPP inhibitor may be administered intracavitary or orally at about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or about 3 mg/day. In other embodiments when the PPP inhibitor is glucosamine, the PPP inhibitor may be administered intracavitary or orally at about 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or about 5 mg/day. In additional embodiments when the PPP inhibitor is glucosamine, the PPP inhibitor may be administered intracavitary or orally at about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or about 6 mg/day.

In some embodiments, when the PPP inhibitor is 6AN, the PPP inhibitor may be administered intracavitary or orally at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 25, 25, 26, 27, 28, 29, or about 30 mg/day. In other embodiments, when the PPP inhibitor is 6AN, the PPP inhibitor may be administered intracavitary or orally at about 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.9, or about 1 mg/day. In yet other embodiments, when the PPP inhibitor is 6AN, the PPP inhibitor may be administered intracavitary or orally at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 mg/day. In additional embodiments, when the PPP inhibitor is 6AN, the PPP inhibitor may be administered intracavitary or orally at about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or about 4 mg/day. In still other embodiments, when the PPP inhibitor is 6AN, the PPP inhibitor may be administered intracavitary or orally at about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or about 5 mg/day. In other embodiments, when the PPP inhibitor is 6AN, the PPP inhibitor may be administered intracavitary or orally at about 4, 4.1, 4.2, 4.3, 4.4, 4.5, 4.6, 4.7, 4.8, 4.9, 5, 6, 7, 8, 9, or about 10 mg/day. In yet other embodiments, when the PPP inhibitor is 6AN, the PPP inhibitor may be administered intracavitary or orally at about 5, 6, 7, 8, 9, 10, 11, 12, 13, 14, 15, 16, 17, 118, 19 or about 20 mg/day. In other embodiments, when the PPP inhibitor is 6AN, the PPP inhibitor may be administered intracavitary or orally at about 15, 16, 17, 118, 19, 20, 21, 22, 23, 25, 25, 26, 27, 28, 29, or about 30 mg/day.

Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

The PPP inhibitor may be administered to a female mammal. Non-limiting examples of mammals that may benefit from administering a PPP inhibitor may be a rodent, a human, a livestock animal, a companion animal, a laboratory animal, or a zoological animal. In one embodiment, the mammal may be a lab animal. Non-limiting examples of a lab animal include a rabbit, a mouse, a guinea pig, a hamster, or a rat. In another embodiment, the mammal may be a rodent, e.g. a mouse, a rat, a guinea pig, etc. In yet another embodiment, the mammal may be a livestock animal. Non-limiting examples of suitable livestock animals may include pigs, cows, horses, goats, sheep, llamas and alpacas. In another embodiment, the mammal may be a companion animal. Non-limiting examples of companion animals may include pets such as dogs, cats, rabbits, and birds. In still yet another embodiment, the mammal may be a zoological animal. As used herein, a "zoological animal" refers to an animal that may be found in a zoo. Such animals may include non-human primates, large cats, wolves, and bears. In an exemplary embodiment, the mammal may be a human.

The inhibitor of PPP may be administered continually as long as pregnancy is not desired. Alternatively, the PPP inhibitor may be administered before, during or after decidualization, or a combination thereof.

EXAMPLES

Introduction for Examples 1-6

Recurrent pregnancy loss is a common problem which affects about 2-4% of couples trying to conceive and the etiologies remain largely unknown. The success of a pregnancy is determined by the completion of a number of sequential processes with proper implantation of the embryo being one of the initial key factors. Failure of the endometrium to properly differentiate towards a receptive state can be the source of early pregnancy loss even when the embryo is properly developed. One of the key processes in uterine preparation for embryo receptivity is the differentiation of endometrial stromal cells (ESCs) into decidual cells, which are crucial for embryo survival through the early stages of implantation. While in the mouse and most other species, decidualization is initiated by the presence of the blastocyst, in the human this process is independent of the embryo and begins in the secretory phase of the cycle, prior to fertilization and pregnancy itself.

Glucose utilization in the endometrial stroma is upregulated at the time of decidualization and implantation failure may be a result of improper glucose uptake and/or metabolism in ESCs. Differentiation itself is a very metabolically demanding event, and any alterations in glucose uptake or its subsequent metabolism may lead to aberrant or incomplete decidualization and a failure to support further embryo development. Since ESCs differentiate into decidual cells, which are very distinct both morphologically and functionally, it is likely that they have completely different metabolic needs from the undifferentiated stroma. The efficiency of the uptake is determined by a family of facilitative glucose transporters (GLUTs) and several of these transporters are already known to be present in the stroma. The expression of at least one of them, GLUT1, is strongly upregulated during decidualization, leading to increased glucose uptake. However, very little data regarding the subsequent metabolic fates of glucose in this tissue are available. Upon entry into the cells, glucose has several metabolic fates. i) It can be processed through oxidation in glycolysis, followed by the Krebs cycle and the respiratory chain in the mitochondria to provide energy as ATP. ii) Glucose can also be stored as glycogen or iii) it can enter the pentose phosphate pathway, which produces NADPH for biosynthesis of cholesterol, fatty acids and reduced glutathione, and ribose 5-phosphate for biosynthesis of nucleotides. Each of these pathways is catalyzed by a number of enzymes, which can be regulated in a tissue specific and temporal pattern.

Several groups have recently shown that glucose utilization can be hormonally regulated in various cell types. First evidence for this came from the aromatase knockout (ArKO) and estrogen receptor knockout (ERKO) mice, which have a number of whole-body metabolic defects, such as hyperglycemia, insulin-resistance, and increased adiposity. Since both of these mouse models lack estrogen signaling, this suggests that the observed diabetic phenotype is the result of aberrant hormonal homeostasis. Further research has primarily been focused on the regulation of glucose uptake via transcriptional regulation of GLUTs by steroid hormones in various tissues. In addition, there are a number of human pathological states that provide evidence for hormonal regulation of glucose uptake. Women with PCOS and gestational diabetes mellitus have decreased levels of GLUT4 (the main human insulin-stimulated glucose transporter) expression in adipose tissue. GLUT1 expression is directly upregulated by progesterone in murine ESCs, and this consequently increases glucose uptake into these cells. A few studies have focused on the metabolic pathway disturbances by hormones. Estrogens have been implicated in the regulation of glucose transport, glycolysis, Krebs cycle, and the respiratory chain and some androgens such as DHEA are known to inhibit the pentose phosphate pathway. However, most of these studies remain correlative, lacking mechanistic evidence, and there are no studies regarding the downstream metabolic fates of glucose once it has been taken up into ESCs.

The Examples presented below detail the role of glucose utilization in ESCs and the mechanisms which may be responsible for perturbations in the glucose homeostasis required for differentiation of ESCs into the decidual cells capable of supporting further embryo development are elucidated. The data demonstrate that decidualization is dependent upon adequate levels of glucose taken up and metabolized primarily through the pentose phosphate pathway. Additionally, the data demonstrate that PPP inhibitors prevent proliferation of ESCs and that this effect is independent of their effects of decidualization. Taken together, these data specifically demonstrate that adequate glucose flux through the PPP is required for development of the stromal compartment in both phases of the menstrual cycle, the proliferative and secretory.

Example 1

Decidualization is Dependent Upon Sufficient Glucose In Vitro

Figure 1B:
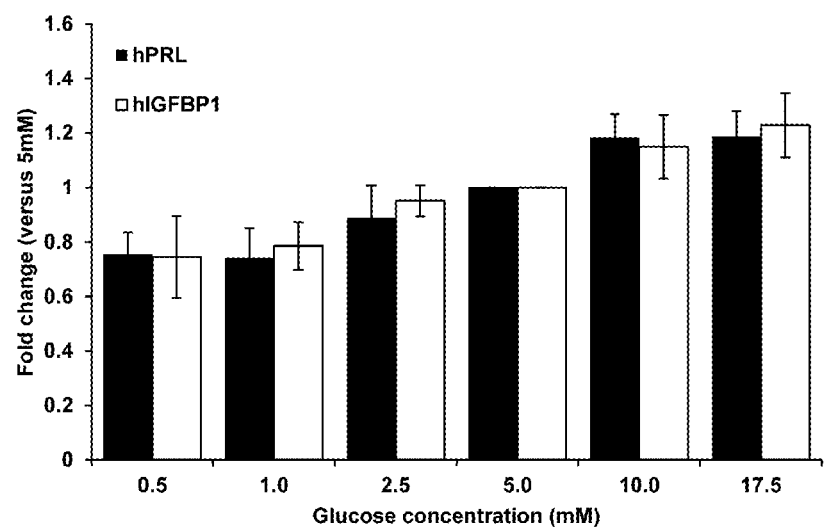

Previous data have shown that GLUT1 protein expression and glucose uptake increase during decidualization in vitro in both the mouse and human ESCs. These results suggest that decidualization might be a glucose-dependent process. Therefore, a previously established primary cell culture system was used to analyze the levels of Prp expression in ESCs cultured under variable glucose concentrations in vitro. Prp is a well established murine decidualization marker. Murine endometrial stromal cells (mESCs) were isolated from mice at 4 days post coitum (dpc) and cultured in the presence of estrogen (E2) and progesterone (P4) for 72 h with glucose concentrations ranging from 0.5-17.5 mM. Decidualization was monitored via Prp mRNA levels, and normalized to the level detected in the cells incubated in the presence of 5 mM glucose, which is the concentration of glucose normally found in murine serum (FIG. 1a). In parallel experiments, human ESCs (hESCs) were cultured for 9 days in the presence of MPA and cAMP under the same range of glucose concentrations. Decidualization was monitored using Prl and Igfbp1 mRNA as markers (FIG. 1b). In both systems, expression of decidualization markers significantly decreased when glucose levels were below 2.5 mM. These data suggested that an adequate glucose concentration is required for proper ESC differentiation into decidual cells.

Example 2

Glucose Metabolism Through the Pentose Phosphate Pathway is Essential for Esc Decidualization In Vitro Since differentiation of ESCs into decidual cells is severely diminished when the cells are cultured in insufficient glucose (FIG. 1) or when uptake is hindered by Glut1 knockdown (data not shown), experiments were focused on defining which metabolic pathway(s) were activated during decidualization. Glucose, upon entering the cell, is converted to glucose-6-phosphate (G6P) by hexokinase and then may be utilized in one of three major pathways: i) G6P may be oxidized through glycolysis, and the resulting pyruvate fed into the TCA cycle, or ii) it may be stored as glycogen. iii) Another pathway for glucose is to utilize it in the pentose phosphate pathway, which regenerates NADPH and also produces ribose-5-phosphate. Experiments were aimed at distinguishing which of these pathways is essential for the differentiation of ESCs.

Figure 2A:
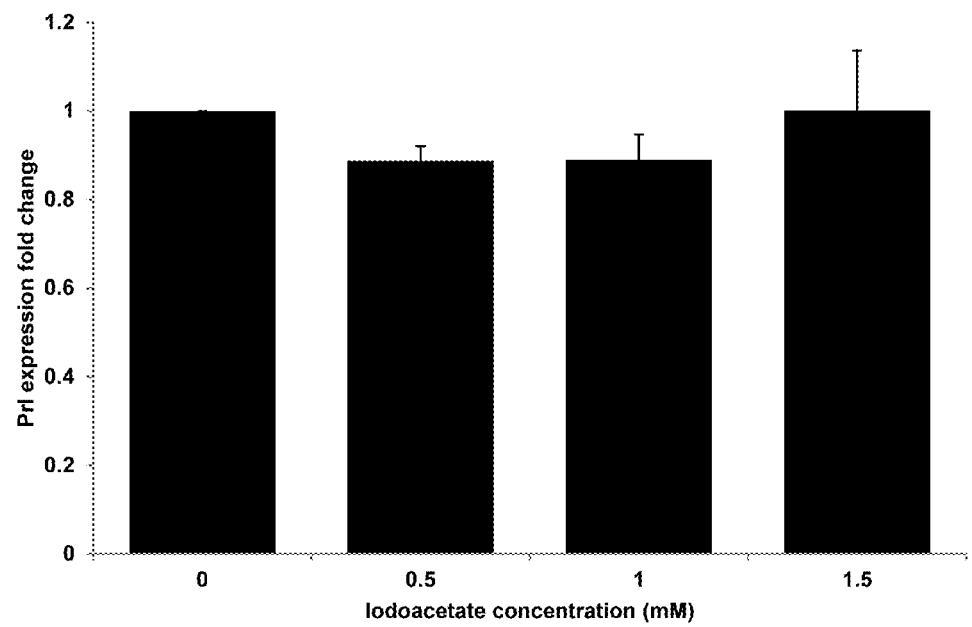
FIG. 2A-B depicts histograms of marker expression and percent glycolytic activity in the presence of iodoacetate. (A) Expression of decidualization marker, Prl, in human ESCs cultured in the presence of Iodoacetate, an inhibitor of GAPDH. (B) Flux through glycolysis represented by $^3H_2O$ production ($H_2O$ produced from the 5th hydrogen of glucose is a product of glycolysis) in ESCs exposed to different concentrations of IA.
Figure 2B:
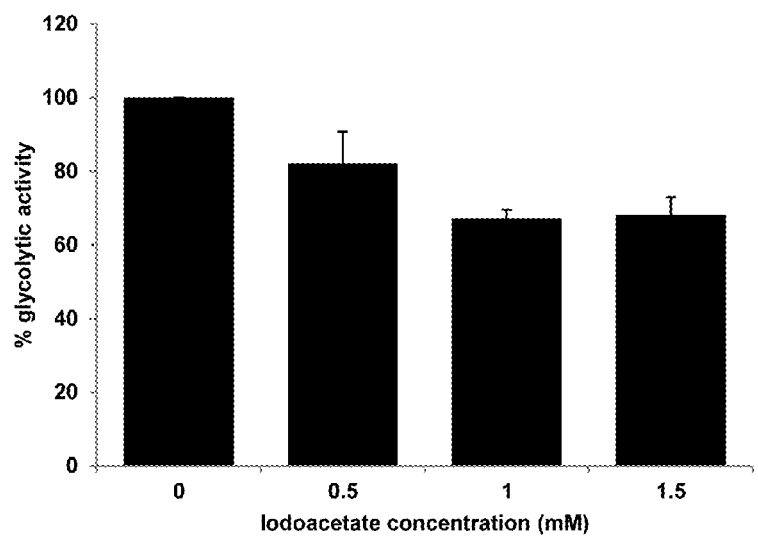

In order to assess the significance of glycolysis being fully functional, a glyceraldehydes-3-phosphate dehydrogenase (GAPDH) inhibitor, Iodoacetate (IA) was used. ESCs were cultured under decidualizing conditions in the presence of IA at the concentrations indicated in FIG. 2. In order to confirm inhibition of glycolysis, human immortalized ESCs were incubated in the presence of 5-$^3$H-glucose for four hours and the amount of $^3H_2O$ production ($H_2O$ produced from the 5th hydrogen of glucose is a product of glycolysis) in ESCs exposed to different concentrations of IA was measured (FIG. 2b). Flux of glucose through glycolysis was reduced by 40% and plateaued at this reduction with 1 µM and 1.5 µM concentrations of IA. Higher concentration of IA (starting with 2 µM) induced cell death within 24 hr of administration (data not shown). Decidualization was not affected by IA at any concentration used, which were below the toxic threshold, as assessed by Prl marker expression (FIG. 2a). This was suggestive that full function of glycolysis was not essential for decidualization or human ESCs, however, at least 50% activity of the pathway is essential for cell viability.

Figure 3A:
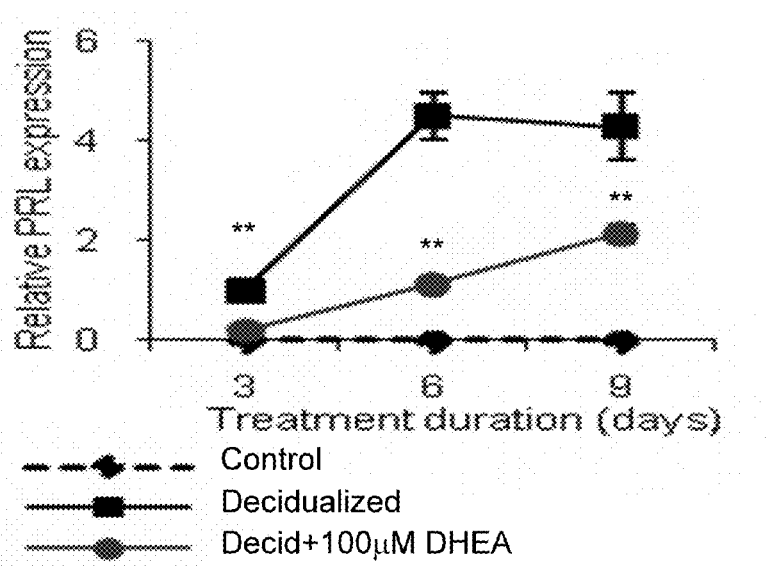
FIG. 3A-G depicts data showing that DHEA inhibits decidualization of ESCs in vitro. (A and B) 100 mM DHEA decreased the expression levels of both PRL and IGFBP1 starting as early as day three and continuing through day 9 in immortalized human ESCs. A morphological change is observed between the control (C) and decidualized (D) ESC-Ts as then cytoplasm increases and the cells lose their fibroblastic phenotype. When exposed to DHEA, the decidualizing ESC-Ts retain their spindle shape and resemble the undecidualized controls (E). (F) Expression of Prp is used to quantify extent of decidualization in murine ESCs (G) Prl and Igfbp1 are used to quantify decidualization in human primary ESCs. Values are a mean of at least 3 independent experiments+/−SEM. *, $p<0.05$ and **, $p<0.01$ compared to decidualized sample.
Figure 3B:
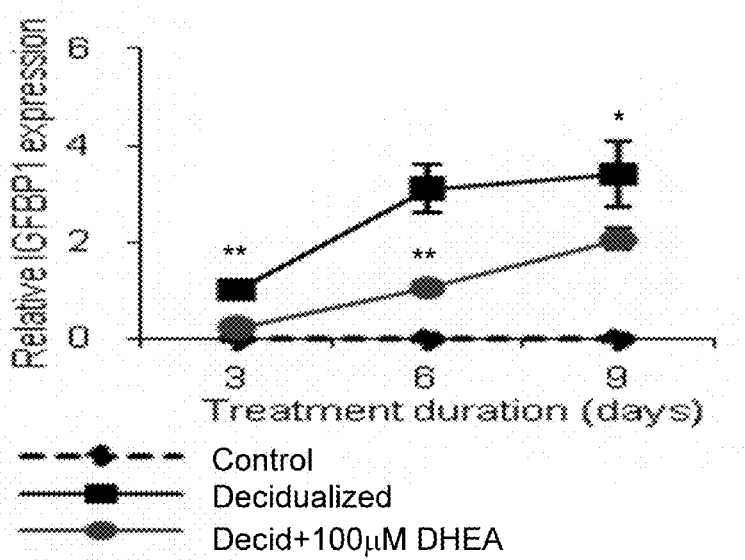
Figure 3C:
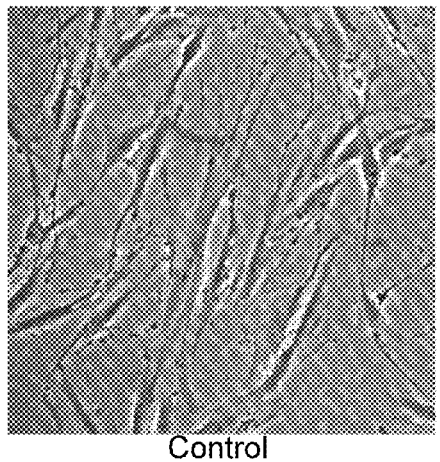
Figure 3D:
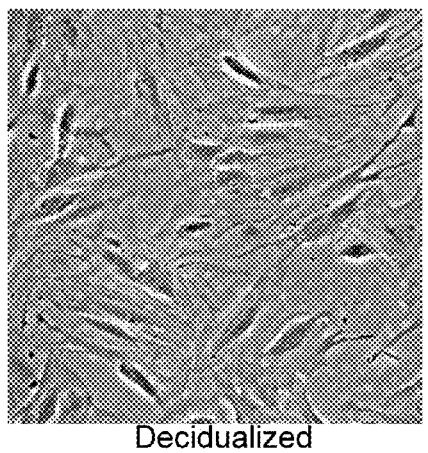
Figure 3E:
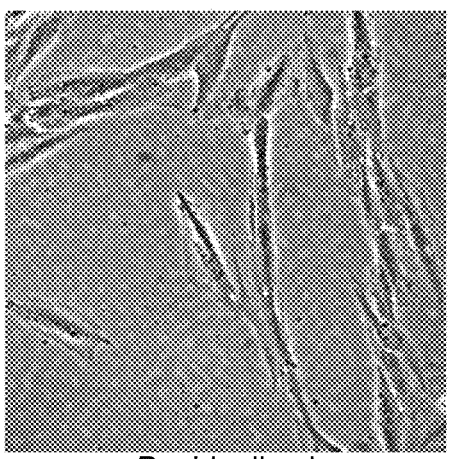

Next, DHEA, a potent non-competitive inhibitor of the rate limiting enzyme of the PPP, glucose-6-phosphate dehydrogenase (G6PD) was used to assess whether activity of this pathway is essential for ESC decidualization. Decidualization in human cells was monitored by measuring the mRNA expression of two decidualization markers, PRL and IGFBP1. In ESC-T cells, the expression of both markers was already 5-fold lower by day 3 of in vitro culture in the presence of 100 mM DHEA compared to cells receiving only the differentiation media (FIGS. 3A and B). The expression of both markers continued to lag behind in cells treated with DHEA compared to the normally differentiating ESC-Ts throughout the full 9 days of in vitro decidualization. Representative images in FIG. 3 present the morphological changes observed during decidualization of ESC-Ts in vitro. The undecidualized control ESC-Ts are elongated and have a fibroblast-like morphology, with little cytoplasm (FIG. 3C). Upon administration of differentiation media, the cells differentiate into a characteristic rounded shape with a prominent expansion of the cytoplasm (FIG. 3D). When the decidualizing ESC-T cultures are additionally exposed to 100 mM DHEA the morphological progression is halted and the cells sustain the fibroblast-like phenotype of undifferentiated cultures (FIG. 3E).

Figure 3F:
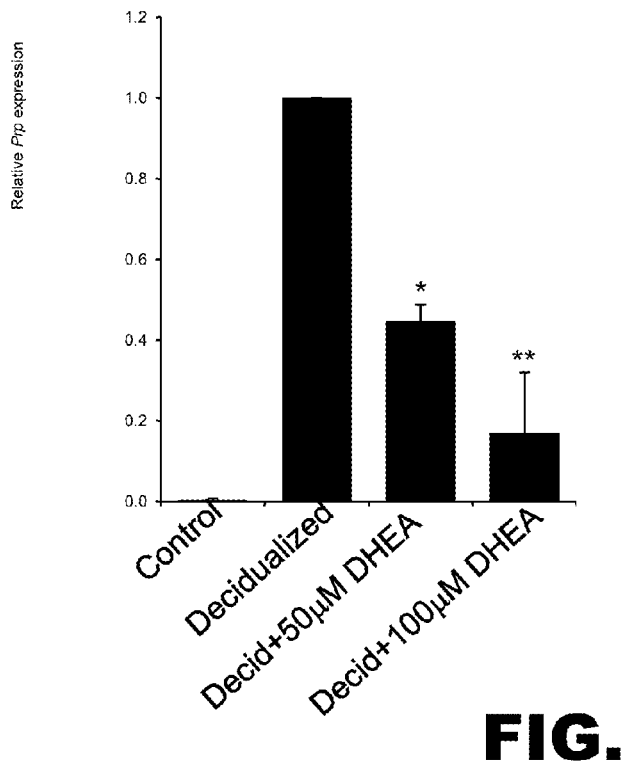
Figure 3G:
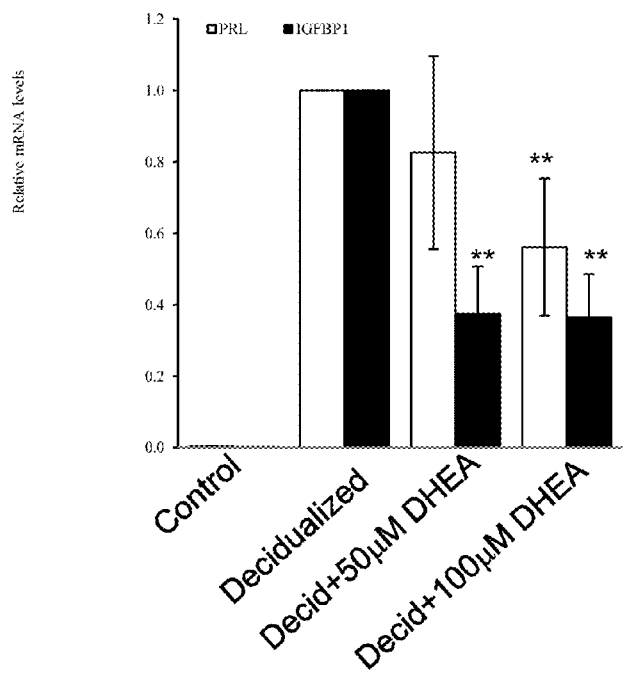

In order to confirm that this is not a side effect of ESC immortalization with telomerase overexpression in this human cell line, the effect of DHEA on decidualization of primary ESC cultures from mouse and human uteri was also investigated. Murine ESCs were isolated from the gravid uterus at 4 days post coitus and cultured in vitro for 3 days to induce decidualization as described in the Methods. Decidualization was assessed by monitoring the expression of a murine decidualization marker mRNA, Prp, which decreased upon addition of DHEA in a concentration-dependent manner (FIG. 3F). The human primary ESCs were isolated from uteri following hysterectomy for benign disease as outlined in the Methods and cultured in decidualization media for 9 days. As described above for murine cells, expression of PRL and IGFBP1 also decreased in a concentration dependent manner upon DHEA treatment (FIG. 3G). Taken together, these experiments suggested that DHEA inhibits decidualization of ESCs derived from both human and mouse and the lag in differentiation of human ESC-T cells may be observed as early as day 3 of the in vitro culture.

Figure 4A:
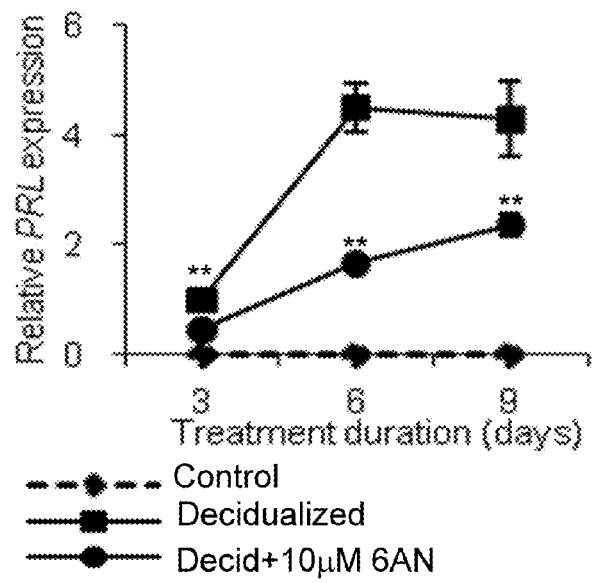
FIG. 4A-D depicts data showing that 6-Aminonicotinamide inhibits decidualization of ESCs in vitro. (A and B) Expression of decidualization markers, PRL and IGFBP1, was used to monitor the extent differentiation in immortalized human ESC-Ts through 9 days of in vitro culture. (D) Expression of PRL and IGFBP1 mRNA in primary human ESC cultures following 9 days of in vitro culture with and without 6AN. (C) Expression of murine decidualization marker, Prp, in primary mouse ESCs after 3 days of in vitro culture.
Figure 4B:
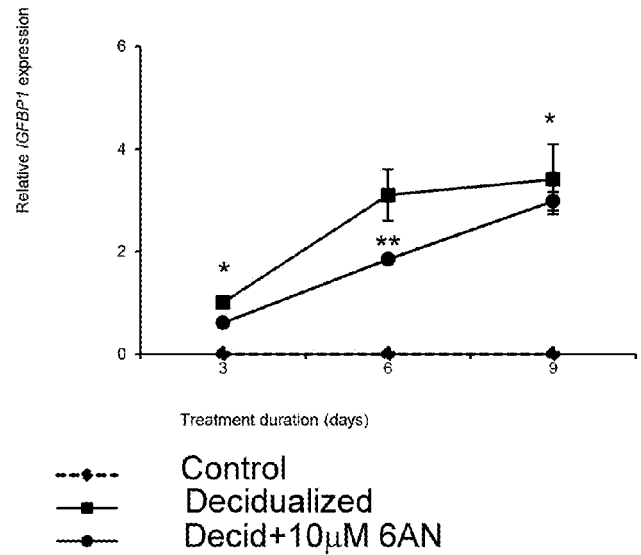
Figure 4C:
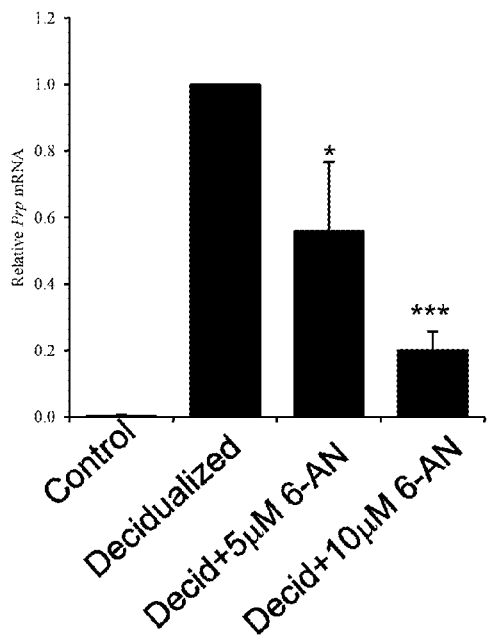
Figure 4D:
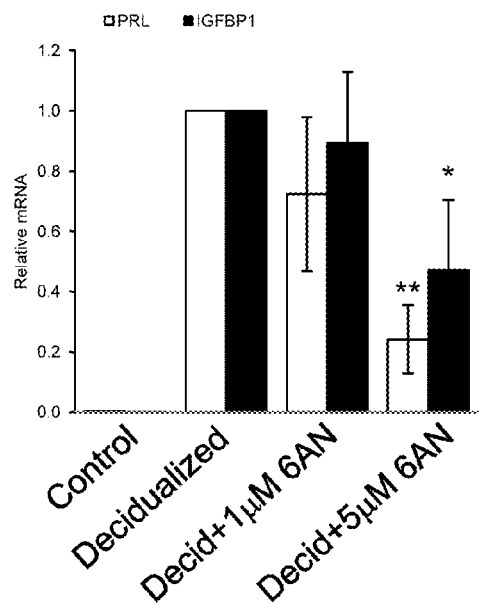

In order to directly demonstrate that DHEA prevents adequate ESC decidualization by inhibiting the PPP, the experiment was repeated using a more specific, synthetic inhibitor of the PPP, 6-aminonicotinamide (6AN). This NADP+ analog inhibits two enzymes in the PPP, G6PD and 6GPDH, which utilize NADP+ and convert it into NADPH. At a concentration of 10 µM, 6AN showed remarkably similar results to DHEA. It inhibited the expression of PRL and IGFBP in ESC-T cells from day 3 to day 9 in culture (FIGS. 4A and B). It also decreased Prp expression in primary murine ESCs and the expression of both human decidualization markers in primary human ESC cultures in a concentration-dependent manner (FIGS. 4C and D).

Figure 5A:
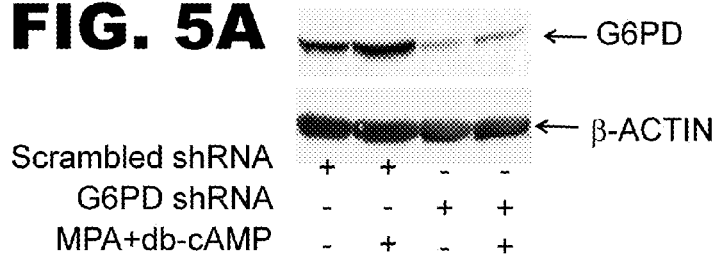
FIG. 5A-C depicts knockdown of G6PD and effects of G6PD knockdown on decidualization. (A) Protein expression of G6PD. (B) G6PD mRNA expression. (C) Effects of G6PD knockdown on decidualization in vitro. Prl and Igfbp1 were used to quantify decidualization in human ESCs.
Figure 5B:
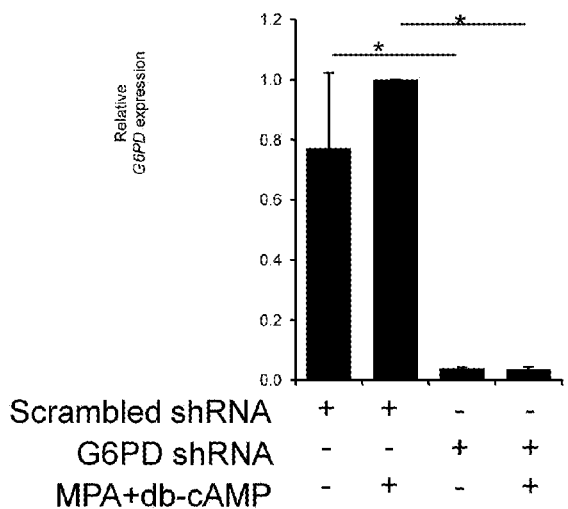
Figure 5C:
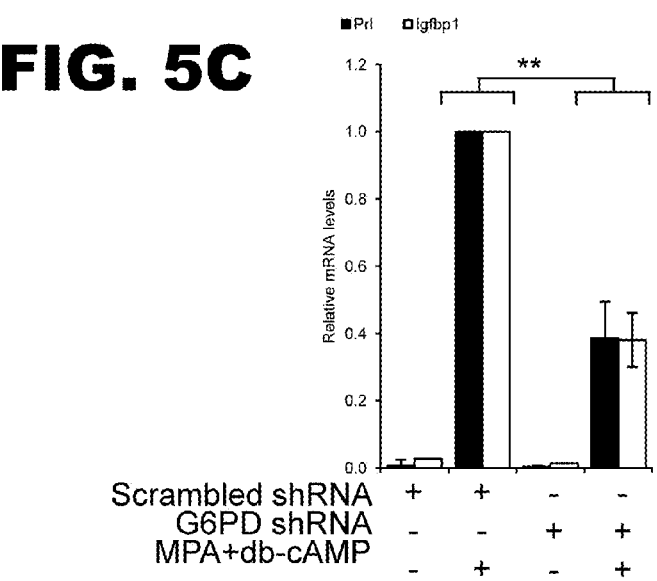

To decidedly implicate the PPP in the process of decidualization, G6PD was knocked down in vitro using specific shRNAs. Knockdown of G6PD had a negative effect on the process of decidualization because the decidual markers Prl and Igfbp1 were expressed at lower levels by day 4 of decidualization (FIG. 5).

These results unambiguously demonstrate that during decidualization, less glucose enters glycolysis and the TCA cycle, while flux through the PPP increases. When 6-AN is added at a concentration that prevents decidualization in vitro, there is a direct effect on the amount of glucose entering the PPP, but not the TCA cycle.

Example 3

Glucose Metabolism in hESCs In Vitro

Figure 6A:
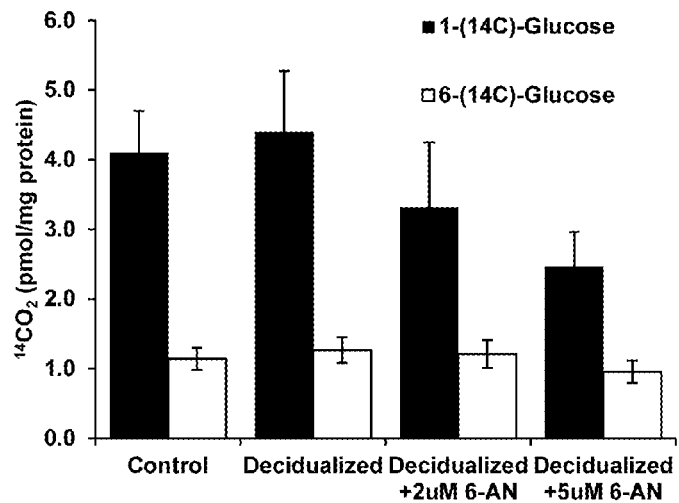
FIG. 6A-C depicts measurements of glucose flux under various conditions. (A) Effects of pentose phosphate pathway inhibitor, 6-AN on glucose flux in vitro. 1-($^{14}$C)-glucose is converted to $^{14}CO_2$ via the glycolytic/TCA and the pentose phosphate pathways, while the 6-($^{14}$C)-glucose is converted to $^{14}CO_2$ exclusively via glycolysis and the TCA cycle. (B) Ratio of 1-C radiolabled glucose flux to 6-C radiolabled glucose flux in vitro. (C) Tritium labeled glucose flux.
Figure 6B:
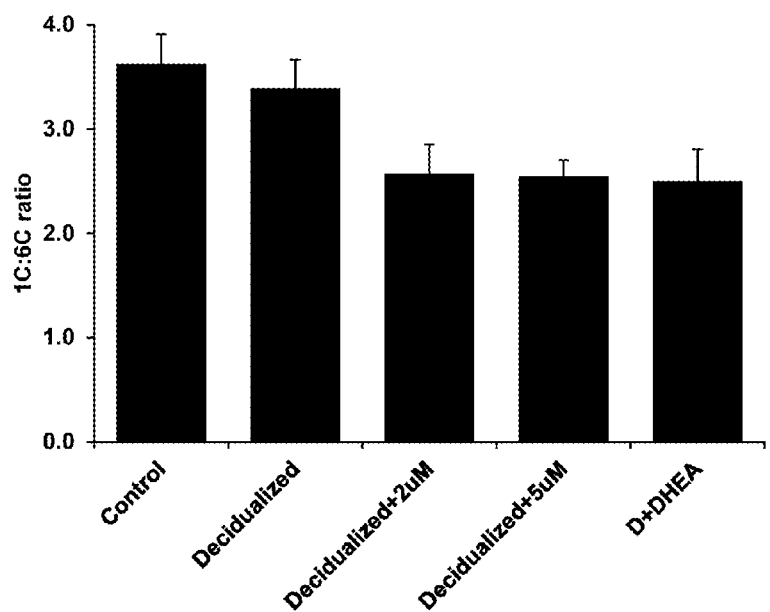
Figure 6C:
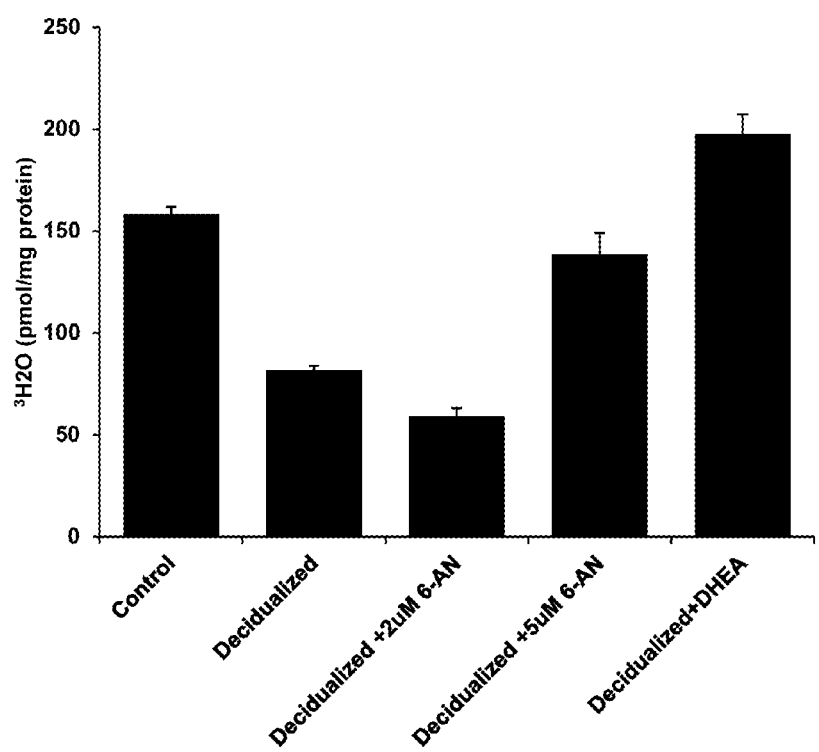

Having found that the inhibition of PPP reduces decidualization, the next experiments were directed to determine whether the flux of glucose through this pathway is increased or becomes more preferential during the ESC decidualization. For these experiments, hESCs immortalized via overexpression of telomerase (hESC-Ts) were used. These cells have been shown to be an adequate experimental model for ESC decidualization studies, having the same induction of decidualization marker (Prl and Igfbp1) expression. The response of these cells to PPP inhibitors was also tested in order to confirm their similar dependence on the pathway for differentiation. In order to determine glucose flux through the various metabolic pathways in ESCs the metabolic fates of $1-^{14}C$—, $6-^{14}C$—, and $5-^{3}H$-glucose was followed. hESC-Ts were incubated for 3 h with one of the radiolabeled glucoses and production of $^{14}CO_2$ or $^{3}H_2O$ was compared between the four treatment groups, control, decidualized, and decidualized with 2 μM or 5 μM 6-AN (FIG. 6). Glucose labeled at the C-1 position was metabolized equally in the control and decidualized hESC-Ts, but was lower in the decidualized cells exposed to 6-AN in a concentration dependent manner. This was an indication that the flux through the TCA cycle or PPP was decreased in the inhibitor-treated ESCs. In contrast, the metabolism of the 6-C was equal between the control and decidualized hESC-Ts, and was not affected by 6-AN, indicating that the TCA cycle specifically was down-regulated when 6-AN is present in the media. Therefore, inhibiting G6PD with 6-AN has no effect on TCA flux, but directly lowers the metabolism of glucose through PPP. The ratio of 1-C:6-C, which summarizes the relative preference of the PPP, can then be seen as decreasing in the presence of the inhibitor 6-AN.

Importantly, the $5-^{3}H$ labeled glucose showed the greatest glycolytic flux (which does not enter the TCA) in the untreated, control, samples, and lowest in the decidualized, but returned almost to the same levels as the control upon addition of 5 μM 6-AN. This indicates an increase in the amount of glucose entering glycolysis without continuing into the TCA cycle, possibly being converted into lactate. This seems to be a direct effect of decidualization itself because the 6-AN inhibitor, which does not act on glycolysis but prevents decidualization, causes these values to return to baseline (FIG. 6).

Example 4

DHEA Inhibits Decidualization In Vivo

Figure 7A:
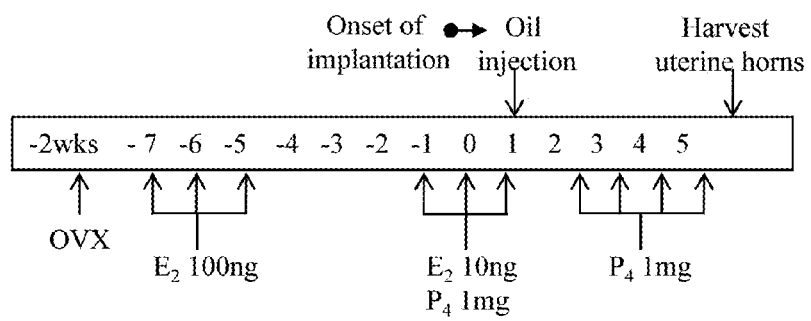
FIG. 7A-H depicts the effects of acute DHEA administration at the time of implantation on the decidualization reaction in vivo. (A) The time course of the experiment is outlined. DHEA (2 mg/100 kg bw/day) was administered beginning on day −2. (B) Uteri from two representative mice in each treatment group, control and DHEA, are shown. (C) The mass of deciduoma and control uterine horns is quantified for control and DHEA-treated mice. (D) Protein expression of Bmp2 is used to assess decidualization. (E) Representative cross section of the uterine horns stained with hematoxylin and eosin. Serum levels of (F) DHEA, (G) estradiol and (H) progesterone are shown. *, $p<0.001$.
Figure 7B:
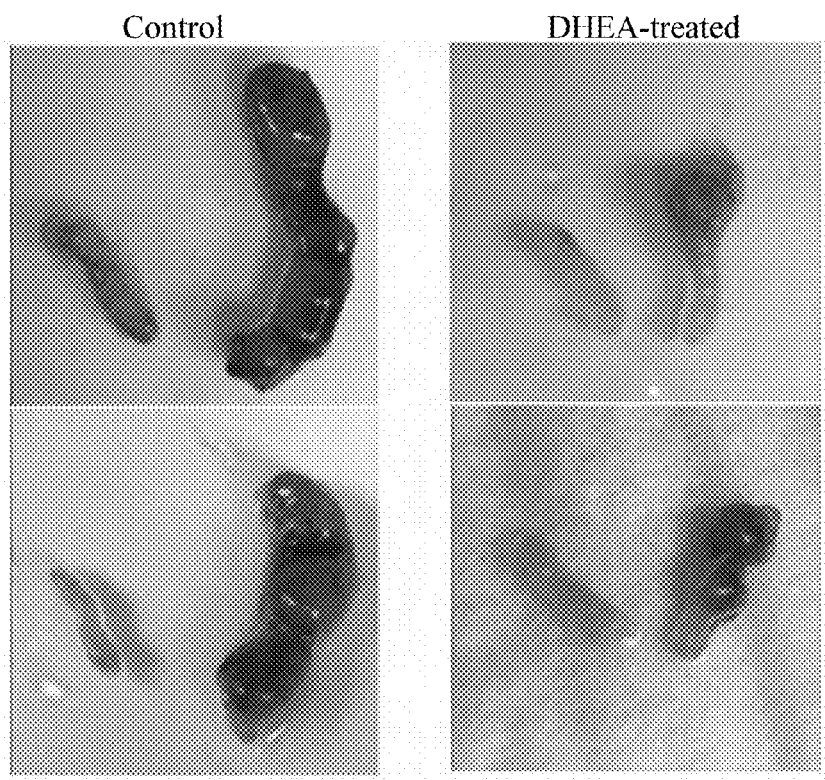
Figure 7C:
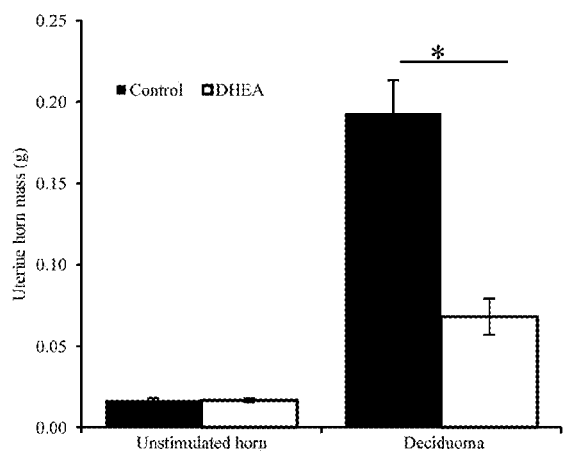
Figure 7D:
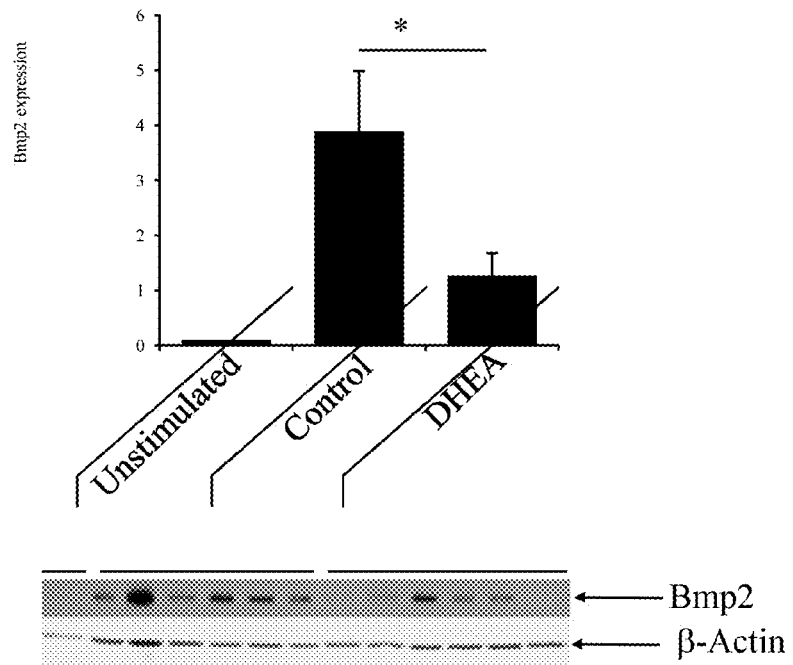
Figure 7E:
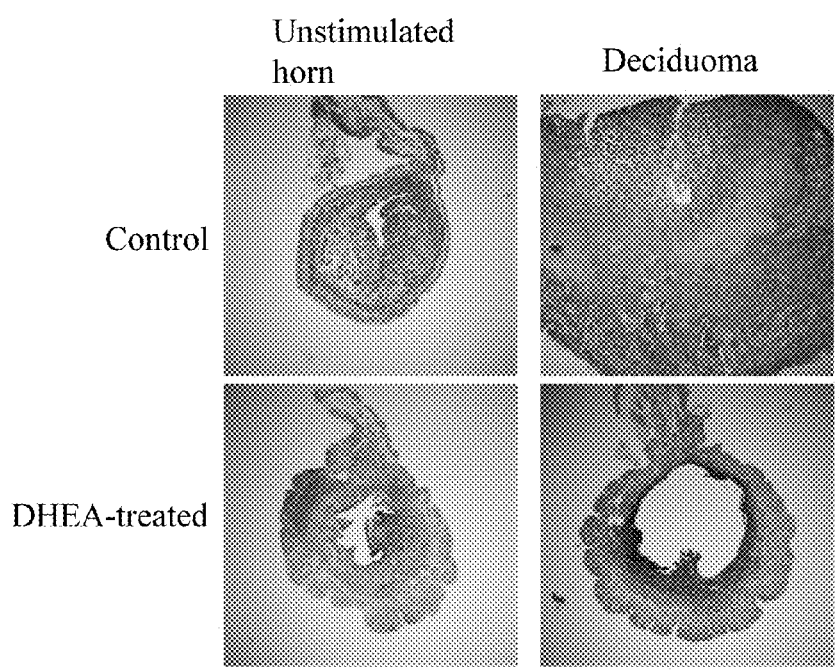
Figure 7F:
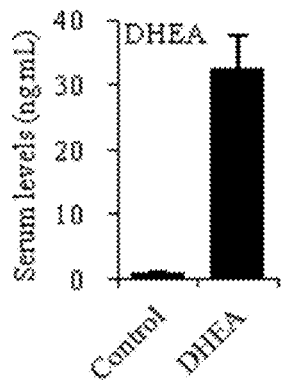
Figure 7G:
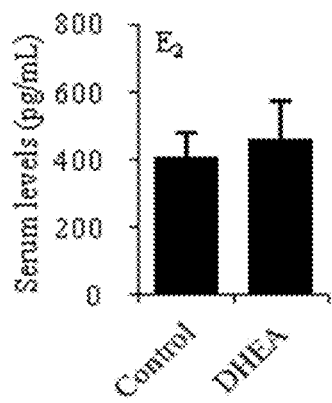
Figure 7H:
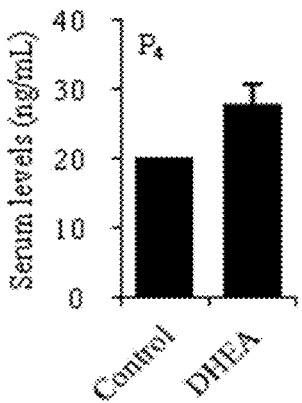

The in vitro experiments do not necessarily reflect the processes as they would happen in vivo. Therefore, to further demonstrate biological significance of the above data and confirm the effects of DHEA on G6PD and subsequent PPP inhibition on the decidualization process, a previously described mouse model of induced decidualization was employed. This induced deciduoma model allowed the study of the effect of increased DHEA on implantation independently of embryo development and ovarian function. Female mice 6-8 weeks of age were ovariectomized and rested for 2 weeks. They then received a regiment of $E_2$ and $P_4$, as shown in FIG. 7A, in order to sensitize the uterus to a decidualization-inducing stimulus. At day 2 before induction, the experimental mice also began receiving DHEA at 2 mg/100 g of body weight. The control mice received no DHEA. At day 0, one uterine horn in each animal was subjected to a physical stimulus, 100 μL sesame seed oil injection, to induce a deciduoma. The second horn was left as the unstimulated internal control for each mouse. Day 0 in this case is equivalent to the day of embryo implantation in a physiological mouse pregnancy, which is 4 days post coitus. Five days after the oil injection, uterine horns were dissected out. First the gross anatomies of the uteri were assessed. Representative tissues from two mice in each treatment group are shown (FIG. 7B). While the control mice demonstrate a robust deciduoma formation, the DHEA-treated mice had a weak, if any, deciduoma formation along the stimulated uterine horn. Further assessment was conducted by measuring the uterine mass, which revealed a ~3-fold decrease in the decidual response of uteri from the DHEA-treated animals compared to controls (FIG. 7C). Protein was isolated from all uterine horns in order to measure the expression of a well-established decidualization protein marker, Bmp2. Western blot analysis of whole tissue protein extracts showed a 3-fold decrease in Bmp2 protein induction in the deciduomas of the DHEA-treated mice compared to control mice (FIG. 7D). Bmp2 expression was almost undetectable in the unstimulated uterine horns. Morphological examination of uterine cross sections revealed a drastic increase in the number of decidual cells and in the size of the stromal compartment of stimulated horns from the control mice. In contrast, the stimulated uterine horns of DHEA-treated mice had no decidual cells and the size of the stromal compartment was indistinguishable from that of the control horn (FIG. 7E). In the same line of experiments, the serum hormone levels were also measured to confirm that findings were strictly the result of increased levels of DHEA. As predicted, serum DHEA levels, measured on day +5, were significantly higher in the DHEA-treated group than in the control mice (0.93 ng/ml vs 32.59 ng/ml, respectively), while the serum levels of $E_2$ and $P_4$ were equal in each treatment group (FIG. 7F). These results were in strong agreement with the in vitro data and clearly demonstrated that DHEA inhibits decidualization in vivo and that this outcome is independent of DHEA effects on embryo development and ovarian steroid synthesis.

Figure 8A:
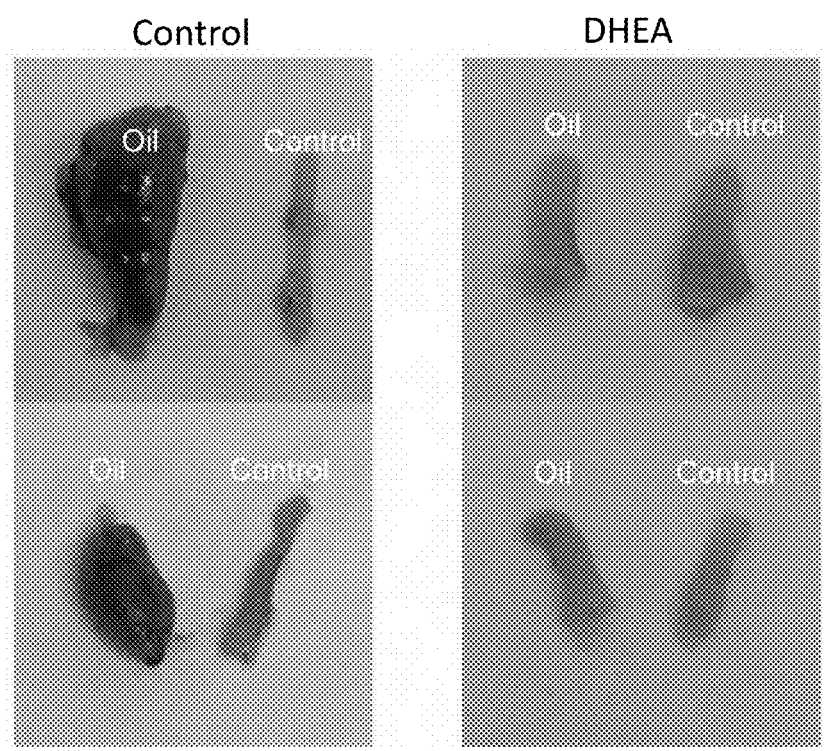
FIG. 8A-C depicts the effects of chronic DHEA administration on the decidualization reaction in vivo. Mice received chow supplemented with 0.6% DHEA by mass. (A) Representative uterine horns from control and DHEA treated mice. The horn on the right did not receive a physical stimulus to initiate decidualization and was the internal control in each mouse. The horn pictured on the left received the physical stimulus of an oil injection to initiate deciduoma formation. (B) Uterine horn mass is used to quantify extent of decidualization in vivo. (C) Percent body fat in mice on a high DHEA diet versus control.
Figure 8B:
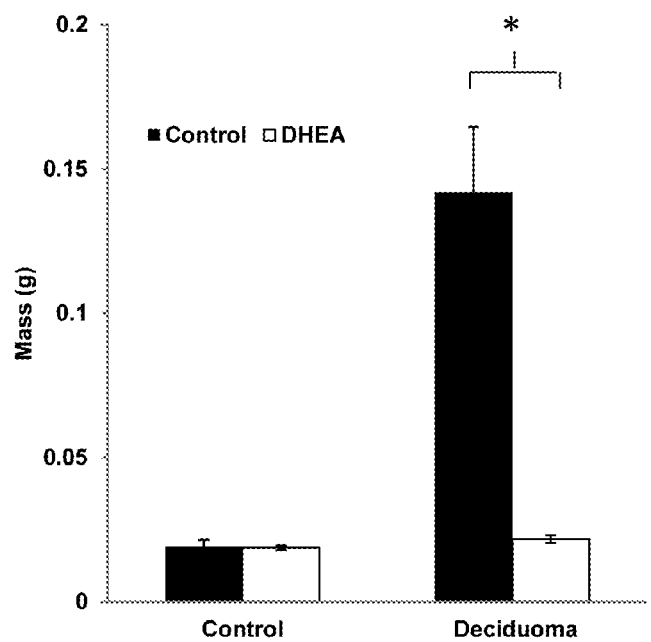
Figure 8C:
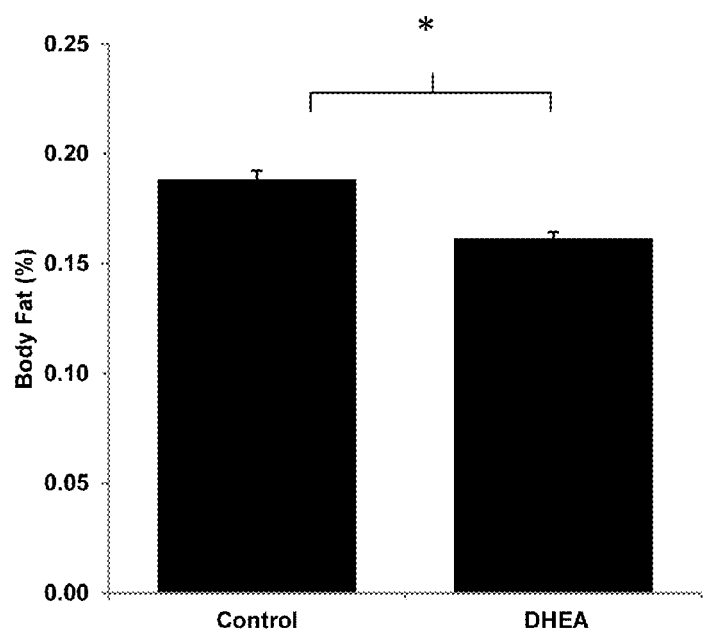

Decidualization in vivo under chronically elevated levels of DHEA was also tested. The ovariectomy mouse model described above was used with the following changes: DHEA was administered orally (0.6% supplementation in regular chow diet) starting on the day of ovariectomy. The mice were on the diet for 2 weeks prior to the beginning of the hormone regiments described in FIG. 7A. In FIG. 8A, representative uterine horns are shown from control mice (receiving regular chow) and the treatment mice on 0.6% DHEA diet. The deciduoma in the uterine horn shown on the left can be clearly seen in the control mice, while no difference between the stimulated and unstimulated uterine horns can be seen in the DHEA-fed mice. A quantitative analysis of the decidual reaction in shown in FIG. 8B, where the mass of the uterine horns is shown. Lastly, it should be noted that ovariectomised mice, similar to post-menopausal women, tend to have increased body fat percentage. However, DHEA administration decreases this gain in body fat levels (FIG. 8C), counteracting the negative effects of hormone withdrawal on overall body-physiology.

Example 5

PPP Inhibitors Prevent Human ESC Decidualization In Vitro

Figure 9A:
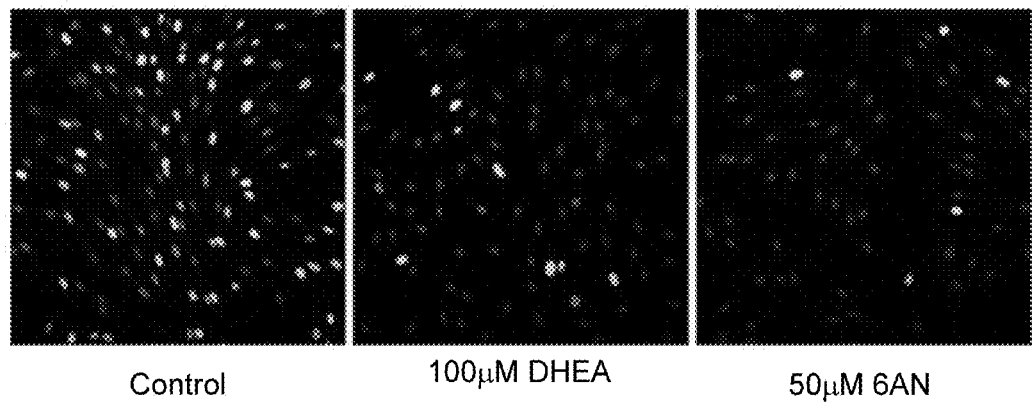
FIG. 9A-D depicts effects of PPP inhibitors on ESC proliferation. (A) Control ESC-Ts show a large proportion of nuclei that are EdU positive, indicating that the cells are actively entering the S-phase and proliferating (left), while the ESC-Ts treated with either 100 mM DHEA (middle) or 50 mM 6AN (right) show a much smaller proportion of EdU-positive nuclei. Quantification of EdU-positive ESC-Ts was conducted by flow cytometry and a representative experiment can be seen for DHEA treatment (B) and 6AN treatments (C). (D) EdU geometric mean fluorescence intensity for the treatments shown in B and C.
Figure 9B:
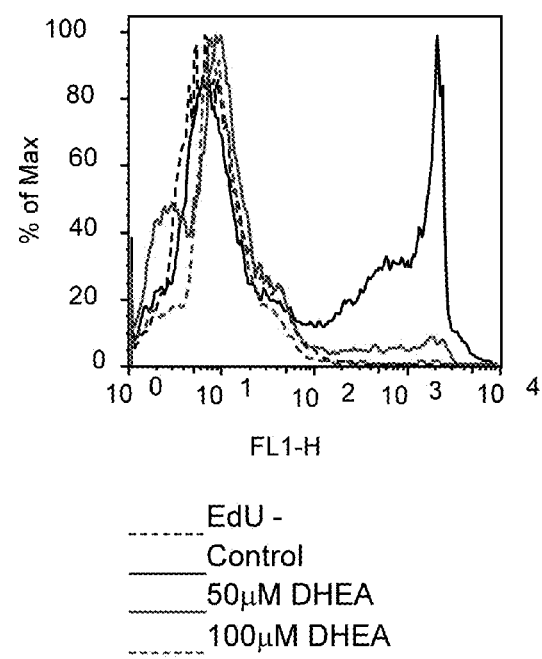
Figure 9C:
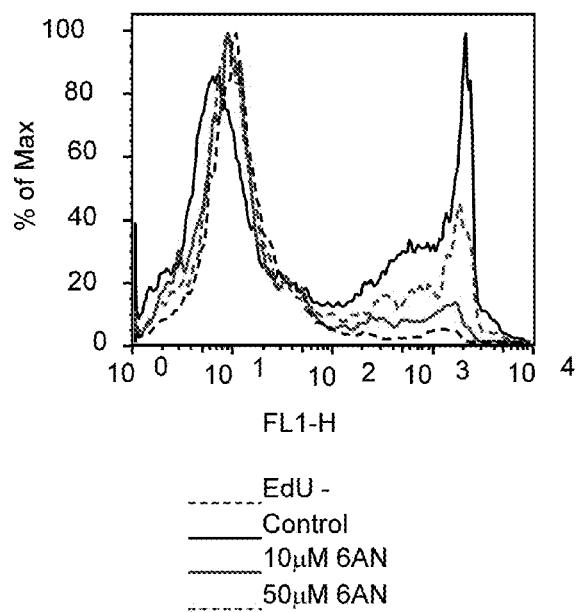
Figure 9D:
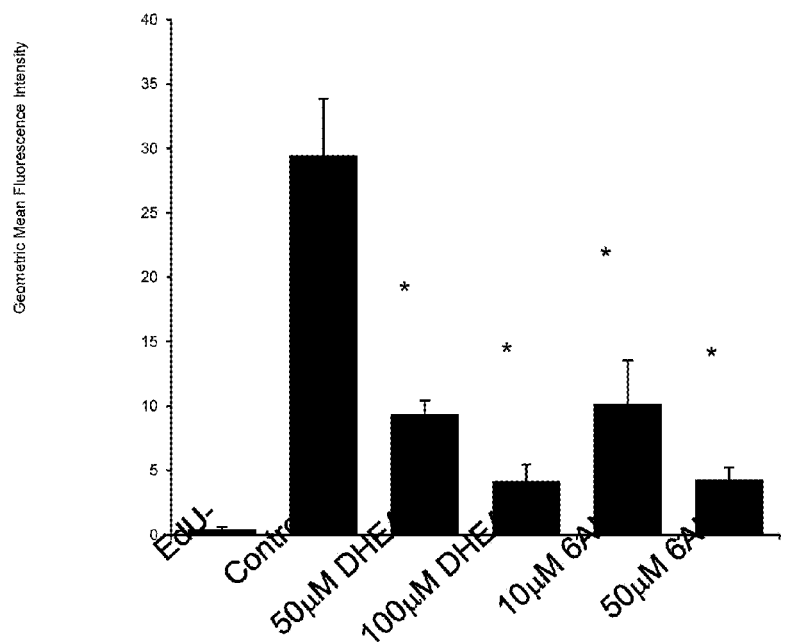

Other groups have shown that DHEA has anti-proliferative effects in a number of cell-lines and tissues. Thus, it was hypothesized that perhaps the PPP inhibitors prevent the proliferation of ESC-Ts and that this is an additional effect, independent of their role in decidualization inhibition. In a human uterus the stromal cells go through a cyclical oscillation between proliferation and differentiation, determined by the hormonal milieu. ESC-Ts in vitro remain in the proliferative state until they are exposed to differentiation media, which causes the cells to halt cell division and enter differentiation. Proliferation of ESC-T cells were monitored by EdU incorporation in vitro, which indicates entry into the S-phase of the cell cycle, in the absence of the differentiation hormones. Representative images of EdU staining show a drastic decrease in EdU-positive nuclei in the 100 μM DHEA and 50 μM 6AN treatments versus the DMSO control (FIG. 9A). Quantitative data acquired by flow cytometry are shown in FIGS. 9B and 9C. The geometric mean fluorescence intensity from 4 independent experiments shows that the presence of DHEA or 6AN decreases proliferation of ESC-Ts in a concentration dependent manner (FIG. 9D). Together with the above results, these data demonstrate that PPP inhibitors not only halt the differentiation of ESCs into decidual cells, but they also inhibit the proliferative phenotype of undifferentiated stromal cells, which is required for expansion of the stromal compartment prior to decidualization.

Example 6

Figure 10A:
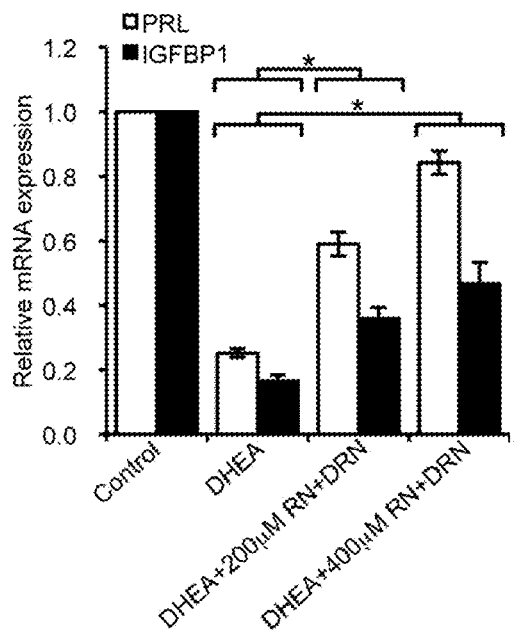
FIG. 10A-C Decidualization inhibition by PPP inhibitors is rescued with exogenous nucleoside administration. (A) Decidualization marker expression in ESCs exposed to differentiation media for 4 days is decreased in the presence of 100 μM DHEA, but is significantly increased with the addition of 200 μM or 400 μM ribonucleosides (RN) and deoxyribonucleosides (DRN). Values are a mean of at least 4 independent experiments+/−SEM. *, $p<0.001$ for PRL and $p<0.05$ for IGFBP1. (B) Effects of 10 μM 6AN treatment are also significantly reversed with addition of 200 μM or 400 μM RN and DRN. Values are a mean of at least 3 independent experiments+/−SEM *, $p<0.001$. **, $p<0.05$ for IGFBP1. (C) Representative images of the ESC morphology; control (upper left), decidualized (upper right), decidualized +100 μM DHEA (lower left), and decidualized+DHEA and 400 μM RN and DRN (lower right).
Figure 10B:
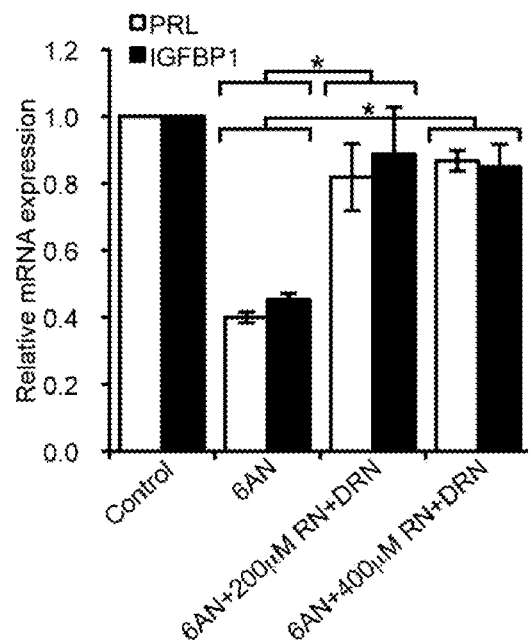
Figure 10C:
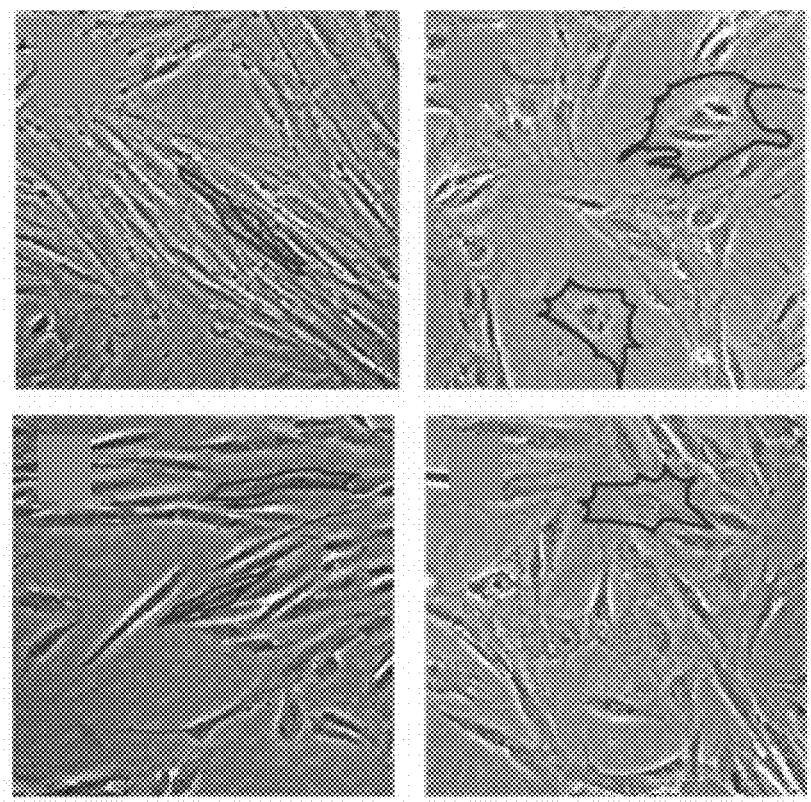

Ribo- and Deoxyribonucleosides Reverse Inhibition of ESC Decidualization by PPP Inhibitors Two major results of the PPP are the production of ribose 5-phosphate and regeneration of NADPH. Production of ribose 5-phosphate is a central component in the de novo synthesis of ribonucleosides (RNs) and deoxyribonucleosides (DRNs). It was hypothesized that perhaps a lack of adequate ribose 5-phosphate formation and the subsequent RN and DRN shortage is responsible for inhibition of decidualization when G6PD inhibitors, DHEA or 6AN, are present. To address this question, ESC-T cultures were used and the differentiation media was supplemented with RNs and DRNs during treatment with PPP inhibitors. On day 4 of ESC-T decidualization in vitro, a drastic decrease in both decidualization markers, PRL and IGFBP1, can be seen when 100 μM DHEA is present. Addition of 200 μM or 400 μM RNs and DRNs together compensated the effect of DHEA and restored the expression of these markers, with PRL reaching almost the same levels as in control decidualizing ESC-Ts (FIG. 10A). To confirm that this was a PPP-specific effect, rescue of decidualization was also performed on ESC-Ts treated with 10 μM 6AN. Addition of 200 μM or 400 μM RNs and DRNs restored the expression of PRL and IGFBP1 to over 90% of the control decidualizing cells (FIG. 10B). The morphology of the ESC-Ts also reflected their degree of decidualization (FIG. 10C). While ESCs decidualizing in the presence of DHEA had a fibroblastic morphology, similar to the control, undifferentiated stromal cells (compare FIG. 10C top left and right panels), the ESCs cultured with DHEA and 400 μM RNs and DRNs were larger and displayed the characteristic morphology of normal decidual cells (compare FIG. 10C bottom left and right panels). This rescue using one of the downstream products of the PPP further implicates this pathway in decidualization and provides evidence that it is the ribose-5-phosphate shortage and not lower NADPH levels that are responsible for decreased ESC-T decidualization in vitro.

Discussion for Examples 1-6

The findings suggest that aberrant glucose metabolism, specifically in the endometrial stroma, leads to inefficient decidualization and, thus, may be an important underlying cause of incomplete embryo implantation and, ultimately, miscarriages. Proper embryo implantation is a critical factor determining the success of a pregnancy, and this process depends on both the embryo and the endometrium, which have to develop in a highly coordinated manner. In a successful implantation, the blastocyst attaches to the endometrial epithelial cells and the trophoblast cells invade through this layer until they reach the endometrial stroma, thus firmly anchoring the embryo into the uterine wall. At the time of implantation, the endometrial stromal cells undergo a process called decidualization and become morphologically and functionally distinct from their former state. This decidua is thought to provide the blastocyst with factors required for further embryo development. Therefore, defects in decidualization lead to incomplete embryo implantation, which results in pregnancy loss. Previous work has demonstrated that glucose uptake increases during decidualization and that lower glucose availability leads to lower decidualization marker expression. The results demonstrate that once glucose is taken up into ESCs, defects in glucose metabolism through the PPP are detrimental to the decidualization process both in vitro and in vivo. Using human and murine primary culture ESCs in vitro, and using an in vivo mouse model of decidualization, the results suggest a mechanism to explain increased miscarriage rates in the context of aberrant glucose and hormonal homeostasis, seen in a growing number of women today.

In this study, it was demonstrated that the decidualization process is characterized not only by glucose transporter upregulation and increased glucose uptake, but also by the specific flux of glucose to a particular energy-producing pathway, the pentose phosphate pathway. Inhibition of downstream glucose metabolism through the PPP, via interruption of G6PD activity (the rate limiting enzyme in this pathway) by either specific inhibitors or a direct decrease in G6PD expression using RNAi, can dramatically decrease stromal decidualization. Additionally, it is shown that providing one of the products of the PPP, nucleosides, rescues decidualization in the presence of DHEA or 6AN. The major products of the PPP are ribose-5-phosphate, which is a precursor for nucleosides, and NADPH, which is used for biosynthesis of cholesterol, fatty acids and for regeneration of reduced glutathione. The data demonstrates that ribo- and deoxyribonucleoside supplementation can rescue ESC decidualization in the context of PPP inhibition, which further supports the hypothesis that full activity of this pathway is necessary for this differentiation process. However, this does not exclude the possibility that the other major product of the PPP, NADPH, may play a role and contribute to the decidual response as well. Further studies are required to fully characterize the role NADPH and subsequently the cell's redox balance may have in ESC decidualization.

Perhaps the most clinically relevant finding of this study is that DHEA prevents decidualization of ESCs both in vitro and in vivo. DHEA is an endogenous hormone produced by the adrenal glands and its serum levels are increased ~2-fold in about 50% of women with PCOS, a population that also has increased miscarriage rates. This hormone is also widely available as a supplement for treatment of multiple conditions such as Alzheimer's disease, erectile dysfunction, inflammatory diseases, and diabetes; however no definitive studies have substantiated this widespread use. Most recently DHEA has been used to supplement In Vitro Fertilization (IVF) treatment of infertility and it is believed to increase oocyte quality. Nonetheless, no mechanism or evidence of effect has been shown. DHEA, however, has been shown to act as a potent non-competitive inhibitor of G6PD and this inhibitory ability of DHEA results in a block of differentiation in some cell types. Very short durations of DHEA exposure prevented differentiation of 3T3-L1 mouse fibroblasts to adipocytes and this effect was directly attributed to its ability to inhibit G6PD. These DHEA-specific effects are in strong agreement with the findings in this study that DHEA hinders the differentiation of murine and human ESCs during the process of decidualization in vitro. Parallel studies using another, direct inhibitor of G6PD, 6-AN, implicate that DHEA's effects may be due to its inhibition of the PPP. Since the endometrium is highly hormone-sensitive, the possibility that DHEA has effects other than its role in merely inhibiting the PPP is not excluded. However, mechanistic evidence is presented for DHEAs G6PD-inhibitory function in endometrial differentiation that implicates it as a possible target in future infertility treatments in women with PCOS. Additionally, these inhibitory effects must be taken into account since DHEA supplements are designed for other indications in women of reproductive age desiring pregnancy.

A role for DHEA in early pregnancy has been studied in vivo, previously in mice. DHEA treated mice, which exhibit some of the same features as women with PCOS, have increased rates of miscarriage and embryo resorptions. These in vivo effects were mostly attributed to ovarian failure and the subsequent changes in the balance of estrogen and progesterone needed to maintain pregnancy. The conclusion that DHEA's role in ovarian steroidogenesis was responsible for the pregnancy loss was only speculative since the effect of two other key variables, the embryo and uterine endometrium, were not controlled for. In studies presented here, an oophorectomy model was utilized, which more appropriately focuses on the function of the endometrium at the time of embryo implantation. This approach allowed the direct dissection of the effects of DHEA on the endometrial stroma differentiation. Moreover, it allowed the control for any abnormalities in embryo development by inducing the decidual response in the absence of a true pregnancy, via an exogenous physical stimulus. Thus, it was demonstrated that DHEA treatment prevents the sensitization of the endometrium for implantation by specifically inhibiting stromal decidualization, and this effect is independent of the embryo or estrogen and progesterone levels in the serum. This finding is important because in many cases of infertility, ovulation induction is the initial approach in the clinic. However, some studies show that even when an ovulation is corrected in patients with PCOS, a miscarriage rate of 2-fold higher than the average population remains. Results of this study provide a mechanistic explanation for how the increased levels of DHEA seen in these patients may be involved. The murine model-based results demonstrate that high levels of DHEA in vivo obliterate the ability of the endometrium to decidualize and, therefore, prevent embryo implantation.

Finally, the data in this study also show that DHEA and other PPP inhibitors not only affect the differentiation of the stroma, but also prevent ESC proliferation. This is an important addition to the data regarding DHEA's effects on decidualization, because it shows how extensive of a role DHEA may play in causing infertility in women with PCOS. The endometrium undergoes a number of morphological and functional changes during the menstrual cycle, which, in the human, can be separated into two main phases, the proliferative and secretory. During the proliferative phase, the stromal compartment is regenerating and thickening and therefore, as the name would imply, the ESCs are proliferating at a high rate. This stage of the cycle is characterized by low serum progesterone and increasing serum levels of estrogen. During the secretory phase, which begins at the time of ovulation, ESCs stop proliferating during the first 3 days. By the midsecretory phase, the process of decidualization of the stroma begins. Unlike many other species, in the human stromal decidualization does not require the presence of an embryo and begins prior to conception. Once progesterone levels drop at the end of the cycle, in the absence of an embryo, the specialized, terminally differentiated decidual lining of the endometrium must be shed, and the endometrium once again reenters the proliferative phase to rebuild the lost stromal compartment. Data in this study provide evidence that DHEA inhibits both phases of the endometrial menstrual cycle, and, therefore, has a dual role in causing infertility. First, the increased DHEA levels inhibit the building of the endometrial lining, leaving a thin stromal compartment after completion of the proliferative phase. Second, DHEA inhibits the differentiation of the stroma into decidual cells in the secretory phase of the human menstrual cycle.

Taken together, these results strongly suggest that elevated levels of DHEA cause a strong increase in implantation failure by interfering with proper growth, development and differentiation of the endometrium into a decidua. This inhibitory action can attributed, at least in part, to DHEA's inhibition of G6PD and prevention of glucose flux through the PPP. Further, it is shown that exogenous ribo- and deoxyribonucleoside supplementation restores the decidual reaction in vitro and, therefore, the shortage of ribose-5-phosphate produced by inhibition of PPP may be responsible for the observed decrease in decidualization when PPP inhibitors are present. This finding is of great importance as DHEA is increased in a number of women with PCOS who have high rates of failed pregnancy, and because it is also commonly being used clinically as an aid in infertility treatment. Several studies correlate DHEA administration with an increase in the number of oocytes retrieved from women undergoing IVF and a few studies also suggested a reversal of early ovarian failure by DHEA. No direct investigations of DHEA's effects on oocyte number and quality, however, have been performed to date. Data in this study suggest that even if a greater number of oocytes can be produced in these infertile women, the resulting high levels of DHEA can inhibit the successful implantation of the embryos by inhibiting decidualization of the endometrial stroma. This possibility needs to be taken into careful consideration before using this supplement in women receiving infertility treatment.

Materials and Methods For Examples 1-6

Animal Care and Use

All mouse studies were approved by the Animal Studies Committee at Washington University School of Medicine and conform to the Guide for the Care and Use of Laboratory Animals published by the National Institutes of Health. Female C57BL/6NCr (National Cancer Institute) mice 7-8 wks of age were used for the isolation of primary ESCs. FVB/NJ mice were used for in vivo deciduoma induction studies. For experiments involving pregnant mice, the day on which a vaginal plug was detected is referred to as the first day post coitus (1dpc).

Isolation of Murine Endometrial Stromal Cells and Culture Conditions

For in vitro decidualization of ESCs, female mice were sacrificed at 4dpc. Pregnancy was confirmed by flushing dissected uterine horns and ostia with HBSS and observing for presence of blastocysts. Uteri confirmed for pregnancy were cut into 1 mm³ pieces and incubated in Dulbecco's modified Eagle's Medium:F12 medium (DMEM:F12) without phenol red supplemented with 2 g/liter Collagenase Type I (Gibco) for 60-90 min at 37° C. Tissues were vortexed every 15 min during incubation. Following incubation, the solution was passed through a 40 μm sieve (BD Falcon) and centrifuged at 1100 rpm for 5 min. The ESCs were then resuspended in DMEM:F12 w/o phenol red, supplemented with 2% heat-inactivated charcoal dextran-stripped calf serum (HyClone) and 50 μg/ml penicillin/streptomycin (Cambrex Bio Science). ESCs were plated in 6-well cell culture plates at $5\times10^5$ cells/well and media was supplemented with β-Estradiol-water-soluble (E2) at a final estradiol concentration of 10 nM and Progesterone-water-soluble ($P_4$) at a final progesterone concentration of 1 μM for 72 h (Sigma). Control samples received no hormone supplementation.

Isolation of Human Endometrial Stromal Cells and Culture Conditions

Endometrial tissue was obtained from human uteri after hysterectomy conducted for benign disease or from endometrial biopsies. Informed consent was obtained from each patient before surgery and protocols were approved by the Human Research Protection Office of Washington University (HRPO#07-0949). Tissues were placed in HBSS and transported to the laboratory. hESCs were isolated and cultured as previously described. In vitro decidualization was performed as previously described with several changes. Cells were seeded in 6-well plates at $2\times10^5$ cells/well in DMEM:F12 without phenol red, supplemented with 2% heat-inactivated charcoal dextran-stripped calf serum (HyClone) and 50 μg/ml penicillin/streptomycin (Cambrex Bio Science). Cells were treated with 1 μM medroxyprogesterone-17-acetate (MPA) (Sigma) and 0.5 mM $N^6$, 2'-O-Dibutyryladenosine 3',5'-cyclic monophosphate sodium salt (db-cAMP) (Sigma). Control samples received 0.1% ethanol vehicle control.

Gene Expression Knockout.

Human primary ESC cells were isolated as described above and then infected with Mission short hairpin RNA (shRNA) lentiviral particles (Sigma-Aldrich), which encoded shRNA specific to G6PD or the non-target scrambled control. Two days later the cells were treated with 10 mM puromycin for 48 hrs to eliminate non-infected cells. Next, the ESCs were treated for four days with MPA and db-cAMP as described above to induce decidualization. Control cells received no hormones. mRNA levels were assessed by Real-time PCR as described above, using G6PD sense (SEQ ID NO. 1; 5'-ATC GAC CAC TAC CTG GGC AA-3') and G6PD antisense (SEQ ID NO. 2; 5'-TTC TGC ATC ACG TCC CGG A-3') primers. Protein was also isolated from Trizol following the manufacturer's protocol (Invitrogen) and expression G6PD was confirmed by Western blot as described elsewhere. The rabbit-anti-G6PD antibody (Bethyl Laboratories) was used at a 1:1000 dilution.

Artificially Induced Deciduoma

To generate deciduomas 7-8 wk-old female FVB/NJ mice were used and treated as described previously. A time line of the hormone administrations is presented in FIG. 7a, adapted from Herington et al. Briefly, mice were ovariectomized and allowed 2 weeks for recovery. They were then injected with 100 ng 17b-estradiol ($E_2$) (Sigma) for three days, rested two days, and then injected with 10 ng $E_2$/1 μg Progesterone ($P_4$, Sigma) for three days. The steroids were diluted in sunflower seed oil (Sigma) and injections were all subcutaneous, conducted at 1000-1030 h with the total volume being 50 μL. Immediately following the last of the above sensitization injections, the right uterine horn received an intra-luminal injection of 100 μL of sunflower seed oil. Mice continued to receive 1 μg $P_4$ subcutaneously for up to 4 days. Mice receiving the DHEA treatment received 2 μg/100 g body weight starting on the day the $E_2/P_4$ injections were begun and continued for the 7 days following, until mice were sacrificed. On the day following the last injection, serum samples were collected, the mice were sacrificed and uterine horns dissected out. Serum DHEA, $E_2$ and $P_4$ levels were analyzed by ELISA assays (Alpco Immunoassays).

Proliferation Assays

To assess in vitro proliferation, ESC-Ts were plated in 6-well plates at $2\times10^5$ cells/well. Following 60 hr of the treatment indicated in the experiment, EdU was added to the culture medium at a concentration of 10 mM. Cells were harvested and stained using the Click-iT EdU Flow Cytometry Kit (Invitrogen). Quantitative data were collected using a BD FACSCalibur flow cytometer (Becton Dickinson, San Jose, Calif.) and analyzed with FlowJo software (TreeSTar, Inc., Ashland, Oreg.). For confocal microscopy, the cells were stained on coverslips using the same protocol. Nuclei were counterstained with TOPRO-iodide (Molecular probes) at a 1:500 dilution. Cells were mounted on slides using Vectashield (Vector Labs) and visualized using a Nikon C1 microscope.

Introduction for Examples 7-11

Up to seven percent of reproductive age women are diagnosed with polycystic ovary syndrome (PCOS). PCOS is a heterogeneous disease with an unclear etiology. Currently, the diagnosis of PCOS is based on clinical criteria, including hyperandrogenism, ovulatory dysfunction and ovarian changes. Other features include insulin resistance and long-term risks of diabetes mellitus. Up to forty percent of women with PCOS exhibit glucose intolerance and approximately ten percent have type 2 diabetes mellitus. Furthermore, PCOS may increase the risk of coronary artery disease by two-fold.

Given the ovulatory dysfunction experienced by these women, assisted reproductive techniques are frequently successful in restoring ovulation and often lead to pregnancy. Ovulation rates with clomiphene citrate have been reported as 59-75.1% with pregnancy rates of 15.4-32%. There are some reports that women with PCOS have an increased risk of miscarriage, as high as 35-65%. The miscarriage rate was found to be 24.7% in PCOS women compared to 8.7% in controls. More modest miscarriage rates of 14% in women with PCOS and 3% in normal controls have also been reported. However, others have not found similar results. These conflicting findings may be due to the inherent heterogeneity of the PCOS population, or use of different diagnostic criteria and definitions for clinical pregnancy and miscarriage. Despite the varying results, it is reasonable to suspect that the abnormal hormonal environment that leads to ovulatory dysfunction may also affect the quality of ovulated oocytes, and therefore, embryo competence potentially leading to increased miscarriages.

Due to ethical concerns with human embryos, it has been difficult to study the effect of PCOS on human oocyte and embryo quality. Therefore, most information comes from animal models. There have been many attempts to develop an animal model of PCOS, but due to the complexity and unknown etiology of the disease, there is no perfect model. Previously, subcutaneous dehydroepiandrosterone (DHEA) was used to create polycystic ovaries in rats.

The oocyte requires energy to complete the maturation process. Most available glucose is utilized by the cumulus-oocyte complex (COC) via glycolysis and the tricarboxcylic acid (TCA) cycle in order to produce energy in the form of intermediate metabolites and ATP. Previous work by the inventors has shown that citrate and ATP levels in diabetic oocytes correlate with oocyte quality; specifically lower levels indicate decreased competence. A much smaller amount of glucose is metabolized via the pentose phosphate pathway. The pentose phosphate pathway is essential for completion of oocyte maturation. DHEA is often increased in women with PCOS. DHEA can be converted to other androgens and estrogens that disrupt the normal feedback of the hypothalamus-pituitary-ovary axis. Furthermore, DHEA is a known non-competitive inhibitor of glucose-6-phosphate dehydrogenase (G6PDH), the rate-limiting enzyme in the pentose phosphate pathway. The pentose phosphate pathway leads to production of purine substrates and NADPH, important for redox state. As described in the examples above, inhibition of this pathway by DHEA prevents proliferation and decidualization of the uterine endometrium through a decrease in purine synthesis. Because decidualization is a required process for embryo implantation, this is one possible explanation for the increased miscarriage rate seen by some groups in PCOS patients. Poor oocyte competence, and therefore, poor embryo quality, may also lead to increased miscarriage rates. Based on the findings in the endometrium, the effects of DHEA on the glucose metabolism in the oocyte are explored in these examples.

Example 7

Effect of DHEA on Hormone Profile and Ovarian Morphology

Figure 11A:
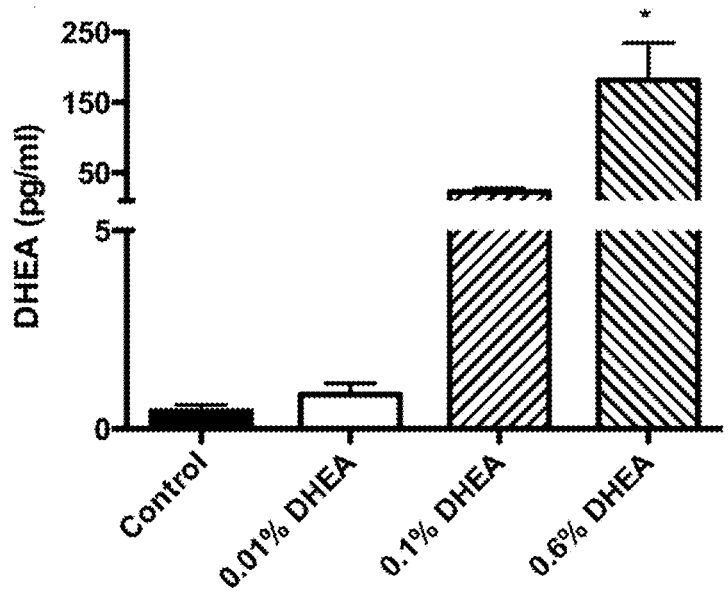
FIG. 11A-D graphically depicts hormone concentrations in control and DHEA-fed mice. (A) DHEA, (B) estradiol and (C) testosterone were measured 48 hours following PMSG. (D) Progesterone was measured 24 hours after injection with hCG. Values are mean±SEM. *$p<0.002$; n=4-7.
Figure 11B:
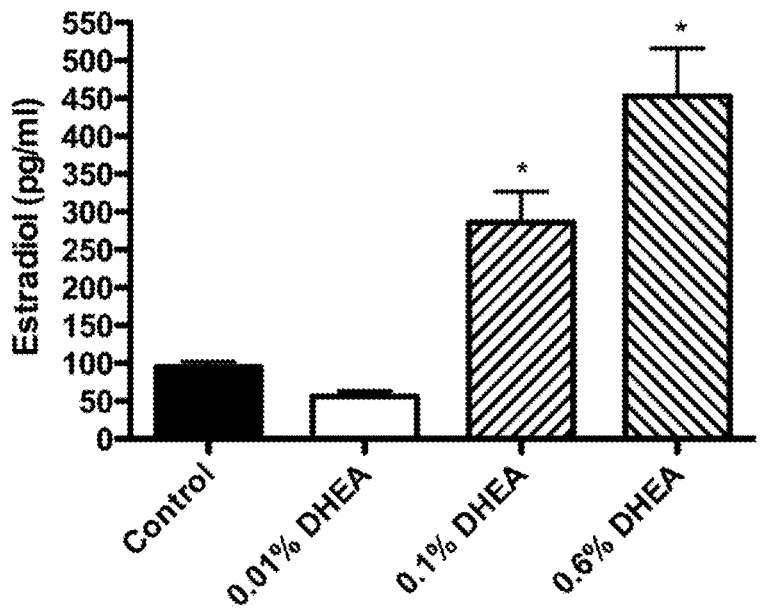
Figure 11C:
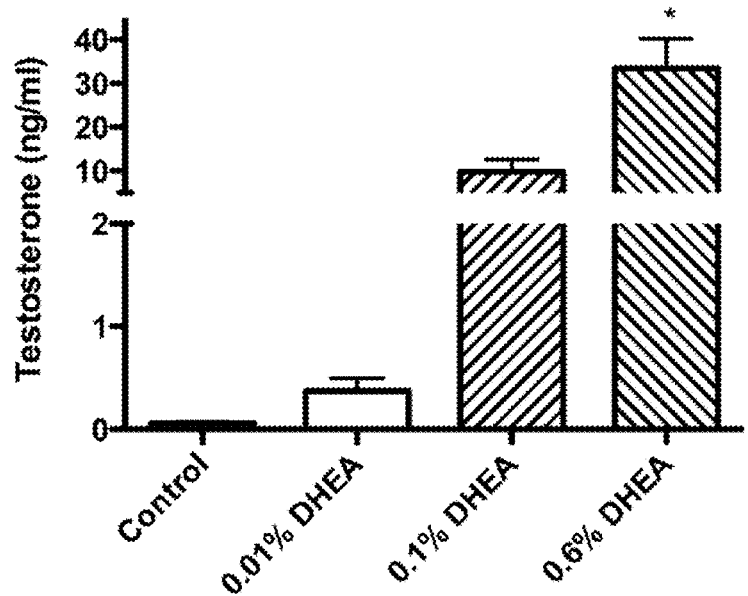
Figure 11D:
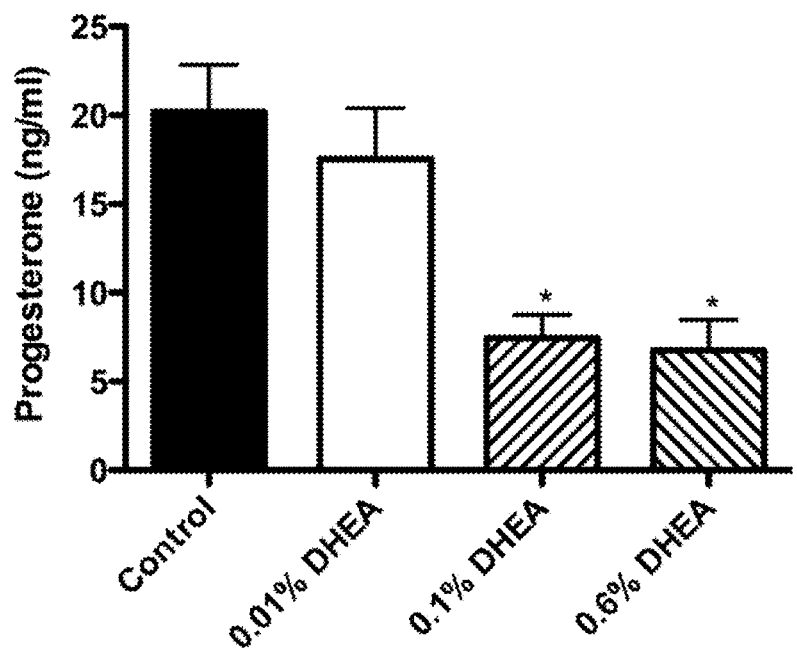

To determine the effect of the various DHEA diet concentrations on the hormone profile of mice, DHEA, estradiol, testosterone and progesterone were measured. As expected, DHEA was elevated in the DHEA-fed mice in a dose-dependent fashion (FIG. 11A). Estradiol and testosterone were also elevated in the treatment groups (FIG. 11B-C). The 0.01% and 0.1% DHEA diet led to non-significant elevations in DHEA and testosterone hormone levels compared to controls. However, both the 0.1% and the 0.6% DHEA diets led to significantly elevated levels of estradiol ($p<0.0001$). Progesterone was measured as a marker of ovulation. Again, serum levels were lower in mice exposed to DHEA in a dose-dependent fashion; however, progesterone was not significantly lower in the 0.01% DHEA group. (FIG. 11D)

Figure 12A:
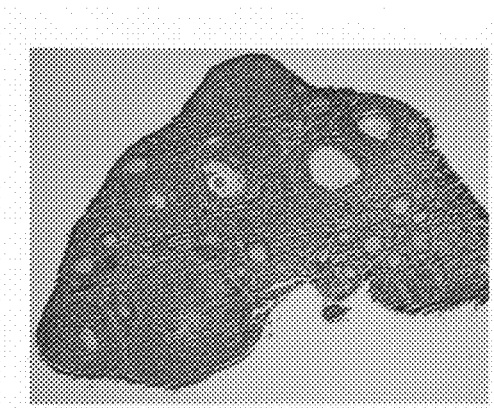
FIG. 12A-E depicts images and plots representing the number of follicles in control (A) and DHEA-fed mice. (B-D) Representative H&E-stained ovarian sections (DHEA treatment). (E) Secondary follicles and corpora lutea follicle counts. Follicles with visible nuclei were classified and counted. Values are mean±SEM. *$p<0.01$; n=5.
Figure 12B:
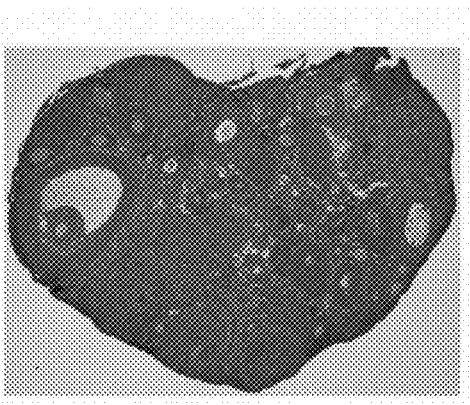
Figure 12C:
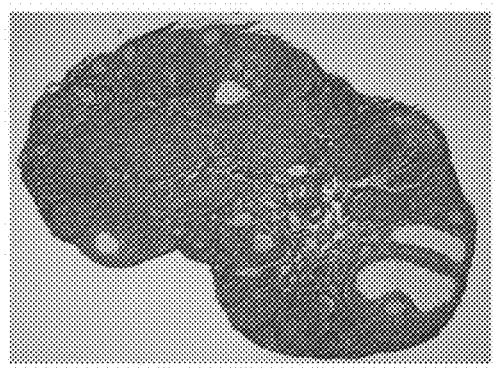
Figure 12D:
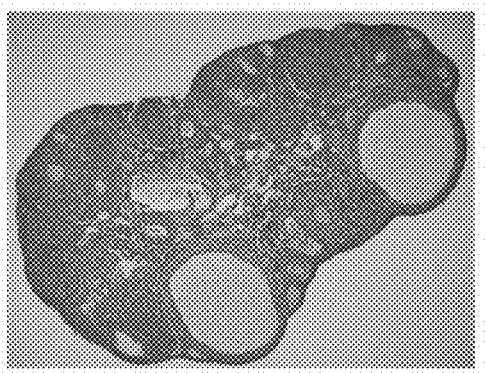
Figure 12E:
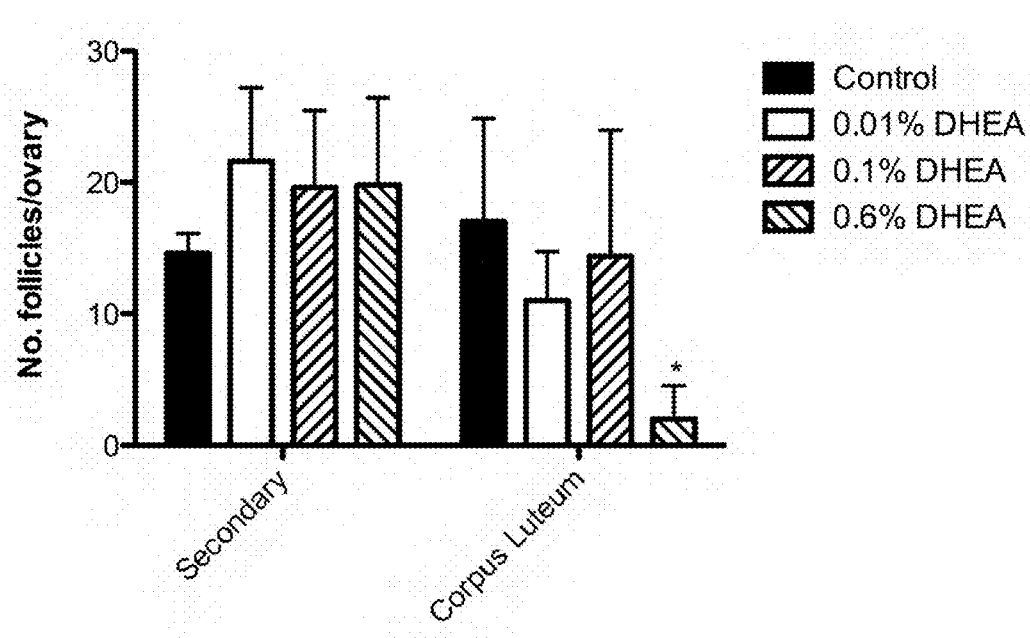

Ovarian morphology revealed that mice fed both the control diet and the DHEA-supplemented diet had follicles at various stages of development. The ovaries from mice on the 0.6% DHEA diet had large cystic structures (FIG. 12A), similar to what has been described previously in rats treated with subcutaneous DHEA. DHEA-fed mice had more secondary follicles, although not statistically significant, and fewer corpora lutea than the mice on the regular rodent chow. However, only the 0.6% DHEA diet led to a significant difference in the number of corpora lutea (FIG. 12B). The number of secondary follicles that progressed to corpora lutea, and therefore were ovulated, was significantly lower in the 0.6% DHEA-fed mice.

Example 8

Effect of DHEA on Estrous Cycles and Ovulation

Figure 13A:
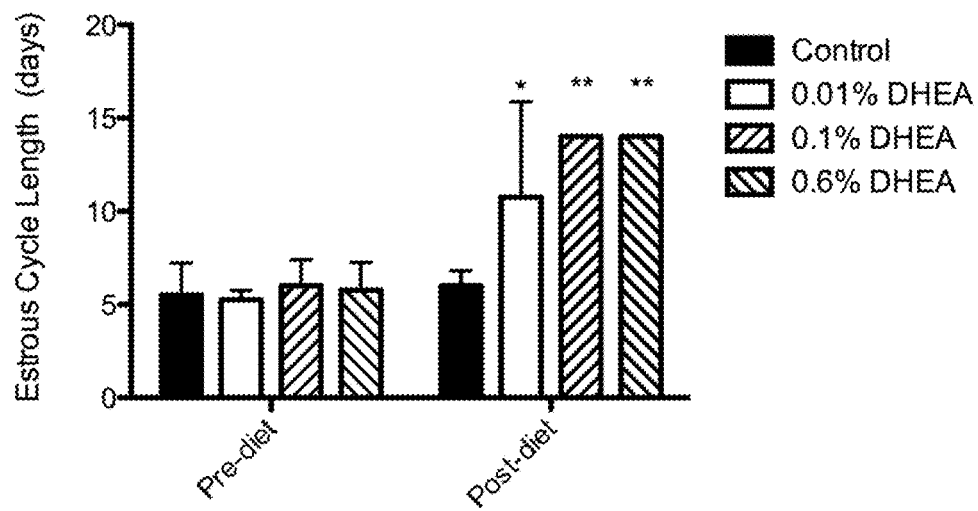
FIG. 13A-B graphically depicts estrous cycles and pregnancy rates of control and DHEA-fed mice. (A) Graphic representation of average length of estrous cycle by vaginal smears taken daily for 8 days pre- and 15 days post-diet. All mice in the 0.1% DHEA and 0.6% DHEA groups post-diet remained in the same stage of the estrous cycle. (B) Number of pups per litter while on DHEA diet. Values are mean±SEM. *$p<0.05$, **$p<0.001$; n=4.
Figure 13B:
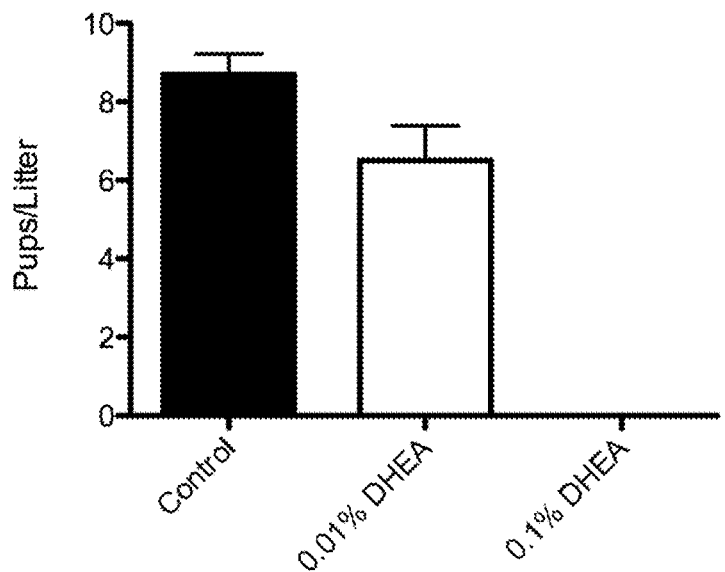

Estrous cycles were evaluated for eight days in pubertal females in each treatment group while on regular rodent chow to confirm normal cycles prior to DHEA supplementation. On average, all groups had an estrous cycle length of five days. After two weeks on the DHEA diets, the 0.01% DHEA concentration led to cycles that were approximately five days longer than controls. Mice fed the 0.1% DHEA and 0.6% DHEA remained in metestrus or diestrus for the entire evaluation period (FIG. 13A). Mice fed the 0.01% DHEA were able to produce pups while on the diet, however the litters were smaller than the controls. The 0.1% and 0.6% DHEA (not shown) mice did not deliver any pups (FIG. 13B).

Figure 14A:
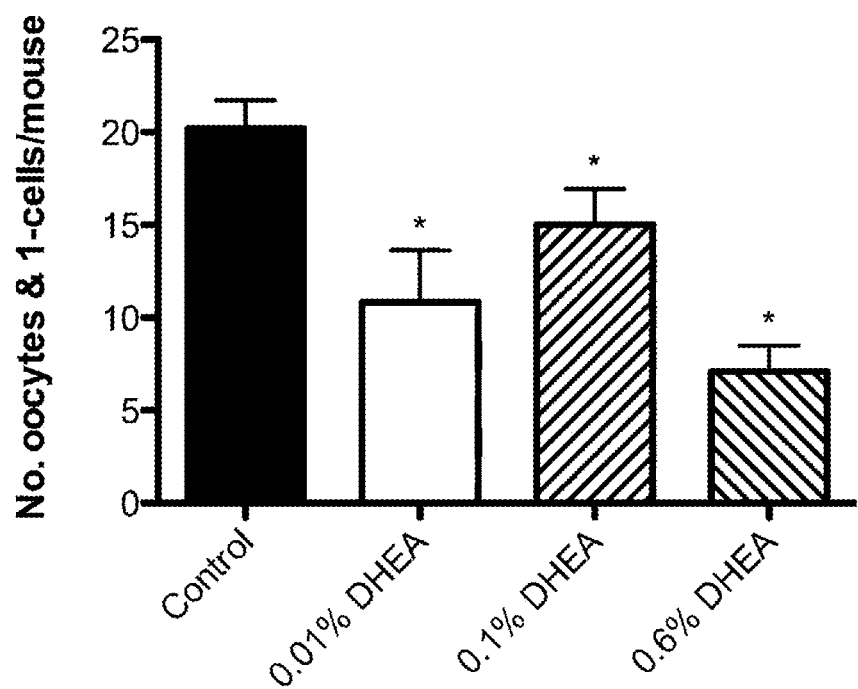
FIG. 14A-B graphically depicts ovulation rates from control and DHEA-fed mice. (A) Ovulated oocytes and 1-cell embryos were collected from ampulla of the oviduct and counted. Values are mean±SEM. *$p=0.0003$; n=11. (B) Number of follicles in control and DHEA-fed mice. Follicles with visible nuclei were classified and counted. (n=5 mice)
Figure 14B:
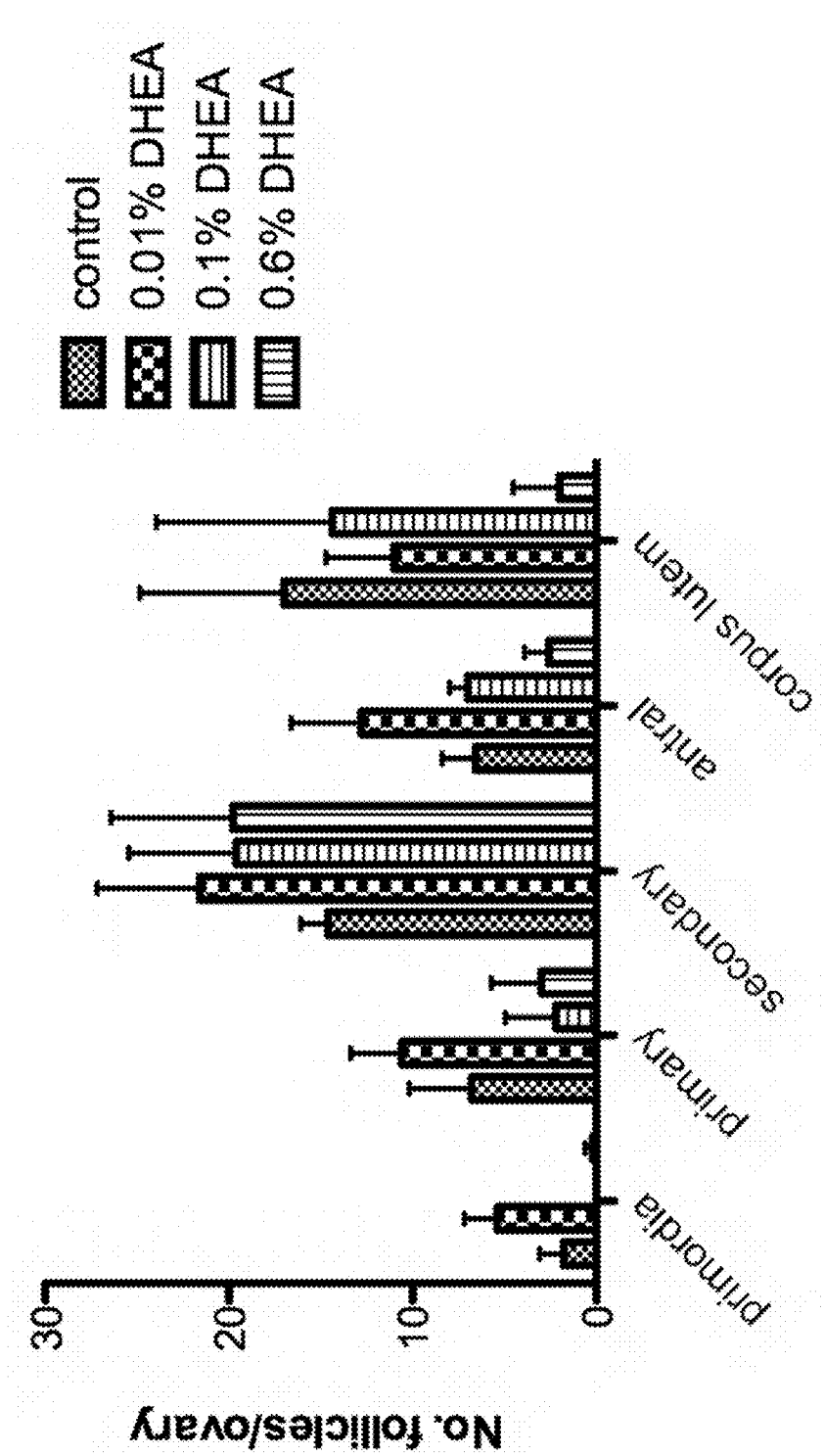

Although DHEA alters normal estrous cycles, ovulation can be induced by ovarian hyperstimulation. Ovulation rates were significantly lower in the DHEA groups compared to the controls following PMSG and hCG. The number of ovulated oocytes for mice fed control, 0.01% DHEA, 0.1% DHEA and 0.6% DHEA diet were 20.2±1.5, 10.8±2.8, 15±1.9 and 7.1±1.4 respectively (FIG. 14).

Example 9

Decreased Metabolism in DHEA-Exposed Oocytes and Blastocysts

Figure 15A:
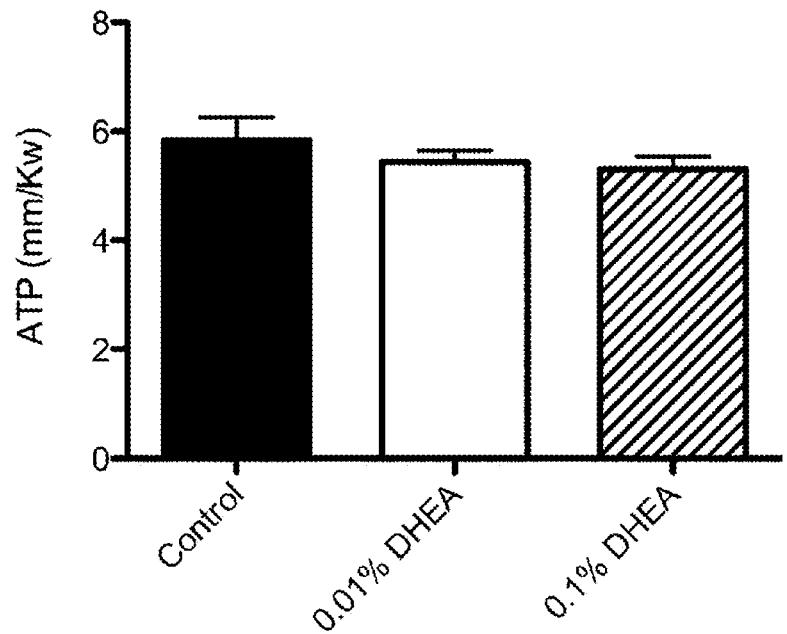
FIG. 15A-C graphically depicts metabolite levels and enzyme activity in single oocytes. (A) ATP levels, (B) citrate levels and (C) G6PDH enzyme activity. Values are mean±SEM. *$p<0.05$; n=3.
Figure 15B:
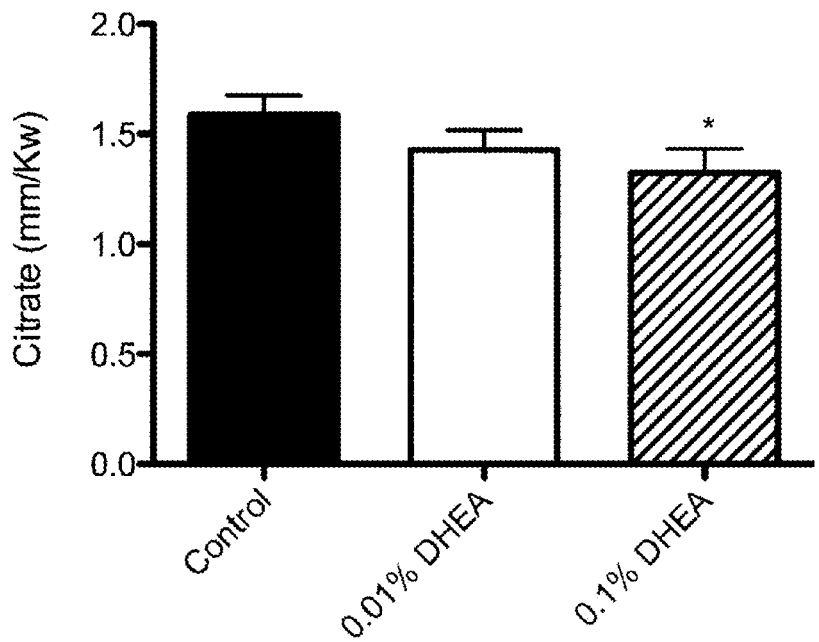
Figure 15C:
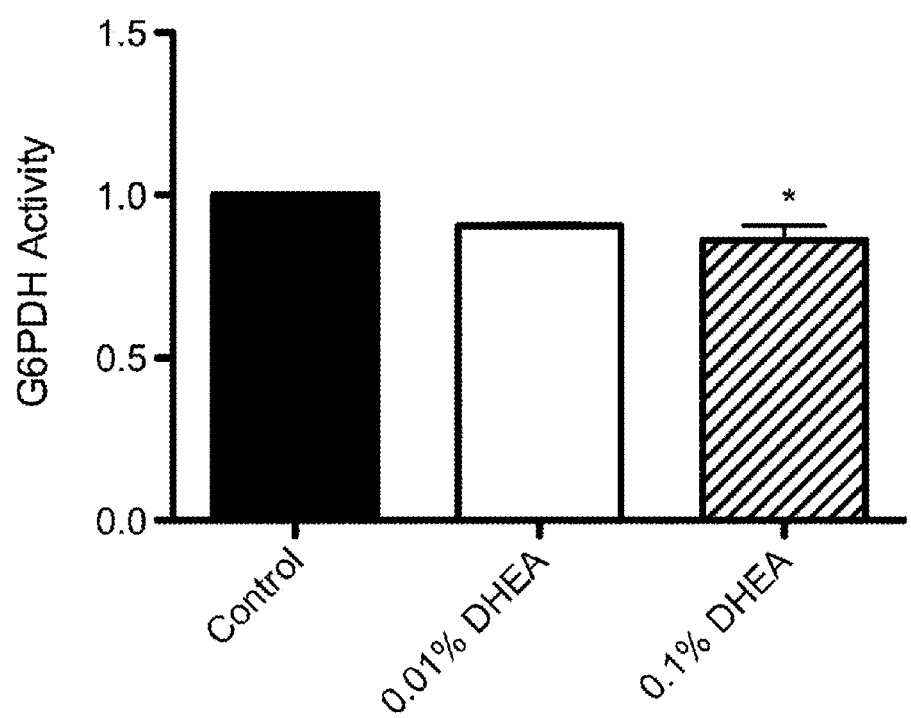

Given the large alteration in hormone profile, estrous cycle and ovulation rate seen with the 0.6% DHEA diet, the two lower concentrations of 0.01% DHEA and 0.1% DHEA were used to evaluate oocyte metabolism. ATP levels did not differ significantly in control denuded GV oocytes compared to those from DHEA-fed mice (FIG. 15A). However, citrate levels were significantly lower in the 0.1% DHEA diet group. The 0.1% DHEA diet also led to significant inhibition of G6PDH to 87% of normal (FIG. 15B-C).

Figure 16A:
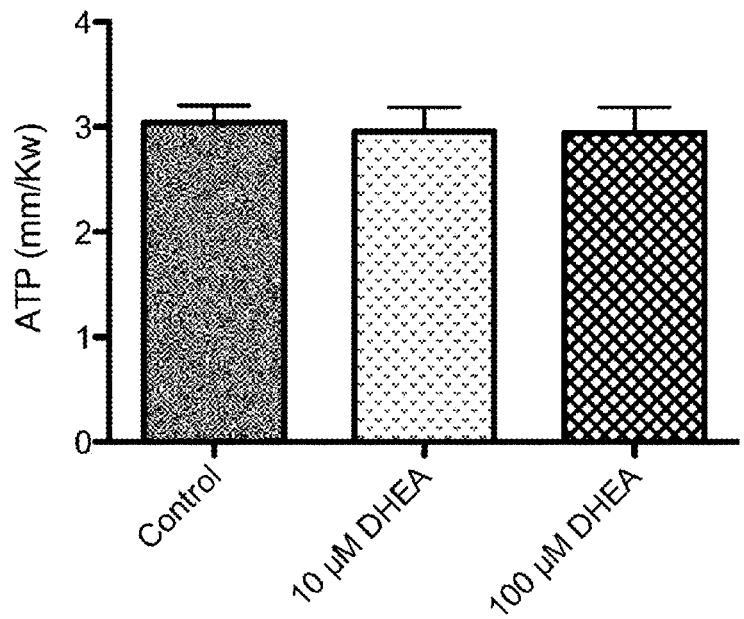
FIG. 16A-B graphically depicts metabolite levels in single blastocysts. Two-cell embryos were cultured in HTF with 0.25% BSA with or without DHEA to blastocyst stage. (A) ATP levels and (B) citrate levels. Values are mean±SEM. *$p<0.05$; n=3-4.
Figure 16B:
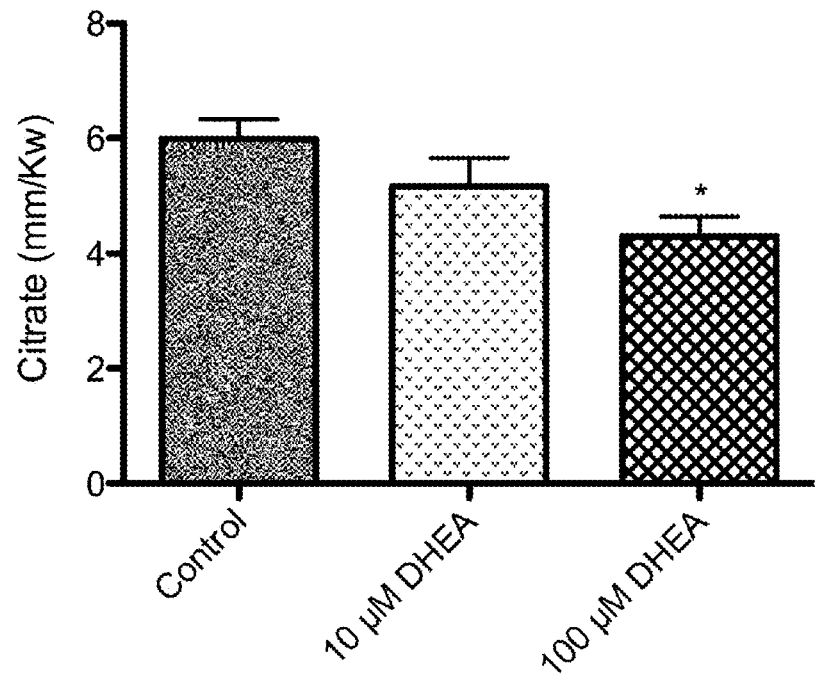
Figure 17A:
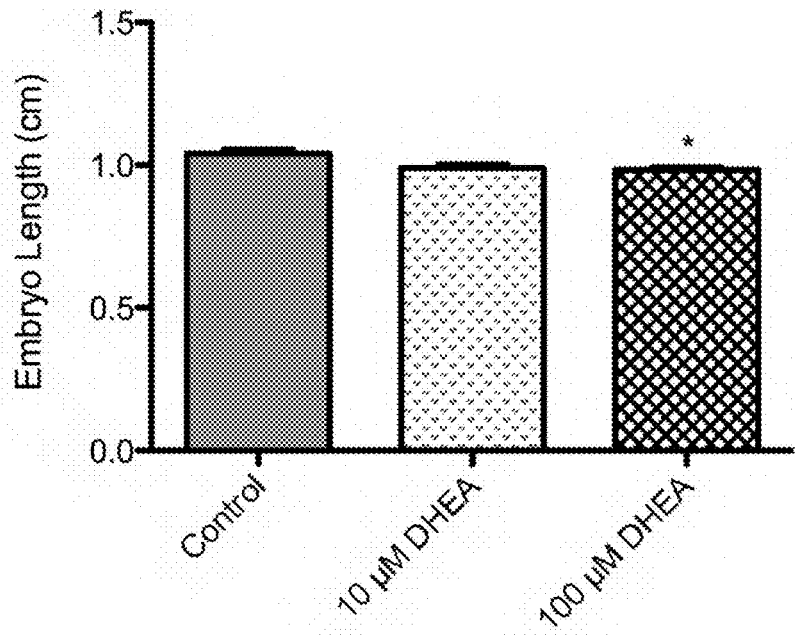
FIG. 17A-F depicts plots and an image representing embryo transfer. Two-cell embryos were cultured in HTF with 0.25% BSA with or without DHEA to blastocyst stage and transferred to pseudopregnant females. (A) Embryo size, (B) embryo weight, (C) placenta weight, (D) implantation rate and (E) resorption rate; (F) representative 14.5dpc embryos. Values are mean±SEM. *$p<0.05$; n=3.
Figure 17B:
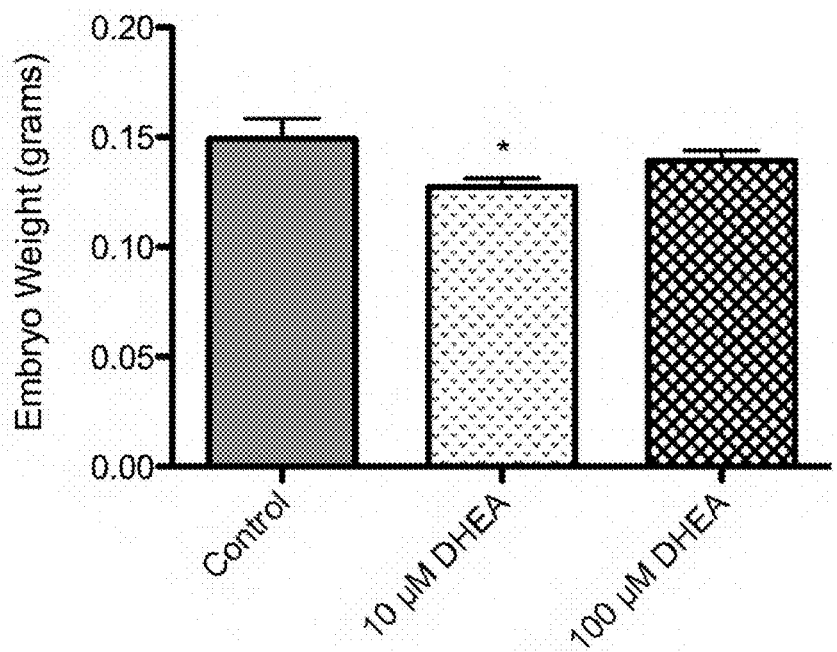
Figure 17C:
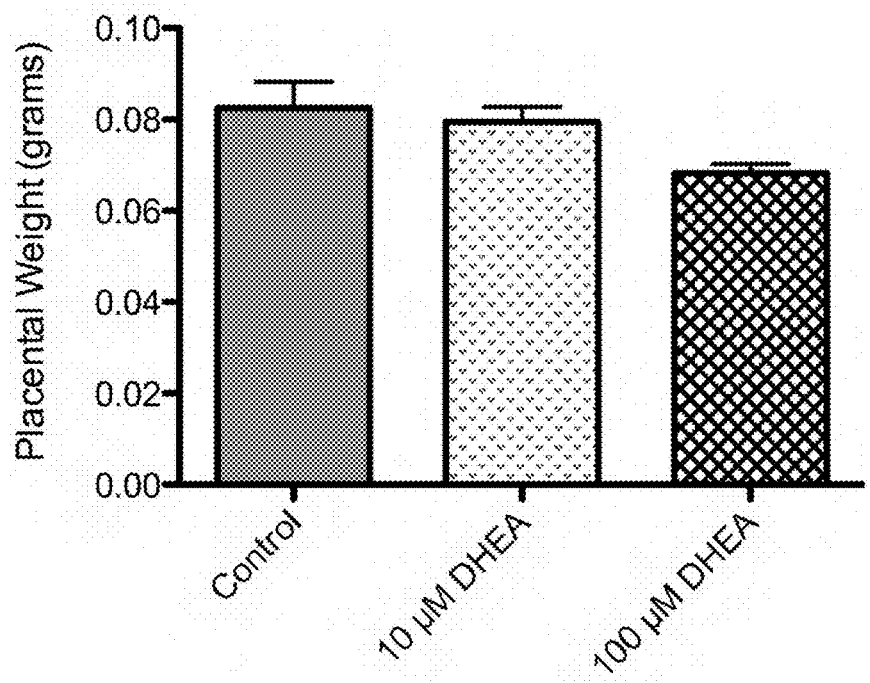
Figure 17D:
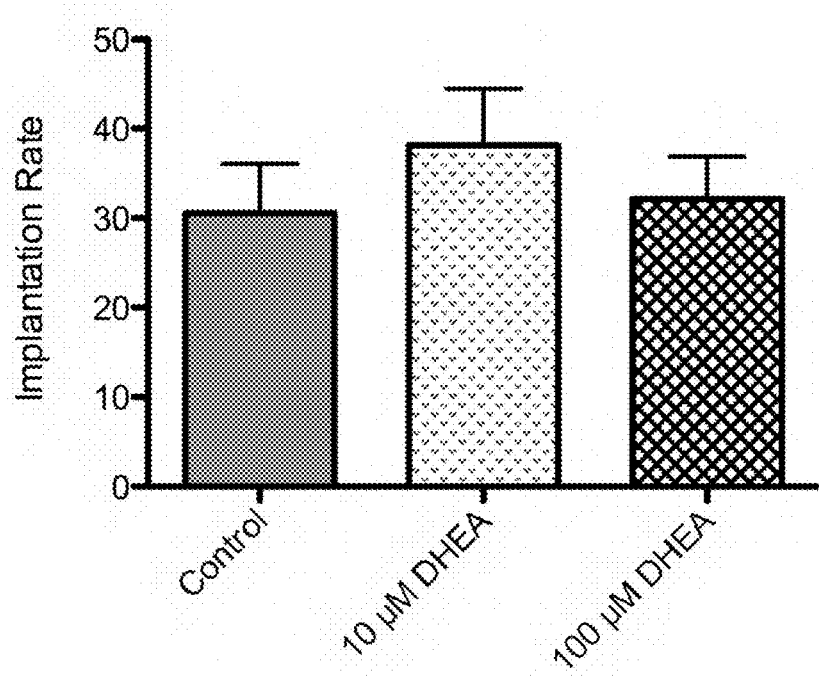
Figure 17E:
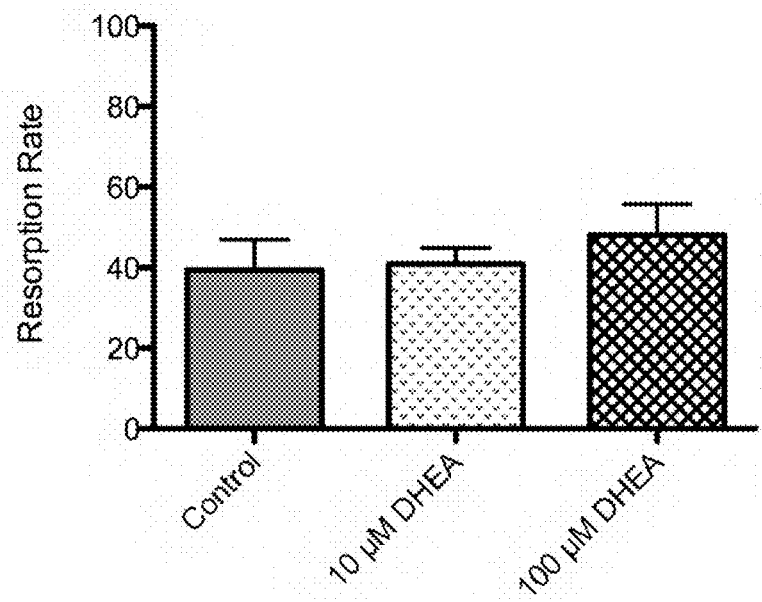
Figure 17F:
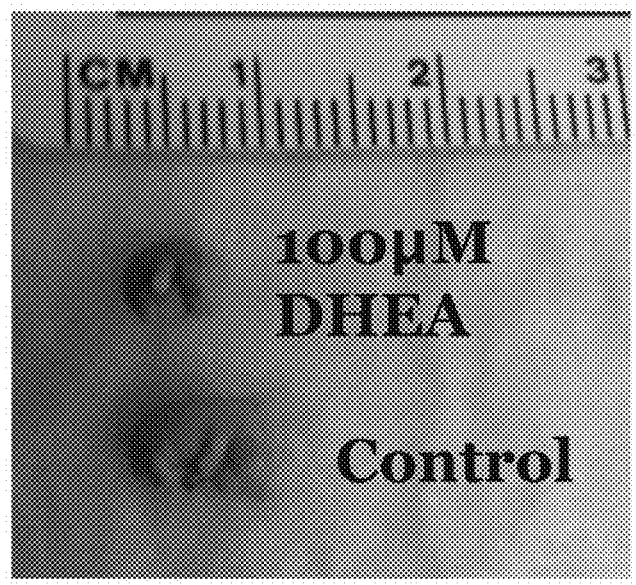

To evaluate the effect of acute exposure of DHEA on pre-implantation embryos, ATP and citrate levels were measured. There was no difference in ATP in two-cell embryos cultured to blast stage in DMSO, 10 µM DHEA or 100 µM DHEA. Citrate levels were significantly lower in the blastocysts cultured in 100 µM DHEA (FIG. 16)

Example 10

Effect of DHEA on Fetal Development

Two-cell embryos cultured to blastocyst stage in DHEA and transferred to 2.5 dpc pseudopregnant females resulted in significantly smaller fetuses, as well as smaller placentas (p=0.054) (FIG. 17 A-C). However, there was little effect on the implantation rate or resorption rate (FIG. 17D-E). Exposure of DHEA did not lead to increased anomalies in the fetuses or abnormal placental histology.

Example 11

Reversibility of DHEA Effect on Reproduction

Figure 18A:
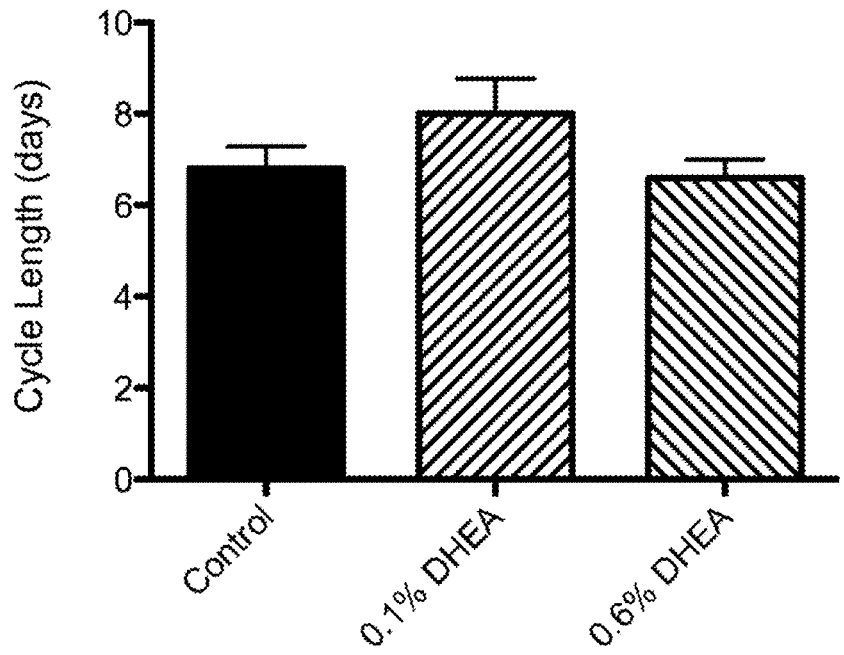
FIG. 18A-C graphically depicts reversibility of DHEA effects. (A) Resumption of normal cycles with removal of DHEA. (B) Number of pups per litter after removal of DHEA supplementation. (C) Average number of pups/litter on diet (4 females/treatment). No litters in 0.1% DHEA group.
Figure 18B:
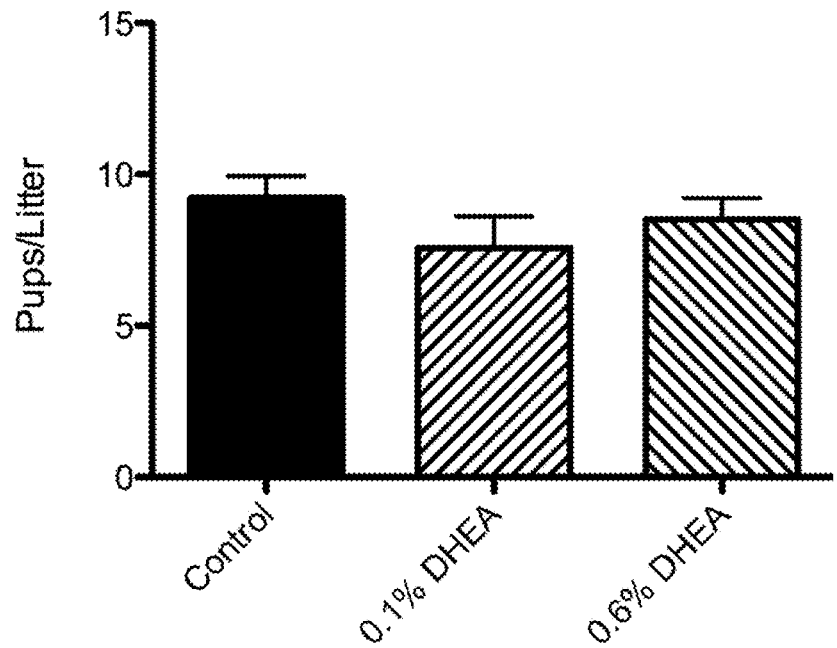
Figure 18C:
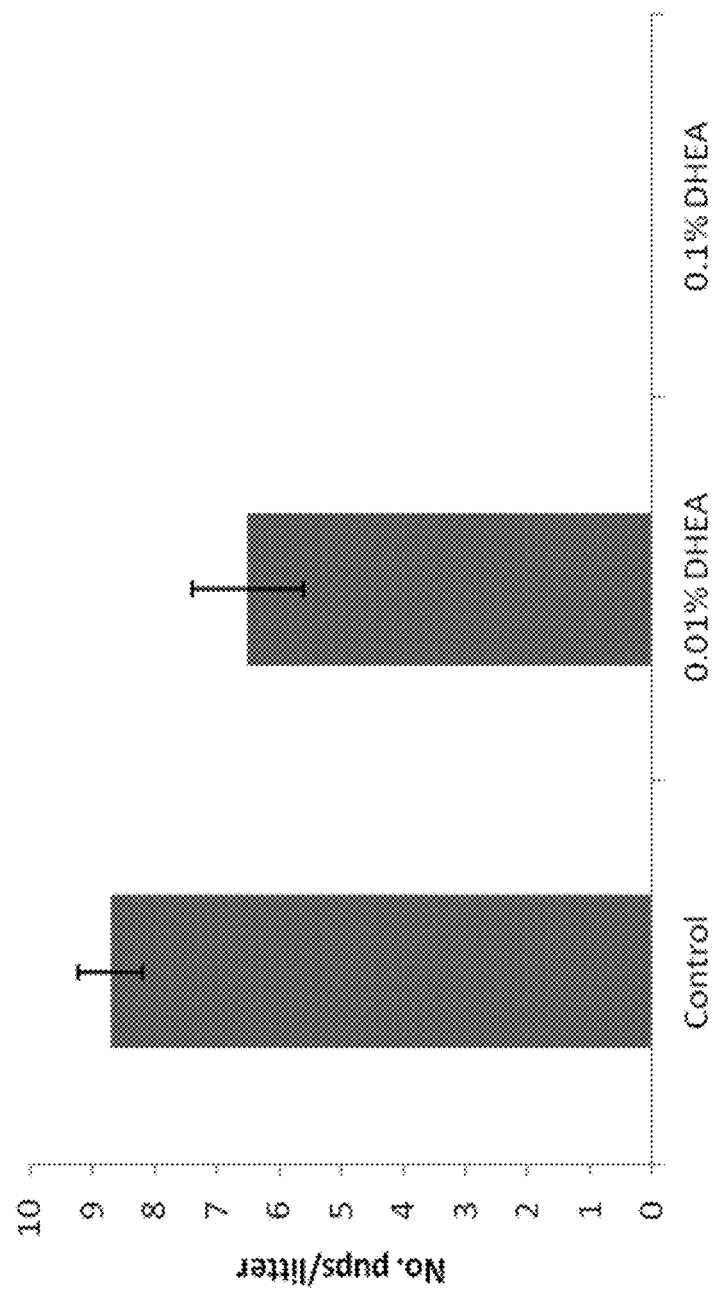

To determine the reversibility of DHEA, mice were fed the two higher DHEA diets that prevented normal estrous cycles for two weeks followed by regular rodent chow for two weeks. Estrous cycles and pregnancy rates were recorded. Mice on the 0.1% and 0.6% DHEA diet resumed normal estrous cycles with similar length as the control mice (FIG. 18A; p=0.22). Also, after return to normal chow, the mice previously fed 0.1% and 0.6% DHEA had litters similar in size to the controls (FIG. 18B; p=0.4).

Discussion for Examples 7-11

Supplementing regular rodent chow with DHEA provides a mouse model to study PCOS. The key findings from this study are that elevated DHEA negatively affects ovulation and oocyte metabolism and appears to act through inhibition of the pentose phosphate pathway. Furthermore, altered oocyte and blastocyst metabolism resulting from exposure to this diet early in development leads to impaired growth in utero. Mice were exposed to DHEA for two weeks correlating with the period of folliculogenesis in mice of 10-16 days. Supplementation with 0.01% DHEA resulted in a 1.9-fold increase in DHEA serum levels. This is comparable to what is seen in women with PCOS. The normal range of DHEA in reproductive-aged females is 1.3-9.8 ng/ml. Non-obese control women have DHEA levels of 6.54 ng/ml and PCOS women have levels of 17 ng/ml, a 2.6-fold increase. Furthermore, the mice exhibit stockpiling of early stage growing follicles as has been described previously. The DHEA exposed mice had prolonged estrous cycles with oligoovulation or anovulation similar to what is experienced by PCOS women. This decreased ovulation was overcome with the use of gonadotropin stimulation. This supports the use of DHEA supplementation in the diet as a viable mouse model of some features of PCOS.

There were similar findings in rodents exposed to subcutaneous DHEA injections of 6 mg/100 g body weight for 20 days. Treatment with DHEA prevented ovulation and resulted in persistent estrus or diestrus smears that are responsive to exogenous gonadotropins and return to normal cycles after withdrawal of DHEA. It was previously shown that serum LH was much lower in rats receiving DHEA injections, while either no change or an increase in serum FSH was seen. DHEA treated mice had higher androgen levels, but much lower 17β-estradiol levels. These studies were done in unstimulated mice with atretic follicles, in contrast to the findings in this study of increased estradiol after ovarian hyperstimulation and potential rescue of follicles from atresia. The administration of DHEA has been shown to lead to atresia of follicles, as well as abnormal mitochondria, decreased actin and degeneration in cultured granulosa cells. In DHEA-treated rodents with formation of large ovarian cysts, it is thought that the DHEA plays a critical role in atresia of these follicles and the oocyte degenerates first followed by the granulosa cells, whereas in physiologic atresia of follicles, the granulosa cells undergo apoptosis first. This is the first to report similar hormonal and ovarian changes with oral administration rather than subcutaneous injection. The potential impact of oral DHEA on fertility and oocyte quality cannot be understated as DHEA is a commonly used supplement.

The amount of intracellular ATP can affect oocyte quality and developmental competence. Although we did not find a statistically significant decrease in ATP levels in denuded GV oocytes, there was a trend toward a decrease in the ATP levels of four percent in the 0.01% DHEA group and six percent in the 0.1% DHEA group (p=0.096). Despite this small decrease in ATP, the TCA cycle metabolite citrate is significantly lower in the 0.1% DHEA group at 83% compared to control and approached significance in the 0.01% DHEA with a decrease to 90% of control. To better understand why a seemingly adequate production of ATP would not also generate citrate, the enzyme activity of G6PDH was measured, since DHEA is a known inhibitor of G6PDH, and therefore, the pentose phosphate pathway. Glucose metabolized via the pentose phosphate pathway is important for nuclear maturation in mouse oocytes, as well as the progression of meiosis and cleavage of blastocysts. Glucose metabolism in cumulus cells through glycolysis and the pentose phosphate pathway is necessary to prevent oocyte aging after ovulation by the generation of pyruvate. Oocytes from rats treated with DHEA at 1 mg/100 g body weight or 10 mg/100 g body weight were classified as GV, MI or MII and degeneration noted. The percentage of degenerated oocytes increased with the dose and treatment duration to as high as 70%, however, the mechanism was unknown. In this study, G6PDH activity was decreased in both the 0.01% DHEA and the 0.1% DHEA groups. The blockage of the pentose phosphate pathway may lead to shunting of glucose-6-phosphate to the glycolytic pathway, and therefore, increased ATP production. It is possible that the DHEA-exposed oocytes are of poorer quality than the controls but increased glycolysis compensates for ATP levels. However, the mitochondria are unable to undergo the TCA cycle properly which is reflected as lower citrate levels. Abnormalities in the pentose phosphate pathway can reduce oocyte maturation, and perhaps affect the TCA cycle, by a lack of purine substrates and an altered redox state. It has been shown that NADPH production from the pentose phosphate pathway prevents oocyte apoptosis through caspase-2. Therefore, DHEA-mediated inhibition of the pentose phosphate pathway may critically alter oocyte quality and competence.

Similar results were seen in this study in the two-cell embryos cultured to blastocysts in DHEA supplemented media. There was very little change in the ATP levels, but 10 μM DHEA and 100 μM DHEA led to decreased citrate levels of 86% and 68% of control, respectively. Therefore, DHEA can also produce negative effects post-fertilization. Transfer of blastocysts cultured in DHEA resulted in smaller fetuses and placentas at 14.5 dpc. This exposure, however, does not lead to an "all or nothing" outcome, since implantation and resorption rates were unaffected. It is unclear what impact poor in utero growth development may have on long-term outcomes. The effects of DHEA appear to be easily reversible and result in return of normal function as seen by estrous cycles of normal length and normal litter sizes.

In conclusion, the present work suggests that DHEA negatively affects oocyte quality and embryo development. The exact mechanism in which maternal DHEA exposure alters oocyte competence is not understood. Future studies may focus on the mitochondria to determine if impairment of its function plays an important role in DHEA action in oocytes and blastocysts. These findings may be clinically significant given that DHEA is often recommended to older women undergoing in vitro fertilization to achieve pregnancy. Reports thus far indicate a potential improvement in pregnancy rates in these women taking DHEA. However, it is unclear how DHEA may lead to improved oocyte and embryo quality in an older population. It is possible that DHEA may have a bimodal effect that leads to poorer quality oocytes in young healthy women, but improves outcomes in women with diminished ovarian reserve. A better understanding of the role DHEA plays in oocyte and blastocyst metabolism may lead to therapeutic targets in women with PCOS or hyperandrogenism; as well as better selection of patients who may benefit from DHEA supplementation.

Materials and Methods for Example 7-11

Animals

Female FVB/NJ mice were obtained from Jackson Laboratories (Bar Harbor, Me., USA). Regular rodent chow was supplemented with DHEA at 0.01%, 0.1% and 0.6% w/w. Three-week-old mice had access to food and water ad libitum. Mice were fed control or DHEA-supplemented chow for two weeks. The Animal Studies Committee at Washington University School of Medicine reviewed and approved all animal experiments. Animals were maintained according to the Guide for the Care and Use of Laboratory Animals provided by the Institute for Laboratory Animal Research.

Hormone Concentration

Control and DHEA-fed mice were superovulated with 10 IU pregnant mare serum gonadotropin (PMSG) by i.p. injection. DHEA, estradiol and testosterone serum concentrations were measured 48 hours later. For progesterone concentrations, mice were given an i.p. injection of 10 IU hCG 48 hours after PMSG and blood was collected 24 hours later. Mice were anesthetized with 50 μl ketamine and xylazine (1:1) and blood was collected by cardiac puncture. Serum was separated by centrifugation and stored at −20° C. ELISA assays were used to determine serum hormone concentrations (Alpco, Salem, N.H., USA).

Histology

For histological evaluation, one ovary from five mice in each group was fixed in Bouin's solution, transferred to 70% ethanol then embedded in paraffin and serial sectioned at 10 microns. Every tenth section was kept and stained with hematoxylin and eosin. Follicles with visible nuclei were classified as primordial, primary, secondary or antral. Corpora lutea were also counted. Follicle counts from each classification were summed for each mouse.

Estrous Cycles

Vaginal smears were performed daily starting at eight weeks of age, after puberty, and establishment of regular estrous cycles. Vaginal cells were collected in 10 μl of phosphate buffered saline (PBS) and evaluated for stage of estrous by one investigator by light microscopy.

Oocyte Collection

COCs were collected following superovulation with PMSG. Ovaries were removed and placed in M2 media (Sigma, St. Louis, Mo., USA). COCs were obtained by rupture of antral follicles with a syringe and needle. To collect denuded germinal vesicle (GV) oocytes, the cumulus cells were removed by gentle pipetting. The oviducts were removed from PMSG- and hCG-primed mice. The ampulla of the oviduct was punctured to release the clutch of ovulated oocytes 24 hr after hCG.

Blastocyst Culture and Embryo Transfer

Mice were superovulated and mated with males of known fertility. Forty-five hours after injection with hCG, the oviducts were removed. Two-cell embryos were collected by flushing the oviducts with human tubal fluid media (HTF) with 0.25% BSA. Embryos were cultured in HTF with BSA and either DMSO, 10 μM DHEA or 100 μM DHEA for 72 hours. In vitro cultured blastocysts were transferred to 2.5 days postcoitus (dpc) pseudopregnant ICR females. Resulting embryos and placentas were collected at 14.5 dpc and fixed with Bouin's solution, embedded in paraffin and sectioned.

Metabolite and Enzyme Assays

Denuded oocytes or cultured blastocysts were frozen on a glass slide with liquid nitrogen and dried overnight at −35° C. under vacuum. Individual oocytes or blastocysts were extracted in nanoliter volume under oil. Assays were designed to measure ATP, citrate and G6PDH by linking with NAD/NADH or NADP/NADPH which are enzymatically amplified in a cycling reaction allowing products to be measured by fluorometry.

Pregnancy Rates

Control and DHEA-fed mice were mated with males of known fertility until three litters were delivered or up to 12 weeks.

Statistics

Data are represented as mean±SEM. ANOVA followed by appropriate post hoc analysis (GraphPad Prism, La Jolla, Calif., USA) was used for comparisons between control and experimental values. P values of <0.05 were considered significant.

Example 12

DHEA and 6-Aminonicotinamide Intrauterine Pellet Formulations and Pregnancy Outcome Endometrial stromal cells (ESC) undergo hormone-driven decidualization as a requirement for proper embryo implantation. As demonstrated in the Examples above, 6-aminonicotinamide (6-AN) and dehydroepiandrosterone (DHEA) inhibit the pentose phosphate pathway (PPP) leading to dramatic decreases in decidual marker expression in vitro and decreased decidualization in vivo. In addition, it was shown that mice fed a DHEA diet experience decreased ovulatory rates and poor oocyte quality compared to controls. Together these results strongly suggest that PPP inhibition by either of these two compounds may be a suitable contraceptive target for use in an intrauterine contraceptive device. Here, data is presented on pregnancy outcomes in mice receiving a specially formulated DHEA, 6-AN or placebo pellet placed in the uterine horn.

ICR female mice had either placebo (n=26), DHEA (1.5 mg/60 days)(n=20), or 6-AN pellets (150, 15, 1.5 mcg/60 days)(n=24) placed into the uterine horn after index delivery. Females were then mated and litter size was measured over the following 120 days post pellet. Mice were housed according to the Institutional Animal Care and use Committee and NIH guidelines. Day to first litter, number of litters, number of pups, average pups/litter were recorded. Serum DHEA levels were quantified (Alpco, Salem, N.H.). All pellets (placebo, DHEA, 6-AN) were custom-formulated (Innovative Research, Inc).

Figure 19:
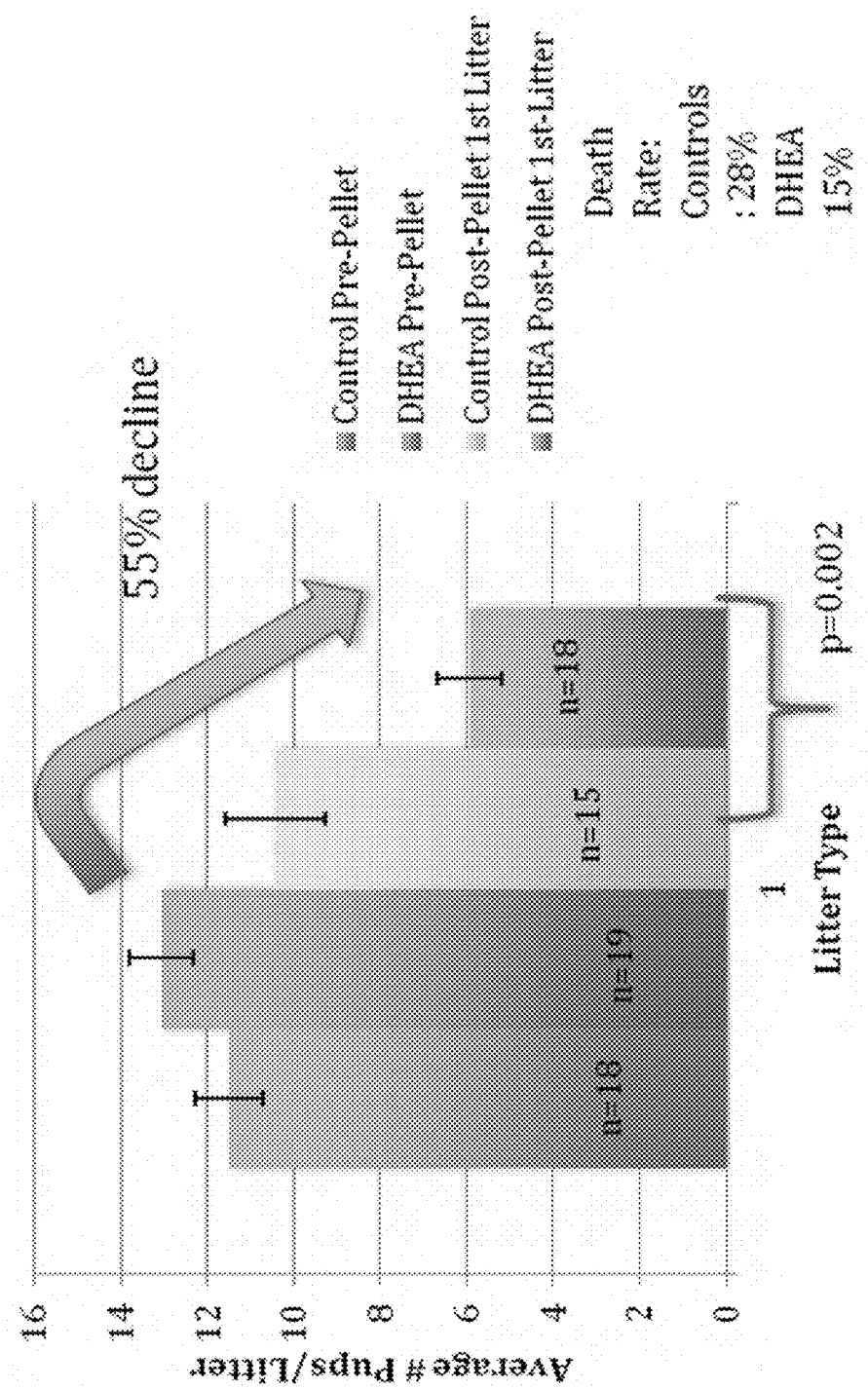
FIG. 19 graphically depicts the effect of intrauterine DHEA formulation on time to first litter.
Figure 20:
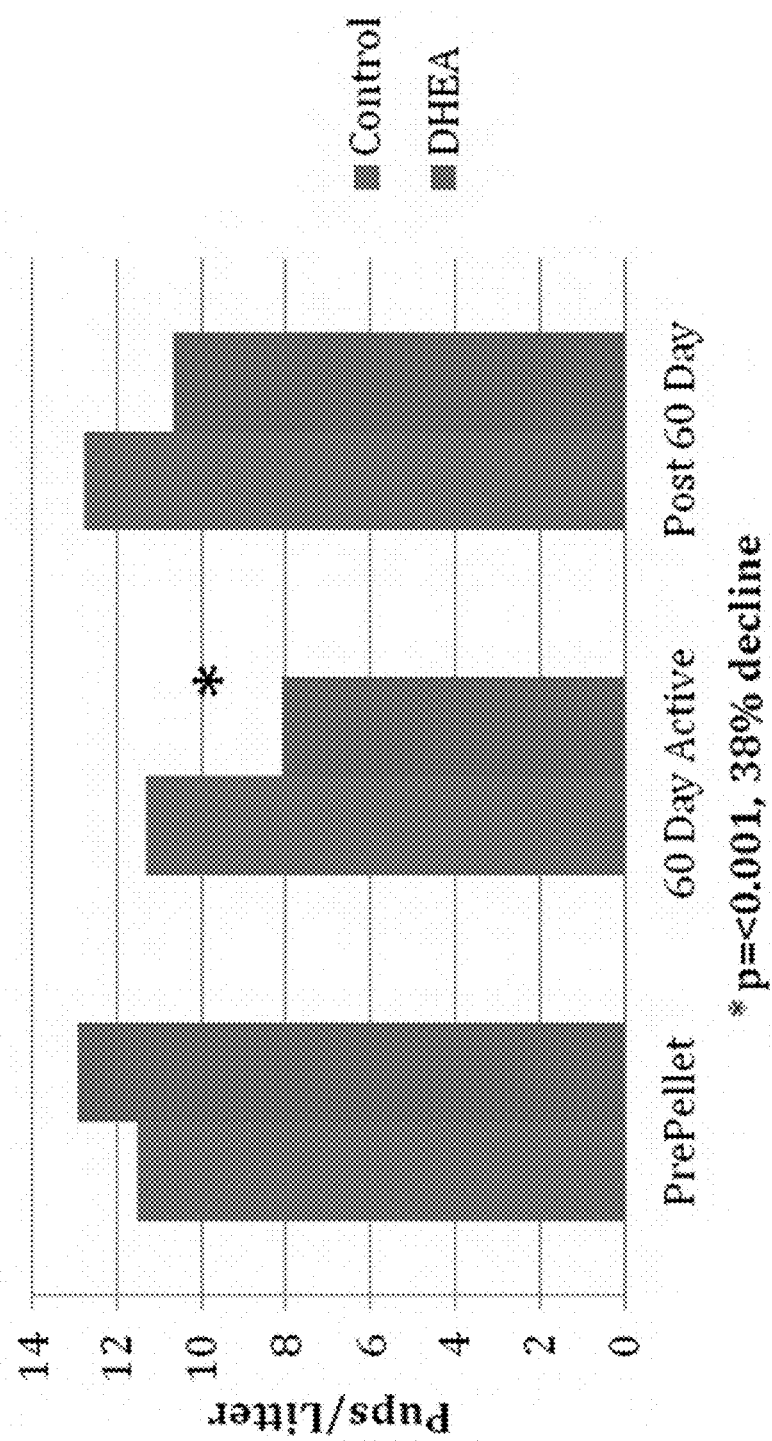
FIG. 20 graphically depicts the effect of intrauterine DHEA formulation on litter size.

DHEA mice had a longer average time to first litter compared to controls (34 days vs 27 days p=0.05; FIG. 19). The average pups/litter size was reduced by 55% in the first litter after placement of the pellet in the DHEA group (13.0 pups/litter vs 5.9 pups/litter, p=0.002; FIG. 20) but returned to normal after 60 days (12.3 pups/litter control vs 10.3 pups/litter DHEA, p=0.3). Mice given a 6-AN pellet saw a 37.7% reduction in average pup/litter size however this difference was not significant from control (p=0.4). Additionally, 6-AN mice had a longer mean time to first litter (34 days vs 27 days) in this group, too; however it was not significant (p=0.1). Additionally mean serum levels of DHEA were slightly elevated, but within normal range (0.512 vs 0.265 ng/mL, p=0.07) in the DHEA group vs controls, respectively Intrauterine pellets containing DHEA and 6-AN impair proper embryo implantation leading to diminished litter size as compared to mice receiving placebo pellets. Moreover, this effect is reversible since litter sizes return to normal following the 60 day timed-release of the pellets. In conclusion, both hormonal (DHEA) and non-hormonal (6-AN) inhibitors of the PPP, released slowly in an intrauterine pellet, may have a contraceptive effect acting locally on the endometrium.

Example 13

Inhibitory Effect of Glucosamine on Decidualization in Human Endometrial Stromal Cells Decidualization is the process by which endometrial cells undergo drastic morphological and functional changes in order to differentiate into decidual cells. The newly decidualized endometrial stromal cells (ESC) are thought to provide the blastocyst with various metabolic factors essential for further embryo implantation and development. Glucose utilization is critical for the decidualization process. As shown in the examples above, it has recently shown that dehydroepiandrosterone (DHEA) inhibits this differentiation process by inhibiting glucose utilization via the pentose phosphate pathway (PPP). The PPP is primarily an anabolic pathway that oxidizes glucose and generates reducing equivalents. In this study, it is hypothesized that a non-hormone amino sugar, glucosamine (GlcN), also inhibits ESC decidualization via inhibition of the PPP.

Figure 21A:
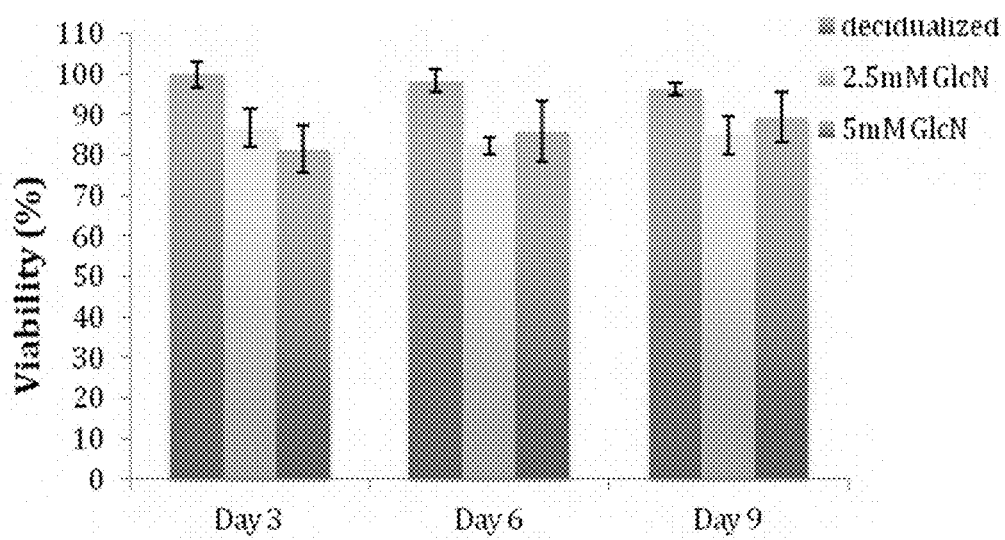
FIG. 21A-B provides graphical evidence that glucosamine does not affect proliferation of hESC-T. Cell viability rates were assayed by MTT assay (A) and (B) by flow cytometry.
Figure 21B:
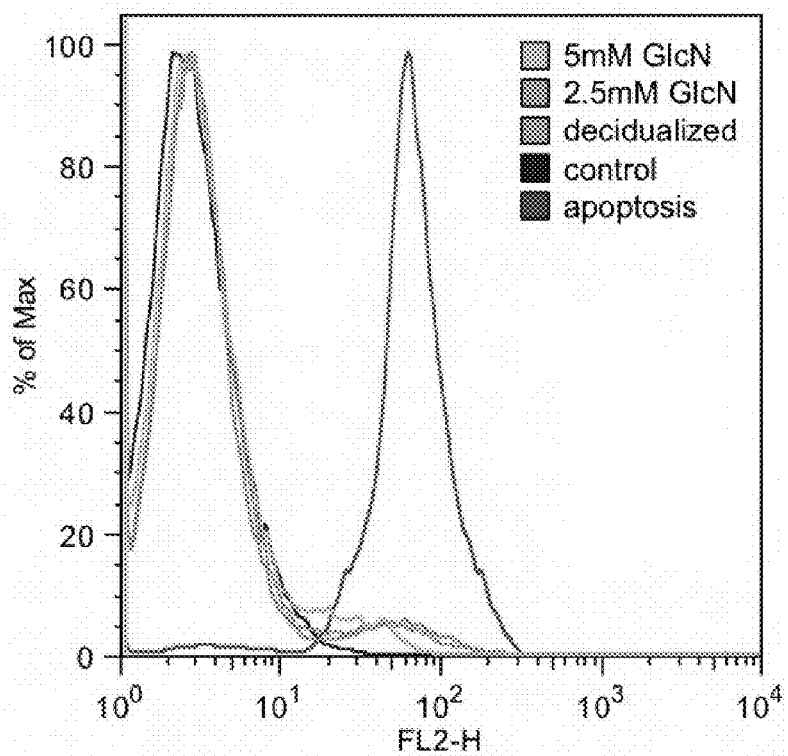
Figure 22A:
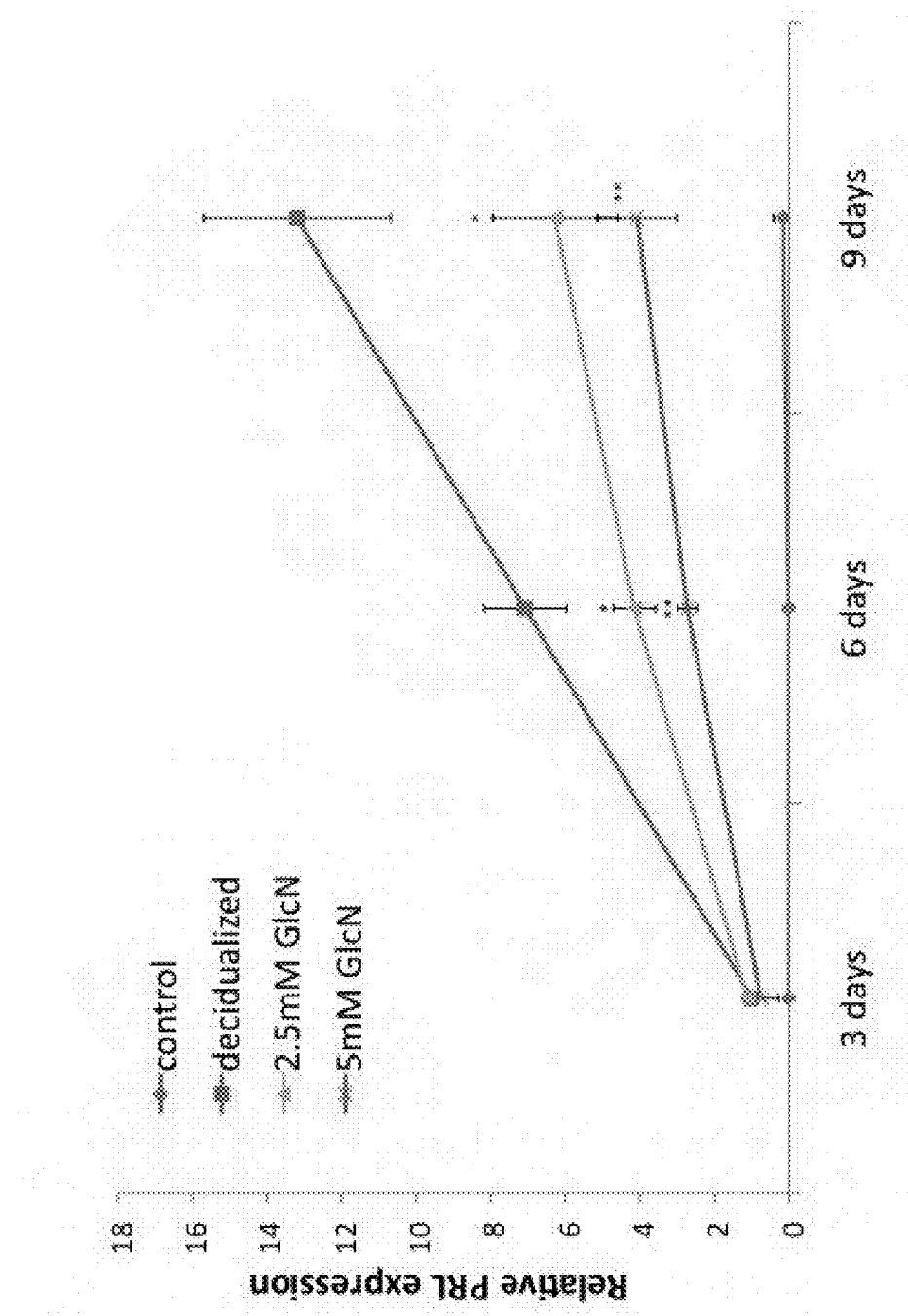
FIG. 22A-C graphically depicts GlcN inhibition of decidualization of immortalized hESC-T cells in vitro. hESC-Ts were treated with bd-cAMP and MPA to induce decidualization in vitro, and the differentiation was assessed by monitoring the expression levels of mRNA for the decidualization markers. GlcN decreased the expression levels of both (A) PRL and (B) SMST starting as early as day 3 and continuing through day 9. (C) Expression levels of IL-15, LEFTY2 and TIMP3 were assessed on Day 9 of culture. Values are a mean of at least three independent experiments±SEM. *, $P<0.05$; **, $P<0.01$ compared with the decidualized sample.
Figure 22B:
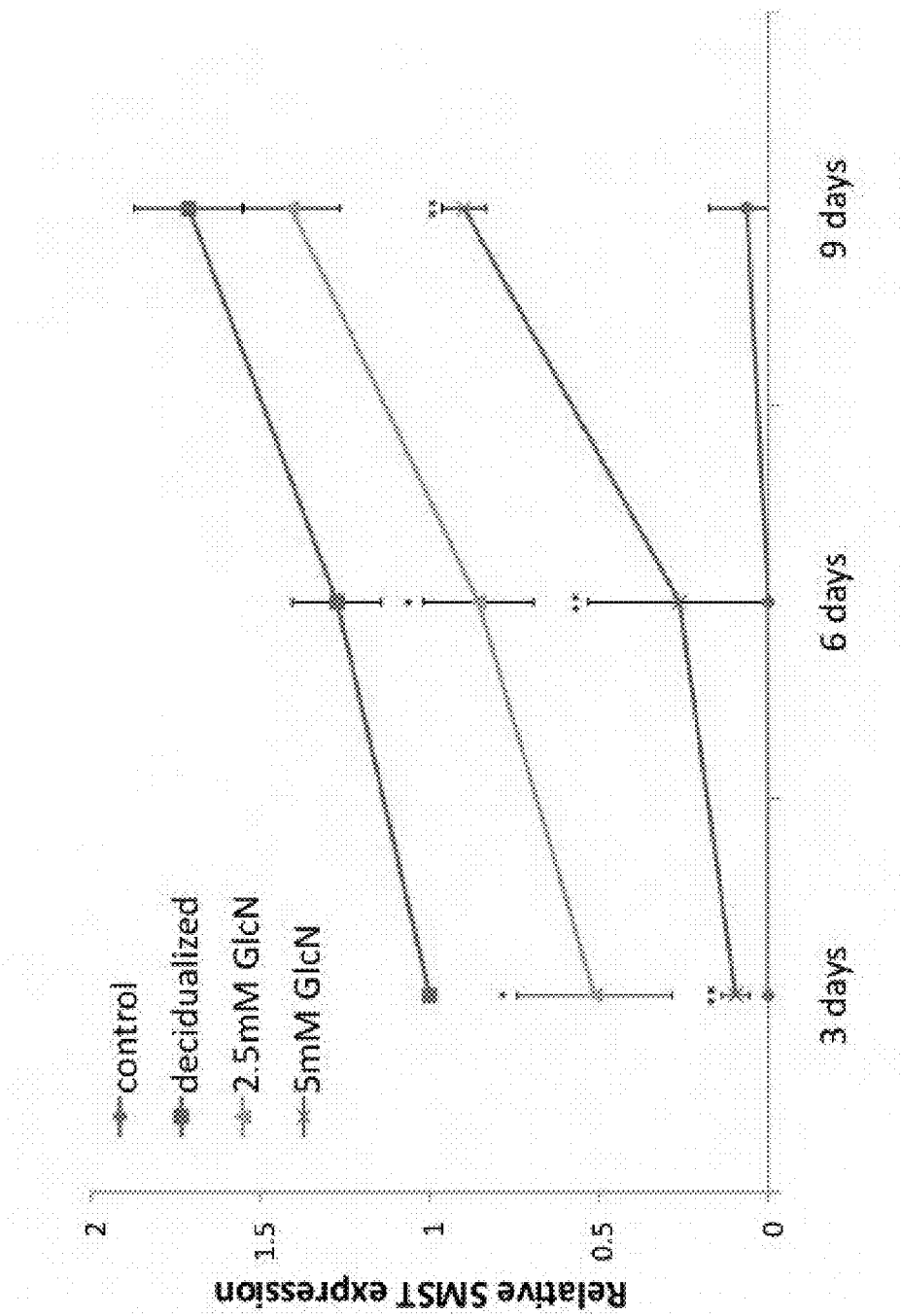
Figure 22C:
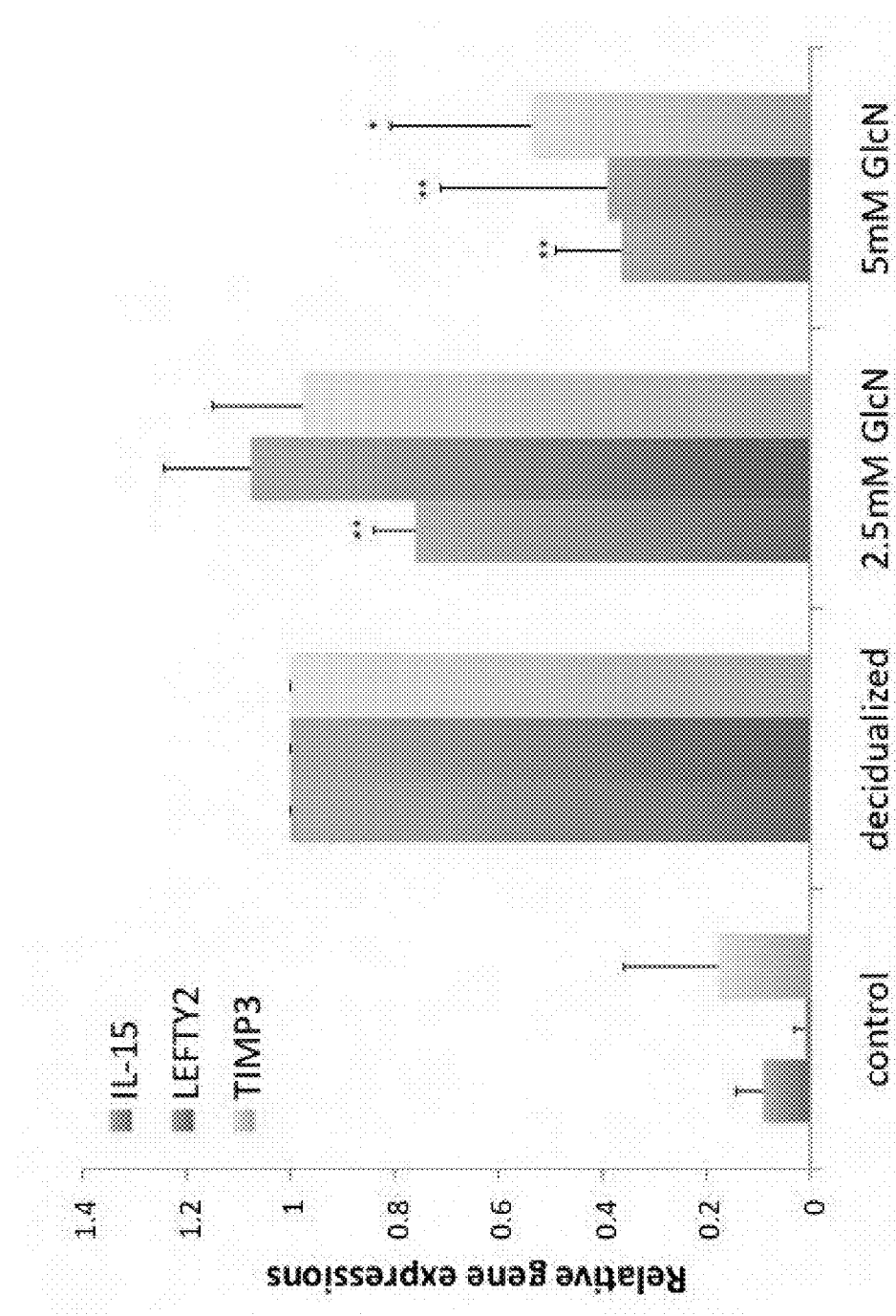
Figure 23:
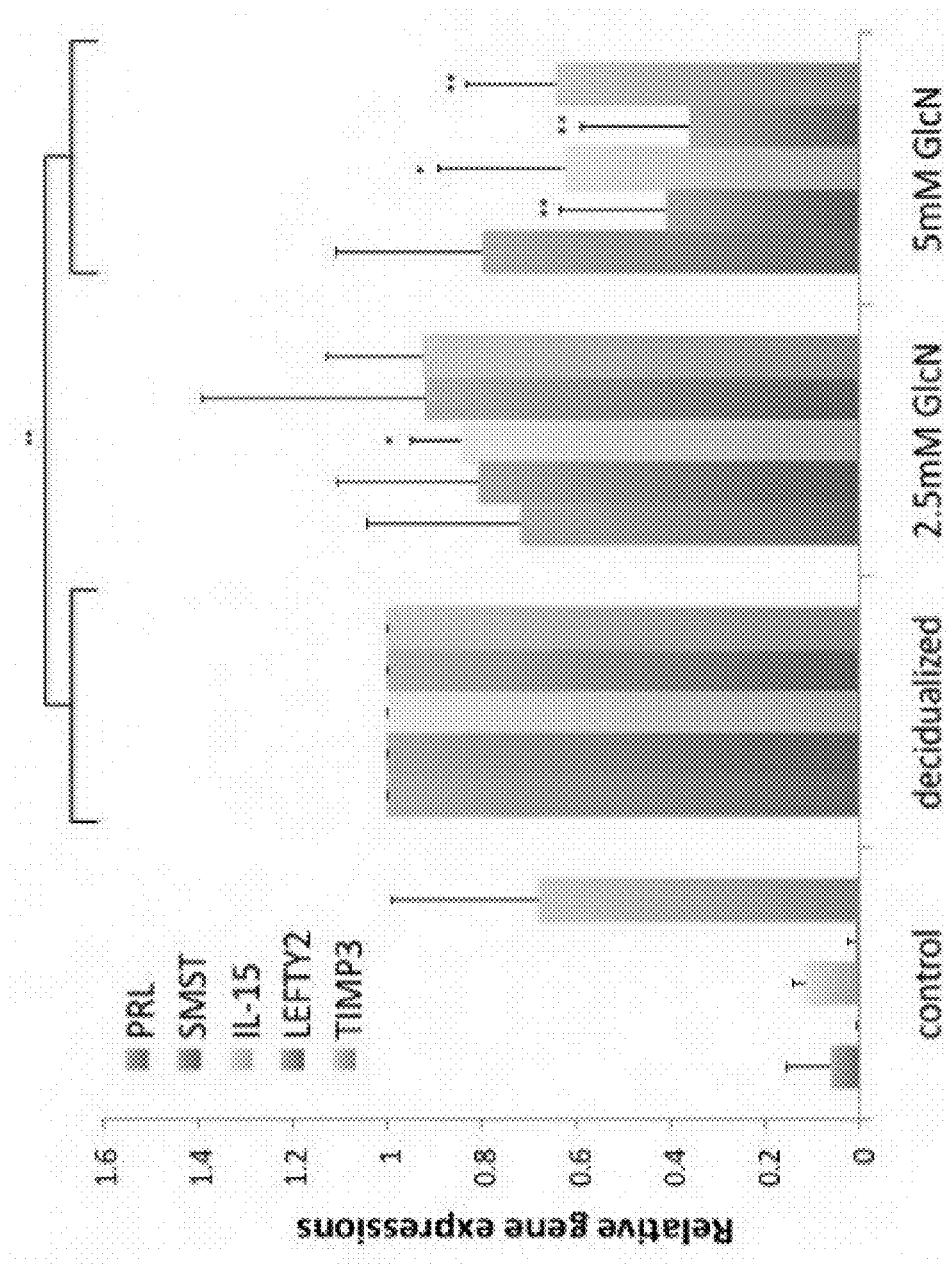
FIG. 23 graphically depicts GlcN inhibition of decidualization of hESC primary cells in vitro. Human primary ESC were isolated from hysterectomy samples and decidualized with db-cAMP and MPA. The expression of decidualization markers was assessed on day 9 of culture. Values are a mean of at least three independent experiments±SEM. *, $P<0.05$; **, $P<0.01$ compared with the decidualized sample.
Figure 24:
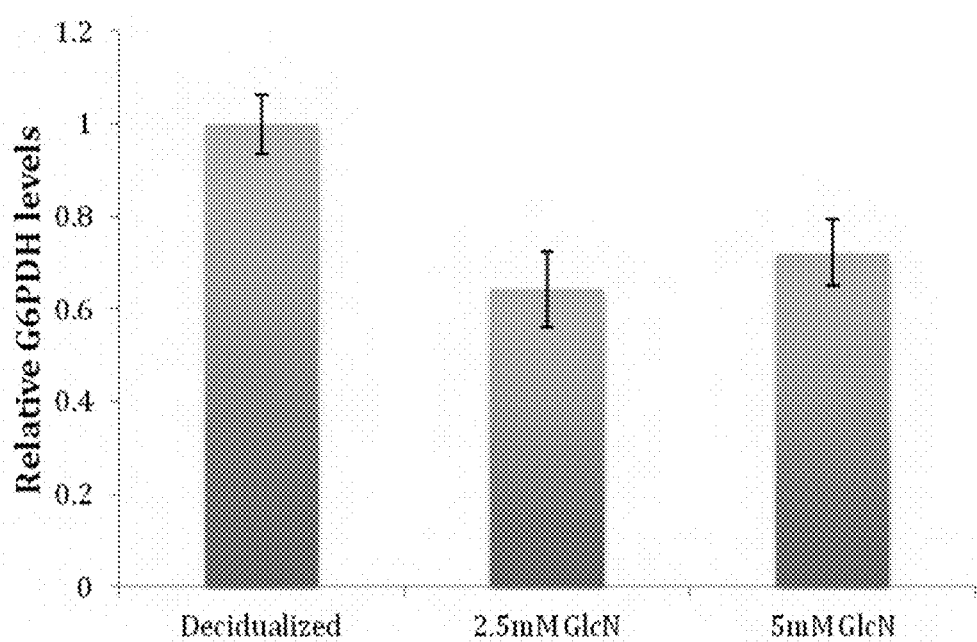
FIG. 24 graphically depicts relative G6PDH activities in hESC-T cells.
Figure 25A:
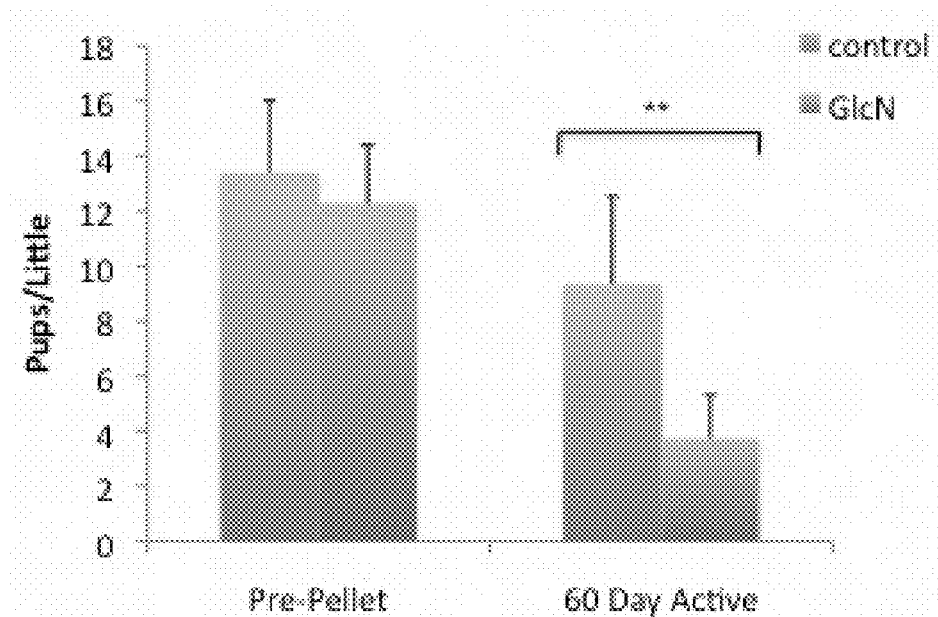
FIG. 25A-B graphically depicts decreased birth rate by glucosamine in ICR mice. 6 weeks old ICR female mice were implanted with a control or GlcN (15-1500 μg) pellet on one uterine horn and (A) with or (B) without the hysterectomy on the other uterine horn. Pups per litter in pellet implanted female mice crossed with males were recorded. **, $P<0.01$.
Figure 25B:
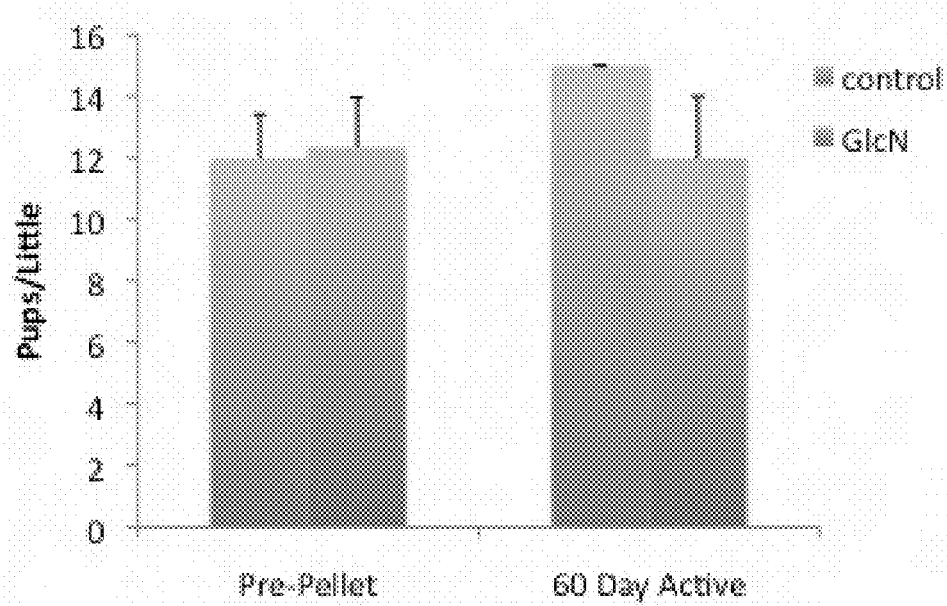

Human immortalized ESC (ESC telomerase immortalized, ESC-T), were decidualized in vitro in the presence of 0, 2.5 or 5 mM GlcN for 9 days. These cells showed viability similar to control cells by MTT assay and flow cytometry, suggesting that GlcN did not affect proliferation of ESC-T (FIG. 21). As measured by quantitative RT-PCR, however, exposure of in vitro decidualized ESC-T as well as human primary ESC to GlcN resulted in significantly lower expression levels of mRNA for the decidualization markers prolactin, somatostatin, interleukin-15, left-right determination factor 2, and tissue inhibitor of metalloproteinase 3 as compared to controls (FIGS. 22 and 23). In addition, it was demonstrated that G6PDH activity, the rate-limiting enzyme of the pentose phosphate pathway, was significantly lower in these decidualized ESC-T cells exposed to GlcN as compared to control cells (FIG. 24), suggesting that GlcN is an inhibitor of the PPP, similar to DHEA. Thus, it was concluded that perturbation of the PPP activity by GlcN might lead to the failure of ESC decidualization and thus possibly be one of the first non-hormonal inhibitors of decidualization. Finally, in vivo evidence is provided that female mice with a time-release GlcN pellet (15-1500 µg) implanted in one uterine horn, delivered fewer live pups per litter over a 60-day period than those with control pellet implantation (8.25 vs 4.23 pups/litter; FIG. 25). Taken together, the outcomes of this study suggest a role of GlcN in the regulation of decidualization and pregnancy via the pentose phosphate metabolic pathway.

What is claimed is:

1. A method of blocking decidualization of endometrial stromal cells in the uterus of a female mammal, the method comprising locally administering in the uterus an effective amount of an inhibitor of glucose-6-phosphate dehydrogenase, wherein the inhibitor is selected from the group consisting of dehydroepiandrosterone (DHEA)-sulfate, halogenated DHEA, and DHEA, and wherein the inhibitor of glucose-6-phosphate dehydrogenase blocks decidualization of the endometrial stromal cells in the uterus of the mammal.

2. The method of claim 1, wherein the inhibitor is administered using an intrauterine device (IUD).

3. The method of claim 1, wherein the inhibitor is administered in combination with other contraceptives.

4. The method of claim 1, wherein the inhibitor is DHEA.

5. The method of claim 4, wherein DHEA is administered using an intrauterine device (IUD).

* * * * *